(12) United States Patent
Gallagher et al.

(10) Patent No.: US 9,506,066 B2
(45) Date of Patent: Nov. 29, 2016

(54) REPRESSOR ON IFN-λ PROMOTER AND SIRNA AGAINST GATA1, EVI1, AND CRX TO ALTER IFN-λ GENE ACTIVITY

(71) Applicant: Medical Diagnostic Laboratories, LLC, Hamilton, NJ (US)

(72) Inventors: Grant Gallagher, Milltown, NJ (US); Joyce Eskdale, Milltown, NJ (US); Rachael Siegel, Fords, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 10 days.

(21) Appl. No.: 14/557,623

(22) Filed: Dec. 2, 2014

(65) Prior Publication Data

US 2015/0167001 A1    Jun. 18, 2015

Related U.S. Application Data

(60) Continuation of application No. 13/771,855, filed on Feb. 20, 2013, now Pat. No. 8,933,049, which is a continuation-in-part of application No. 13/693,383, filed on Dec. 4, 2012, now Pat. No. 8,802,648, which is a division of application No. 12/799,925, filed on May 5, 2010, now Pat. No. 8,349,808.

(60) Provisional application No. 61/215,428, filed on May 5, 2009.

(51) Int. Cl.
*A61K 31/70* (2006.01)
*C07H 21/02* (2006.01)
*C07H 21/04* (2006.01)
*C12N 15/113* (2010.01)
*G01N 33/50* (2006.01)
*A61K 31/713* (2006.01)
*C12Q 1/68* (2006.01)

(52) U.S. Cl.
CPC ......... *C12N 15/1136* (2013.01); *A61K 31/713* (2013.01); *C12N 15/113* (2013.01); *G01N 33/5044* (2013.01); *C12N 2310/14* (2013.01)

(58) Field of Classification Search
None
See application file for complete search history.

(56) References Cited

U.S. PATENT DOCUMENTS

2015/0166991 A1 * 6/2015 Perkins ............. A01K 67/0276
424/139.1

* cited by examiner

*Primary Examiner* — Sean McGarry
(74) *Attorney, Agent, or Firm* — Siu K. Lo

(57) ABSTRACT

The present invention is directed to the identification of a novel repressor located between ~1.2 kb to ~1.6 kb from the translation start site of the IFN-λ1 promoter. The present invention provides a method of using siRNAs against ZEB1 (binds to the repressor region) and BLIMP-1 (binds outside the repressor region) and increases the promoter activity of IFN-λ1 (i.e., increases the production of IFN-λ1 protein). siRNAs against ZEB1 mRNA or BLIMP-1 mRNA increase IFN-λ1 gene activity. There is provided a therapeutic application of siRNAs against ZEB1 and BLIMP-1 mRNAs in treating a mammal (including a human) by increasing the production of IFN-λ1 protein that promotes an anti-viral response as well as treats asthma diseases and colon diseases.

12 Claims, 39 Drawing Sheets

Figure 2A.

IFN-λ1 Promoter Fragment (SEQ ID Number: 1)

```
   1 gctacagtat tgccagcata tagaccctcg agcacttctg gagagaggga tacaggtgca
  61 actatttggg agagcaaagg atgaatatgt agagctgtgc tgcccatcat gatagccact
 121 agccacatac agtaattaaa tttaaataaa atgaaataaa ttgaaaattc agttcctgca
 181 ttgcacttgc caaattttaa atacctaaca gccacattgg acgtaaaga tgcacaatat
 241 ttctgtcatt gcagaaagtt ctaatgaaca gcactgatta gaccatataa gcacaggtat
 301 gccctgtgac ccagcaatct tcagttcagg ttctcccaaa agcatatcct gaagccaaag
 361 atgcaggtgg cttatttggg agctgtttcc cagaagcaca agcgagtggg gaaactgagc
 421 caggaagagc aaaaagccaa taaatggtgc agagtctgga gtagagggag gcacctagag
 481 cacttccctg actcagagtg agcacctcct taatttttgt ttgtttgttt gtttgttgag
 541 acagagtctc actctgtcac ccaggctgga gtgctgtggc acaatctcgg ctcactgcag
 601 cctccgcctc ccaggctcaa gcgattcctg tgactcagcc tcctgagtag ctgggtttac
 661 aggcacatgc caccacacc agctaatttt tgtatttta gtagagacag ggtttcacca
 721 tgttggccag gctggtctcg aactcctggg ctcaggtgat ctgcccacct cggcctccca
 781 aaatgctggg attacaggtg tgagccacca cgcctggccc cctgcttaaa ttttgactct
 841 ggtccctaa tttgaccac cctaattcca gccccaaaa aggctactgc tgtgagcagc
 901 tagaagtcat ttgttctggg gacagtcaga agatcaagga gtcatgtaga agtcgcccga
 961 gaattgaccc tccaagggaa agggaagctg cagtatttat tccattgctt tcagccctca
1021 ctgtttgagg actgctactg ggggaatcaa tcctgctact tccagtccat tctgcatgtg
1081 ggcagtagaa aggccttggt ctccagcaga gaagcagaaa gatccaagca cgtgaggcag
1141 gaaactgtca gcctgtgtgg gaactgacca ccatatccac aagccgaggg gatacagtag
1201 agggcatcag ctggtgtgct accgtatatt ccagaaagcc gcccacccag aggacaggtg
1261 tgagccttat ggtaatgggg agctagaggc aacctaagtg tccatcactg ggggaatagg
1321 taagtaaaag tgctgtggtt gtatacacca tgaaatacag tgcacaggaa acttgatgta
1381 cacagcttgt gaagagatct cagaagcagt gttaagttaa aaaataaaaa agaaagaagt
1441 agaagattta tagcacaatt ccacttatgt aaattggaaa cacatacaca cacgagatca
1501 caaattataa agatacatct ttgcagctat ttatcaagtg cattatagtg ggtgtctgtg
1561 ggggtgcgat gggaatggga attggcaatg gaggaataaa agccttggag ggtctttcat
1621 gggccaattg tgatcctgtg ttatgatctg aagagtatga ttaataactt tctgcaccaa
1681 agggctaaga aaaaaaataa aggagtgaaa ataggaaatg tctgcacatc agagcagttt
1741 cttacctgct acacaattac tattactgca gggatgatga tagcaaggca accagactca
1801 ccgcctgcct tctctccagg cagccctcc agtccccagg aaatgcgctt gccccagcg
1861 aataaggagt tcctaccc tctcatgcta cccagaggga cagaaggag aagtgggcct
1921 gctaccccca gaggttctca tcttctacct gggctgcata tggaataggg agcaagtaca
1981 taggactcat cataccccat ttctgcctct atccactgt gggaccttag gcaagtcact
2041 ttgccttcct atgcctcagt tatctcacta gtaaatggg catgattatt gtattagtca
2101 gggttctcca gagagacaga acaaatagga tgttggata aatagatgat agatagagag
2161 atatagacta gatagatgag agagatagac tagatagaga gagagagaga gagagagaga
```

Figure 2B.

IFN-λ1 Promoter Fragment (SEQ ID Number: 1)

```
2221 gagagagact agatagatga gagagagata ggaggggatt tattagggga attggctcag
2281 acaattaggg aggctaagaa gttccacaac aggccatctg caagctggag aaccagggaa
2341 gcttgtagtg cagctcagtt ccagaataaa agcctcagga cttaggggt agctagtgca
2401 agtccagca tttttttttt tctgagatg gagtctcact ctgttgacca ggctggagtg
2461 cagtgacatg atctcagctc actgcagcct ccgcctccag ggtcaagcg atactcctgc
2521 ctcagcctcc caagtagctg ggactacagg cctgtgccac cacgcctggc tgattttat
2581 atttttagta gagatggggt ttcaccatgt tggccaggct ggtctcgaac tcctgacctc
2641 aagtgattca cctgcctcag cctcccaaac tgctgggatt acaggcgtga gccaccatgc
2701 ccagctgcac atcccagcat tcaaagacca aagagcctgg agtctgatg tttaagggca
2761 ggtgcaggt gtccagctc ataagagaga gcaaattctc ctttcctctg ccttttgtt
2821 ctattcaggc cctcggccaa ttggatggtg cccaccacat tgggtaacaa cgggtcttcc
2881 ttactcagtc cattgattca aatgccaatc tcttctggaa acaccccaga gtcataccca
2941 gaattaacgc atcaccagct atctgataaa cttaaccagt caaggtgaca cctaaaatta
3001 accatcacaa ttataaaaat aactactcag agaaacatta ggagcatgaa ctgaaattag
3061 ttaatgggac attcttaaac caatggcaga agctccttct tggccaggag cagtggctca
3121 tgcctttaat actagcactt tgcgaggctg aagcaggagg atggcttaag gccaggagtt
3181 caagactggc ctgggcaaca tagtgagacc ctatctcta caaaaataaa taaataaata
3241 ataaagtaag gtggtggctc acgcctgtaa tcccagcact ttgggaggcc aaggcaggca
3301 gatcatctga agtcaggagt tcgaagccag cgtgaccaac atagtaaaac ccagtctcta
3361 ctaaaaatac aaaaactagc caggcgtgat ggcatgcacc tgtaatccca actactagg
3421 aggctgaggc aggagaatcg cttcaactcg ggaggcagaa gttgcagtga gccaagattg
3481 caccattgca ctccagcctg ggcaacaaga gcaaaactac gtctcaaaaa ataataataa
3541 caataaaata aaaaacaagc ttttttttt ttgaaacagg atctcactcc atcacccagg
3601 ctggagtgca gtggcacgat cttggctcac tgcaacctcc gcctccggg ttcaagtgat
3661 tctcatgcct cggcctcctg agtagctgag accacaggcg catgccacca cctggcta
3721 atttagaata aaaagaagc ttcctctctg ccactcaggt agccttatcc ctaatctcag
3781 cctccgtcag ggactccctg aggccagttg gctgaaagct gcccagggag ttctaaggat
3841 ttcagtttct ctttccttct tgatgcagct ccagctcac ttggccctgc ccacacctgt
3901 tccctcatca ggctcccaga cgggccccgc ccactcatgc ctcttaagtc aaagtggaaa
3961 ttctcatttc caattaccctt ttcactttac acacatcatc ttggattgcc catttgcgt
4021 ggctaaaaag cagagccatg ccgctgggga agcagttgcg atttagcc
```

//

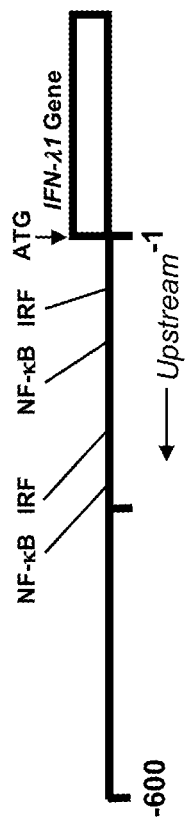
Figure 7A IFN-λ1 Putative Promoter
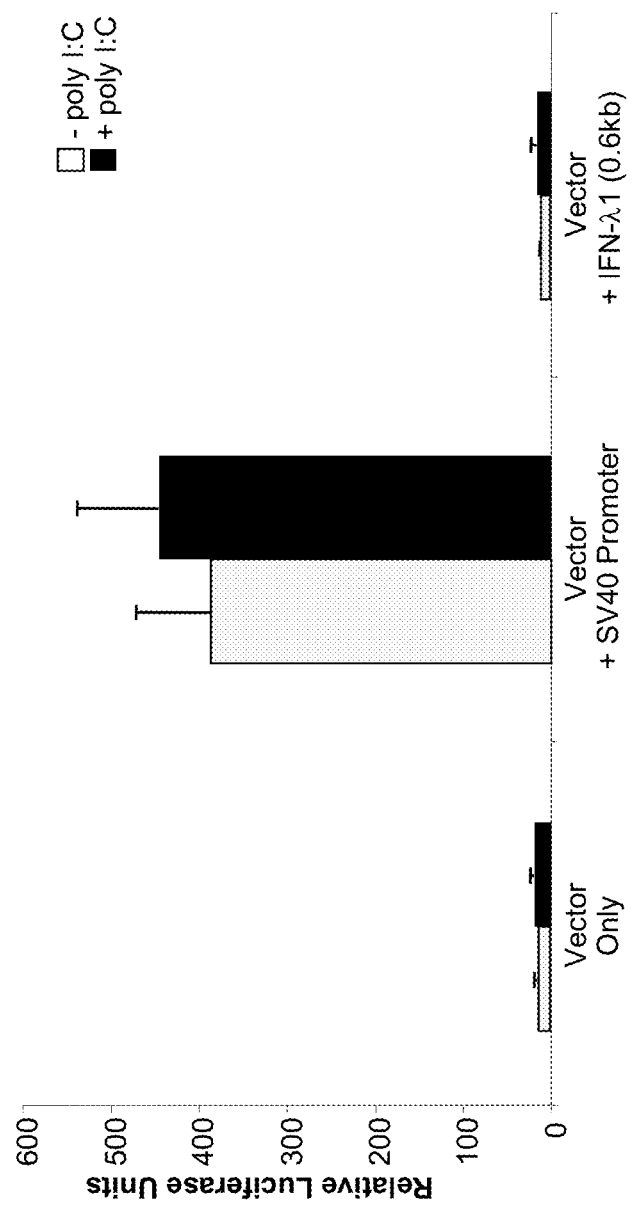
Figure 7B Luciferase Assay

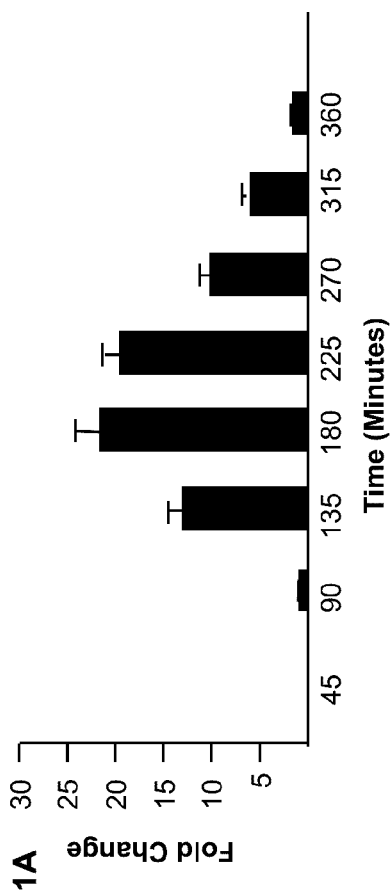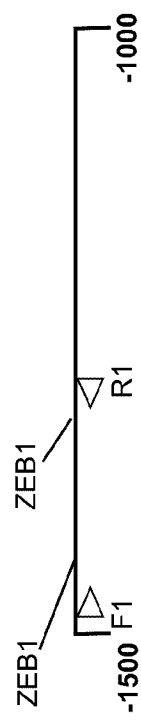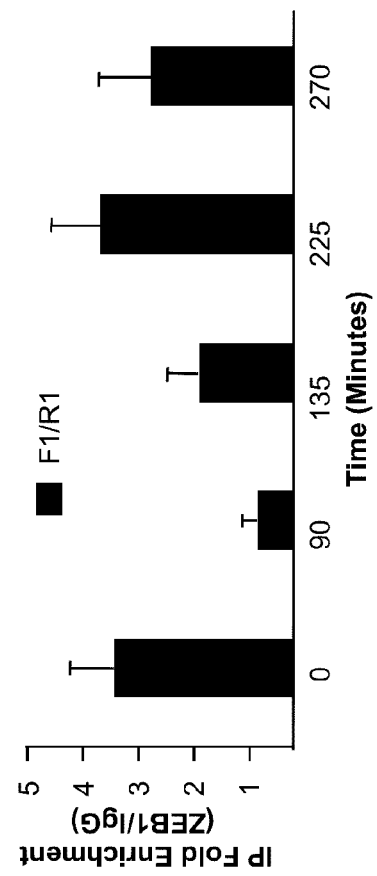
Figure 11A
Figure 11B
Figure 11C

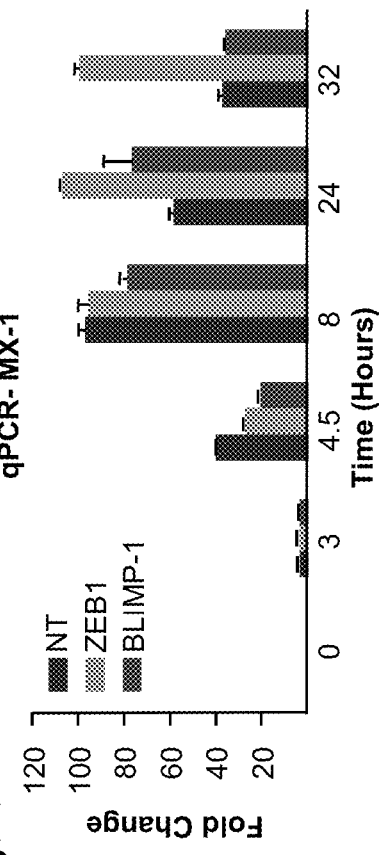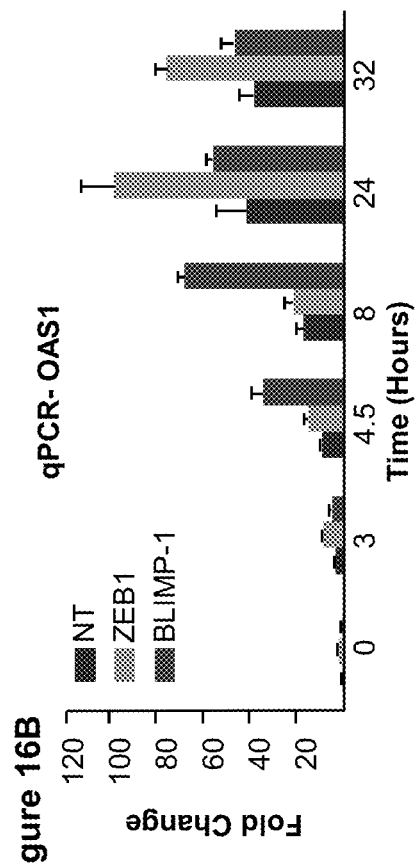

Colon Epithelial Cells

Bronchial Epithelial Cells qRT-PCR – IFN-λ1

Colon Epithelial Cells

Bronchial Epithelial Cells qRT-PCR – IFN-λ1

Bronchial Epithelial Cells

Colon Epithelial Cells

IFN-λ1 ELISA

Bronchial Epithelial Cells

Colon Epithelial Cells

SEQUENCE LISTING

<160> NUMBER OF SEQ ID NOS: 71

<210> SEQ ID NO 1
<211> LENGTH: 4068
<212> TYPE: DNA
<213> ORGANISM: Homo sapiens

<400> SEQUENCE: 1

```
gctacagtat tgccagcata tagaccctcg agcacttctg gagagaggga tacaggtgca      60
actatttggg agagcaaagg atgaatatgt agagctgtgc tgcccatcat gatagccact     120
agccacatac agtaattaaa tttaaataaa atgaaataaa ttgaaaattc agttcctgca     180
ttgcacttgc caaattttaa atacctaaca gccacattgg accgtaaaga tgcacaatat     240
ttctgtcatt gcagaaagtt ctaatgaaca gcactgatta gaccatataa gcacaggtat     300
gccctgtgac ccagcaatct tcagttcagg ttctcccaaa agcatatcct gaagccaaag     360
atgcaggtgg cttatttggg agctgtttcc cagaagcaca agcgagtggg gaaactgagc     420
caggaagagc aaaaagccaa taaatggtgc agagtctgga gtagagggag gcacctagag     480
cacttccctg actcagagtg agcacctcct taatttttgt ttgtttgttt gtttgttgag     540
acagagtctc actctgtcac ccaggctgga gtgctgtggc acaatctcgg ctcactgcag     600
cctccgcctc ccaggctcaa gcgattcctg tgactcagcc tcctgagtag ctgggtttac     660
aggcacatgc caccacaccc agctaatttt tgtattttta gtagagacag ggtttcacca     720
tgttggccag gctggtctcg aactcctggg ctcaggtgat ctgcccacct cggcctccca     780
aaatgctggg attacaggtg tgagccacca cgcctggccc cctgcttaaa ttttgactct     840
ggtcccctaa tttgacccac cctaattcca gcccccaaaa aggctactgc tgtgagcagc     900
tagaagtcat ttgttctggg acagtcaga agatcaagga gtcatgtaga agtcgcccga     960
gaattgaccc tccaagggaa agggaagctg cagtatttat tccattgctt tcagccctca    1020
ctgtttgagg actgctactg ggggaatcaa tcctgctact tccagtccat tctgcatgtg    1080
ggcagtagaa aggccttggt ctccagcaga gaagcagaaa gatccaagca cgtgaggcag    1140
gaaactgtca gcctgtgtgg gaactgacca ccatatccac aagccgaggg gatacagtag    1200
agggcatcag ctggtgtgct accgtatatt ccagaaagcc gcccacccag aggacaggtg    1260
tgagccttat ggtaatgggg agctagaggc aacctaagtg tccatcactg ggggaatagg    1320
taagtaaaag tgctgtggtt gtatacacca tgaaatacag tgcacaggaa acttgatgta    1380
cacagcttgt gaagagatct cagaagcagt gttaagttaa aaaataaaaa agaaagaagt    1440
agaagattta tagcacaatt ccacttatgt aaattggaaa cacatacaca cacgagatca    1500
caaattataa agatacatct ttgcagctat ttatcaagtg cattatagtg ggtgtctgtg    1560
ggggtgcgat gggaatggga attggcaatg gaggaataaa agccttggag ggtcttttcat   1620
gggccaattg tgatcctgtg ttatgatctg aagagtatga ttaataactt tctgcaccaa    1680
agggctaaga aaaaaaataa aggagtgaaa ataggaaatg tctgcacatc agagcagttt    1740
cttacctgct acacaattac tattactgca gggatgatga tagcaaggca accagactca    1800
ccgcctgcct tctctccagg cagccccctcc agtccccagg aaatgcgctt gcccccagcg    1860
aataaggagt tccctacccc tctcatgcta cccagaggga cagaaaggag aagtgggcct    1920
gctaccccca gaggttctca tcttctacct gggctgcata tggaataggg agcaagtaca    1980
taggactcat cataccccat ttctgcctct atcccactgt gggaccttag gcaagtcact    2040
ttgccttcct atgcctcagt tatctcacta gtaaaatggg catgattatt gtattagtca    2100
```

-continued

```
gggttctcca gagagacaga acaaatagga tgtttggata aatagatgat agatagagag    2160
atatagacta gatagatgag agagatagac tagatagaga gagagagaga gagagagaga    2220
gagagagact agatagatga gagagagata ggagggatt tattagggga attggctcag     2280
acaattaggg aggctaagaa gttccacaac aggccatctg caagctggag aaccaggaa     2340 gcttgtagtg cagctcagtt ccagaataaa agcctcagga cttaggggt agctagtgca     2400 agtcccagca ttttttttt ttctgagatg gagtctcact ctgttgacca ggctggagtg     2460
cagtgacatg atctcagctc actgcagcct ccgcctccag ggttcaagcg atactcctgc    2520
ctcagcctcc caagtagctg ggactacagg cctgtgccac cacgcctggc tgattttat     2580 attttagta gagatggggt ttcaccatgt tggccaggct ggtctcgaac tcctgacctc     2640
aagtgattca cctgcctcag cctcccaaac tgctgggatt acaggcgtga gccaccatgc    2700
ccagctgcac atcccagcat tcaaagacca aagagcctgg agttctgatg tttaagggca    2760
ggtgcagggt gtcccagctc ataagagaga gcaaattctc cttcctctg ccttttgtt      2820 ctattcaggc cctcggccaa ttggatggtg cccaccacat tgggtaacaa cgggtcttcc    2880
ttactcagtc cattgattca aatgccaatc tcttctggaa acaccccaga gtcatacca     2940 gaattaacgc atcaccagct atctgataaa cttaaccagt caaggtgaca cctaaaatta    3000
accatcacaa ttataaaaat aactactcag agaaacatta ggagcatgaa ctgaaattag    3060
ttaatgggac attcttaaac caatggcaga agctccttct tggccaggag cagtggctca    3120
tgcctttaat actagcactt tgcgaggctg aagcaggagg atggcttaag gccaggagtt    3180
caagactggc ctgggcaaca tagtgagacc cctatctcta caaaaataaa taaataaata    3240
ataaagtaag gtggtggctc acgcctgtaa tcccagcact ttgggaggcc aaggcaggca    3300
gatcatctga agtcaggagt tcgaagccag cgtgaccaac atagtaaaac ccagtctcta    3360
ctaaaaatac aaaaactagc caggcgtgat ggcatgcacc tgtaatccca actacttagg    3420
aggctgaggc aggagaatcg cttcaactcg ggaggcagaa gttgcagtga gccaagattg    3480
caccattgca ctccagcctg ggcaacaaga gcaaaactac gtctcaaaaa ataataataa    3540
caataaaata aaaaacaagc ttttttttt ttgaaacagg atctcactcc atcacccagg     3600
ctggagtgca gtggcacgat cttggctcac tgcaacctcc gcctcccggg ttcaagtgat    3660
tctcatgcct cggcctcctg agtagctgag accacaggcg catgccacca cacctggcta    3720
atttagaata aaaagaagc ttcctctctg ccactcaggt agccttatcc ctaatctcag     3780
cctccgtcag ggactccctg aggccagttg gctgaaagct gcccagggag ttctaaggat    3840
ttcagtttct ctttccttct tgatgcagct cccagctcac ttggccctgc ccacacctgt    3900
tccctcatca ggctcccaga cgggccccgc ccactcatgc ctcttaagtc aaagtggaaa    3960
ttctcatttc caattacctt ttcactttac acacatcatc ttggattgcc catttgcgt     4020 ggctaaaaag cagagccatg ccgctgggga agcagttgcg atttagcc                 4068
```

<210> SEQ ID NO 2
<211> LENGTH: 3418
<212> TYPE: DNA
<213> ORGANISM: Homo sapiens

<400> SEQUENCE: 2

```
ctgggtttac aggcacatgc caccacaccc agctaatttt tgtattttta gtagagacag      60
ggtttcacca tgttggccag gctggtctcg aactcctggg ctcaggtgat ctgcccacct     120
```

```
cggcctccca aaatgctggg attacaggtg tgagccacca cgcctggccc cctgcttaaa    180
ttttgactct ggtcccctaa tttgacccac cctaattcca gccccaaaa aggctactgc    240 tgtgagcagc tagaagtcat tgttctggg  acagtcaga agatcaagga gtcatgtaga    300
agtcgcccga gaattgaccc tccaagggaa agggaagctg cagtatttat tccattgctt    360
tcagccctca ctgtttgagg actgctactg ggggaatcaa tcctgctact ccagtccat    420 tctgcatgtg ggcagtagaa aggccttggt ctccagcaga gaagcagaaa gatccaagca    480
cgtgaggcag gaaactgtca gcctgtgtgg gaactgacca ccatatccac aagccgaggg    540
gatacagtag agggcatcag ctggtgtgct accgtatatt ccagaaagcc gcccacccag    600
aggacaggtg tgagccttat ggtaatgggg agctagaggc aacctaagtg tccatcactg    660
ggggaatagg taagtaaaag tgctgtggtt gtatacacca tgaaatacag tgcacaggaa    720
acttgatgta cacagcttgt gaagagatct cagaagcagt gttaagttaa aaataaaaaa    780
agaaagaagt agaagattta tagcacaatt ccacttatgt aaattggaaa cacatacaca    840
cacgagatca caaattataa agatacatct ttgcagctat ttatcaagtg cattatagtg    900
ggtgtctgtg ggggtgcgat gggaatggga attggcaatg gaggaataaa agccttggag    960 ggtcttttcat gggccaattg tgatcctgtg ttatgatctg aagagtatga ttaataactt   1020
tctgcaccaa agggctaaga aaaaaaataa aggagtgaaa ataggaaatg tctgcacatc   1080
agagcagttt cttacctgct acacaattac tattactgca gggatgatga tagcaaggca   1140
accagactca ccgcctgcct tctctccagg cagcccctcc agtccccagg aaatgcgctt   1200
gcccccagcg aataaggagt tccctacccc tctcatgcta cccagaggga cagaaaggag   1260
aagtgggcct gctaccccca gaggttctca tcttctacct gggctgcata tggaataggg   1320
agcaagtaca taggactcat catacccat  ttctgcctct atcccactgt gggaccttag   1380
gcaagtcact ttgccttcct atgcctcagt tatctcacta gtaaaatggg catgattatt   1440
gtattagtca gggttctcca gagagacaga acaaatagga tgtttggata aatagatgat   1500
agatagagag atatagacta gatagatgag agatatagac tagatagaga gagagagaga   1560
gagagagaga gagagagact agatagatga gagagagata ggagggatt tattagggga   1620 attggctcag acaattaggg aggctaagaa gttccacaac aggccatctg caagctggag   1680
aaccagggaa gcttgtagtg cagctcagtt ccagaataaa agcctcagga cttaggggt    1740 agctagtgca agtcccagca ttttttttt  ttctgagatg gagtctcact ctgttgacca   1800
ggctggagtg cagtgacatg atctcagctc actgcagcct ccgcctccag ggttcaagcg   1860
atactcctgc ctcagcctcc caagtagctg ggactacagg cctgtgccac cacgcctggc   1920 tgattttat  atttttagta gagatggggt ttcaccatgt tggccaggct ggtctcgaac   1980
tcctgacctc aagtgattca cctgcctcag cctcccaaac tgctgggatt acaggcgtga   2040
gccaccatgc ccagctgcac atcccagcat tcaaagacca aagagcctgg agttctgatg   2100
tttaagggca ggtgcagggt gtcccagctc ataagagaga gcaaattctc ctttcctctg   2160 ccttttgtt  ctattcaggc cctcggccaa ttggatggtg cccaccacat tgggtaacaa   2220
cgggtcttcc ttactcagtc cattgattca aatgccaatc tcttctggaa acacccaga    2280 gtcataccca gaattaacgc atcaccagct atctgataaa cttaccagt caaggtgaca    2340 cctaaaatta accatcacaa ttataaaaat aactactcag agaaacatta ggagcatgaa   2400
ctgaaattag ttaatgggac attcttaaac caatggcaga agctccttct tggccaggag   2460
cagtggctca tgcctttaat actagcactt tgcgaggctg aagcaggagg atggcttaag   2520
```

```
gccaggagtt caagactggc ctgggcaaca tagtgagacc cctatctcta caaaaataaa   2580
taaataaata ataaagtaag gtggtggctc acgcctgtaa tcccagcact ttgggaggcc   2640
aaggcaggca gatcatctga agtcaggagt tcgaagccag cgtgaccaac atagtaaaac   2700
ccagtctcta ctaaaaatac aaaaactagc caggcgtgat ggcatgcacc tgtaatccca   2760
actacttagg aggctgaggc aggagaatcg cttcaactcg ggaggcagaa gttgcagtga   2820
gccaagattg caccattgca ctccagcctg ggcaacaaga gcaaaactac gtctcaaaaa   2880
ataataataa caataaaata aaaaacaagc ttttttttt ttgaaacagg atctcactcc    2940
atcacccagg ctggagtgca gtggcacgat cttggctcac tgcaacctcc gcctcccggg   3000
ttcaagtgat tctcatgcct cggcctcctg agtagctgag accacaggcg catgccacca   3060
cacctggcta atttagaata aaaagaagc ttcctctctg ccactcaggt agccttatcc    3120
ctaatctcag cctccgtcag ggactccctg aggccagttg gctgaaagct gcccagggag   3180
ttctaaggat ttcagtttct ctttccttct tgatgcagct cccagctcac ttggccctgc   3240
ccacacctgt tccctcatca ggctcccaga cgggccccgc ccactcatgc ctcttaagtc   3300
aaagtggaaa ttctcatttc caattacctt ttcactttac acacatcatc ttggattgcc   3360
cattttgcgt ggctaaaaag cagagccatg ccgctgggga agcagttgcg atttagcc    3418

<210> SEQ ID NO 3
<211> LENGTH: 2112
<212> TYPE: DNA
<213> ORGANISM: Homo sapiens

<400> SEQUENCE: 3
catatggaat agggagcaag tacataggac tcatcatacc ccatttctgc ctctatccca     60
ctgtgggacc ttaggcaagt cactttgcct tcctatgcct cagttatctc actagtaaaa    120
tgggcatgat tattgtatta gtcagggttc tccagagaga cagaacaaat aggatgtttg    180
gataaataga tgatagatag agagatatag actagataga tgagagagat agactagata    240
gagagagaga gagagagaga gagagagaga gactagatag atgagagaga gataggaggg    300
gatttattag gggaattggc tcagacaatt agggaggcta agaagttcca caacaggcca    360
tctgcaagct ggagaaccag ggaagcttgt agtgcagctc agttccagaa taaaagcctc    420
aggacttagg gggtagctag tgcaagtccc agcatttttt ttttttctga gatggagtct    480
cactctgttg accaggctgg agtgcagtga catgatctca gctcactgca gcctccgcct    540
ccagggttca gcgatactc ctgcctcagc ctcccaagta gctgggacta caggcctgtg     600
ccaccacgcc tggctgattt ttatatttt agtagagatg gggtttcacc atgttggcca     660
ggctggtctc gaactcctga cctcaagtga ttcacctgcc tcagcctccc aaactgctgg    720
gattacaggc gtgagccacc atgcccagct gcacatccca gcattcaaag accaaagagc    780
ctggagttct gatgtttaag ggcaggtgca gggtgtccca gctcataaga gagagcaaat    840
tctcctttcc tctgcctttt tgttctattc aggccctcgg ccaattggat ggtgcccacc    900
acattgggta acaacgggtc ttccttactc agtccattga ttcaaatgcc aatctcttct    960
ggaaacaccc cagagtcata cccagaatta acgcatcacc agctatctga taaacttaac   1020
cagtcaaggt gacacctaaa attaaccatc acaattataa aaataactac tcagagaaac   1080
attaggagca tgaactgaaa ttagttaatg ggacattctt aaaccaatgg cagaagctcc   1140
ttcttggcca ggagcagtgg ctcatgcctt taatactagc actttgcgag gctgaagcag   1200
```

```
gaggatggct taaggccagg agttcaagac tggcctgggc aacatagtga gaccccctatc    1260 tctacaaaaa taaataaata aataataaag taaggtggtg gctcacgcct gtaatcccag    1320
cactttggga ggccaaggca ggcagatcat ctgaagtcag gagttcgaag ccagcgtgac    1380
caacatagta aaacccagtc tctactaaaa atacaaaaac tagccaggcg tgatggcatg    1440
cacctgtaat cccaactact taggaggctg aggcaggaga atcgcttcaa ctcgggaggc    1500
agaagttgca gtgagccaag attgcaccat tgcactccag cctgggcaac aagagcaaaa    1560
ctacgtctca aaaataata ataacaataa aataaaaaac aagcttttt tttttttgaaa     1620 caggatctca ctccatcacc caggctggag tgcagtggca cgatcttggc tcactgcaac    1680
ctccgcctcc cgggttcaag tgattctcat gcctcggcct cctgagtagc tgagaccaca    1740
ggcgcatgcc accacacctg gctaatttag aataaaaaag aagcttcctc tctgccactc    1800
aggtagcctt atccctaatc tcagcctccg tcagggactc cctgaggcca gttggctgaa    1860
agctgcccag ggagttctaa ggatttcagt ttctctttcc ttcttgatgc agctcccagc    1920
tcacttggcc ctgcccacac ctgttccctc atcaggctcc cagacgggcc ccgcccactc    1980
atgcctctta agtcaaagtg gaaattctca tttccaatta ccttttcact ttacacacat    2040
catcttggat tgcccatttt gcgtggctaa aaagcagagc catgccgctg gggaagcagt    2100
tgcgatttag cc                                                        2112

<210> SEQ ID NO 4
<211> LENGTH: 1755
<212> TYPE: DNA
<213> ORGANISM: Homo sapiens

<400> SEQUENCE: 4
ccatctgcaa gctggagaac cagggaagct tgtagtgcag ctcagttcca gaataaaagc      60
ctcaggactt aggggtagc tagtgcaagt cccagcattt ttttttttc tgagatggag        120 tctcactctg ttgaccaggc tggagtgcag tgacatgatc tcagctcact gcagcctccg      180
cctccagggt tcaagcgata tcctgcctc agcctcccaa gtagctggga ctacaggcct      240
gtgccaccac gcctggctga ttttatatt tttagtagag atggggtttc accatgttgg      300
ccaggctggt ctcgaactcc tgacctcaag tgattcacct gcctcagcct cccaaactgc     360
tgggattaca ggcgtgagcc accatgccca gctgcacatc ccagcattca aagaccaaag     420
agcctggagt tctgatgttt aagggcaggt gcagggtgtc ccagctcata agagagagca     480
aattctcctt tcctctgcct ttttgttcta ttcaggccct cggccaattg atggtgccc      540 accacattgg gtaacaacgg gtcttcctta ctcagtccat tgattcaaat gccaatctct     600
tctggaaaca cccagagtc atacccagaa ttaacgcatc accagctatc tgataaactt      660
aaccagtcaa ggtgacacct aaaattaacc atcacaatta taaaaataac tactcagaga    720
aacattagga gcatgaactg aaattagtta atgggacatt cttaaaccaa tggcagaagc    780
tccttcttgg ccaggagcag tggctcatgc ctttaatact agcactttgc gaggctgaag    840
caggaggatg gcttaaggcc aggagttcaa gactggcctg gcaacatag tgagacccct     900 atctctacaa aaataataa ataataata agtaaggtg gtggctcacg cctgtaatcc       960
cagcactttg ggaggccaag gcaggcagat catctgaagt caggagttcg aagccagcgt   1020
gaccaacata gtaaaaccca gtctctacta aaatacaaaa actagccag gcgtgatggc    1080 atgcacctgt aatcccaact acttaggagg ctgaggcagg agaatcgctt caactcggga   1140
ggcagaagtt gcagtgagcc aagattgcac cattgcactc cagcctgggc aacaagagca   1200
```

| | | | |
|---|---|---|---|
| aaactacgtc | tcaaaaaata | ataataacaa | taaaataaaa | aacaagcttt | tttttttttg | 1260 |
| aaacaggatc | tcactccatc | acccaggctg | gagtgcagtg | gcacgatctt | ggctcactgc | 1320 |
| aacctccgcc | tcccggttc | aagtgattct | catgcctcgg | cctcctgagt | agctgagacc | 1380 |
| acaggcgcat | gccaccacac | ctggctaatt | tagaataaaa | aagaagcttc | ctctctgcca | 1440 |
| ctcaggtagc | cttatcccta | atctcagcct | ccgtcaggga | ctccctgagg | ccagttggct | 1500 |
| gaaagctgcc | cagggagttc | taaggatttc | agtttctctt | tccttcttga | tgcagctccc | 1560 |
| agctcacttg | gccctgccca | cacctgttcc | ctcatcaggc | tcccagacgg | gccccgccca | 1620 |
| ctcatgcctc | ttaagtcaaa | gtggaaattc | tcatttccaa | ttacctttc | actttacaca | 1680 |
| catcatcttg | gattgcccat | tttgcgtggc | taaaaagcag | agccatgccg | ctggggaagc | 1740 |
| agttgcgatt | tagcc | | | | | 1755 |

<210> SEQ ID NO 5
<211> LENGTH: 1521
<212> TYPE: DNA
<213> ORGANISM: Homo sapiens

<400> SEQUENCE: 5

| | | | | | | |
|---|---|---|---|---|---|---|
| aggcctgtgc | caccacgcct | ggctgatttt | tatatttta | gtagagatgg | ggtttcacca | 60 |
| tgttggccag | gctggtctcg | aactcctgac | ctcaagtgat | tcacctgcct | cagcctccca | 120 |
| aactgctggg | attacaggcg | tgagccacca | tgcccagctg | cacatcccag | cattcaaaga | 180 |
| ccaaagagcc | tggagttctg | atgtttaagg | gcaggtgcag | ggtgtcccag | ctcataagag | 240 |
| agagcaaatt | ctcctttcct | ctgccttttt | gttctattca | ggccctcggc | caattggatg | 300 |
| gtgcccacca | cattgggtaa | caacgggtct | tccttactca | gtccattgat | tcaaatgcca | 360 |
| atctcttctg | gaaacacccc | agagtcatac | ccagaattaa | cgcatcacca | gctatctgat | 420 |
| aaacttaacc | agtcaaggtg | acacctaaaa | ttaaccatca | caattataaa | aataactact | 480 |
| cagagaaaca | ttaggagcat | gaactgaaat | tagttaatgg | gacattctta | aaccaatggc | 540 |
| agaagctcct | tcttggccag | gagcagtggc | tcatgccttt | aatactagca | ctttgcgagg | 600 |
| ctgaagcagg | aggatggctt | aaggccagga | gttcaagact | ggcctgggca | acatagtgag | 660 |
| accctatct | ctacaaaaat | aaataaataa | ataataaagt | aaggtggtgg | ctcacgcctg | 720 |
| taatcccagc | actttgggag | gccaaggcag | gcagatcatc | tgaagtcagg | agttcgaagc | 780 |
| cagcgtgacc | aacatagtaa | aacccagtct | ctactaaaaa | tacaaaaact | agccaggcgt | 840 |
| gatggcatgc | acctgtaatc | ccaactactt | aggaggctga | ggcaggagaa | tcgcttcaac | 900 |
| tcgggaggca | gaagttgcag | tgagccaaga | ttgcaccatt | gcactccagc | ctgggcaaca | 960 |
| agagcaaaac | tacgtctcaa | aaaataataa | taacaataaa | ataaaaaaca | agcttttttt | 1020 |
| ttttgaaac | aggatctcac | tccatcaccc | aggctggagt | gcagtggcac | gatcttggct | 1080 |
| cactgcaacc | tccgcctccc | gggttcaagt | gattctcatg | cctcggcctc | ctgagtagct | 1140 |
| gagaccacag | gcgcatgcca | ccacacctgg | ctaatttaga | ataaaaaga | agcttcctct | 1200 |
| ctgccactca | ggtagcctta | tccctaatct | cagcctccgt | cagggactcc | ctgaggccag | 1260 |
| ttggctgaaa | gctgccagg | gagttctaag | gatttcagtt | tctcttcct | tcttgatgca | 1320 |
| gctcccagct | cacttggccc | tgccacacc | tgttccctca | tcaggctccc | agacgggccc | 1380 |
| cgccactca | tgcctcttaa | gtcaaagtgg | aaattctcat | ttccaattac | cttttcactt | 1440 |
| tacacacatc | atcttggatt | gcccattttg | cgtggctaaa | aagcagagcc | atgccgctgg | 1500 | ggaagcagtt gcgatttagc c                                                 1521

<210> SEQ ID NO 6
<211> LENGTH: 1195
<212> TYPE: DNA
<213> ORGANISM: Homo sapiens

<400> SEQUENCE: 6
gtcttcctta ctcagtccat tgattcaaat gccaatctct tctggaaaca ccccagagtc        60
atacccagaa ttaacgcatc accagctatc tgataaactt aaccagtcaa ggtgacacct       120
aaaattaacc atcacaatta taaaaataac tactcagaga acattaggaa gcatgaactg       180
aaattagtta atgggacatt cttaaaccaa tggcagaagc tccttcttgg ccaggagcag       240
tggctcatgc ctttaatact agcactttgc gaggctgaag caggaggatg cttaaggcc        300
aggagttcaa gactggcctg gcaacatag tgagacccct atctctacaa aaataaataa        360
ataaataata agtaaggtg gtggctcacg cctgtaatcc cagcactttg ggaggccaag        420
gcaggcagat catctgaagt caggagttcg aagccagcgt gaccaacata gtaaaaccca       480
gtctctacta aaaatacaaa aactagccag gcgtgatggc atgcacctgt aatcccaact       540
acttaggagg ctgaggcagg agaatcgctt caactcggga ggcagaagtt gcagtgagcc       600
aagattgcac cattgcactc cagcctgggc aacaagagca aaactacgtc tcaaaaaata       660
ataataacaa taaaataaaa aacaagcttt tttttttttg aaacaggatc tcactccatc       720
acccaggctg gagtgcagtg gcacgatctt ggctcactgc aacctccgcc tcccgggttc       780
aagtgattct catgcctcgg cctcctgagt agctgagacc acaggcgcat gccaccacac       840
ctggctaatt tagaataaaa agaagcttc ctctctgcca ctcaggtagc cttatcccta       900
atctcagcct ccgtcaggga ctccctgagg ccagttggct gaaagctgcc cagggagttc       960
taaggatttc agtttctctt tccttcttga tgcagctccc agctcacttg ccctgccca       1020
cacctgttcc ctcatcaggc tcccagacgg ccccgccca ctcatgcctc ttaagtcaaa      1080
gtggaaattc tcatttccaa ttacctttc actttacaca catcatcttg gattgcccat       1140
tttgcgtggc taaaaagcag agccatgccg ctgggaagc agttgcgatt tagcc           1195

<210> SEQ ID NO 7
<211> LENGTH: 630
<212> TYPE: DNA
<213> ORGANISM: Homo sapiens

<400> SEQUENCE: 7
cgcttcaact cgggaggcag aagttgcagt gagccaagat tgcaccattg cactccagcc        60
tgggcaacaa gagcaaaact acgtctcaaa aataataat aacaataaaa taaaaaacaa       120
gctttttttt ttttgaaaca ggatctcact ccatcaccca ggctggagtg cagtggcacg       180
atcttggctc actgcaacct ccgcctcccg ggttcaagtg attctcatgc ctcggcctcc       240
tgagtagctg agaccacagg cgcatgccac cacacctggc taatttagaa taaaaagaa       300
gcttcctctc tgccactcag gtagccttat ccctaatctc agcctccgtc agggactccc       360
tgaggccagt tggctgaaag ctgcccaggg agttctaagg atttcagttt ctctttcctt       420
cttgatgcag ctcccagctc acttggccct gcccacacct gttccctcat caggctccca       480
gacgggcccc gcccactcat gcctcttaag tcaaagtgga aattctcatt tccaattacc       540
ttttcacttt acacacatca tcttggattg cccattttgc gtggctaaaa agcagagcca       600
tgccgctggg aagcagttg cgatttagcc                                         630

```
<210> SEQ ID NO 8
<211> LENGTH: 19
<212> TYPE: RNA
<213> ORGANISM: Homo sapiens
<220> FEATURE:
<221> NAME/KEY: siRNA
<222> LOCATION: (1)..(19)

<400> SEQUENCE: 8
ccgaaucaau gaagaaauc                                              19

<210> SEQ ID NO 9
<211> LENGTH: 19
<212> TYPE: RNA
<213> ORGANISM: Artificial
<220> FEATURE:
<223> OTHER INFORMATION: siRNA

<400> SEQUENCE: 9
gagaguacag cgugaaaga                                              19

<210> SEQ ID NO 10
<211> LENGTH: 19
<212> TYPE: RNA
<213> ORGANISM: Artificial
<220> FEATURE:
<223> OTHER INFORMATION: siRNA

<400> SEQUENCE: 10
gcaacuggau gcgcuaugu                                              19

<210> SEQ ID NO 11
<211> LENGTH: 19
<212> TYPE: RNA
<213> ORGANISM: Artificial
<220> FEATURE:
<223> OTHER INFORMATION: siRNA

<400> SEQUENCE: 11
ccucuaccgu ucuaacauu                                              19

<210> SEQ ID NO 12
<211> LENGTH: 19
<212> TYPE: RNA
<213> ORGANISM: Artificial
<220> FEATURE:
<223> OTHER INFORMATION: siRNA

<400> SEQUENCE: 12
cuguaagaga gaagcggaa                                              19

<210> SEQ ID NO 13
<211> LENGTH: 19
<212> TYPE: RNA
<213> ORGANISM: Artificial
<220> FEATURE:
<223> OTHER INFORMATION: siRNA

<400> SEQUENCE: 13
cugaaauccu cucgaauga                                              19

<210> SEQ ID NO 14
<211> LENGTH: 19
<212> TYPE: RNA
<213> ORGANISM: Artificial
```

```
<220> FEATURE:
<223> OTHER INFORMATION: siRNA

<400> SEQUENCE: 14
gcgcaauaac guuacaaau                                              19

<210> SEQ ID NO 15
<211> LENGTH: 19
<212> TYPE: RNA
<213> ORGANISM: Artificial
<220> FEATURE:
<223> OTHER INFORMATION: siRNA

<400> SEQUENCE: 15
gcaacaggga gaauuauua                                              19

<210> SEQ ID NO 16
<211> LENGTH: 23
<212> TYPE: DNA
<213> ORGANISM: Homo sapiens

<400> SEQUENCE: 16
gctacagtat tgccagcata tag                                         23

<210> SEQ ID NO 17
<211> LENGTH: 20
<212> TYPE: DNA
<213> ORGANISM: Homo sapiens

<400> SEQUENCE: 17
ggctaaatcg caactgcttc                                             20

<210> SEQ ID NO 18
<211> LENGTH: 20
<212> TYPE: DNA
<213> ORGANISM: Homo sapiens

<400> SEQUENCE: 18
cttccaagcc caccccaact                                             20

<210> SEQ ID NO 19
<211> LENGTH: 19
<212> TYPE: DNA
<213> ORGANISM: Homo sapiens

<400> SEQUENCE: 19
ggcctccagg accttcagc                                              19

<210> SEQ ID NO 20
<211> LENGTH: 25
<212> TYPE: DNA
<213> ORGANISM: Homo sapiens

<400> SEQUENCE: 20
gcaagacgtt cagtcctgtg gataa                                       25

<210> SEQ ID NO 21
<211> LENGTH: 22
<212> TYPE: DNA
<213> ORGANISM: Homo sapiens

<400> SEQUENCE: 21
cagccctggc gtcgtgatta gt                                          22
```

```
<210> SEQ ID NO 22
<211> LENGTH: 20
<212> TYPE: DNA
<213> ORGANISM: Homo sapiens

<400> SEQUENCE: 22
ctctgccaat ccctgaaacc                                              20

<210> SEQ ID NO 23
<211> LENGTH: 22
<212> TYPE: DNA
<213> ORGANISM: Homo sapiens

<400> SEQUENCE: 23
tggactgggt agagatgaac ga                                           22

<210> SEQ ID NO 24
<211> LENGTH: 19
<212> TYPE: DNA
<213> ORGANISM: Homo sapiens

<400> SEQUENCE: 24
tgcaccacca cctgcttag                                               19

<210> SEQ ID NO 25
<211> LENGTH: 19
<212> TYPE: DNA
<213> ORGANISM: Homo sapiens

<400> SEQUENCE: 25
ggatgcaggg atgatgttc                                               19

<210> SEQ ID NO 26
<211> LENGTH: 20
<212> TYPE: DNA
<213> ORGANISM: Homo sapiens

<400> SEQUENCE: 26
gcacctgaag aggaccagag                                              20

<210> SEQ ID NO 27
<211> LENGTH: 23
<212> TYPE: DNA
<213> ORGANISM: Homo sapiens

<400> SEQUENCE: 27
gcctctatca caatatggac agg                                          23

<210> SEQ ID NO 28
<211> LENGTH: 22
<212> TYPE: DNA
<213> ORGANISM: Homo sapiens

<400> SEQUENCE: 28
tctcgaactc ctgacctcaa gt                                           22

<210> SEQ ID NO 29
<211> LENGTH: 22
<212> TYPE: DNA
<213> ORGANISM: Homo sapiens

<400> SEQUENCE: 29
ctctcttatg agctgggaca cc                                           22
```

<210> SEQ ID NO 30
<211> LENGTH: 20
<212> TYPE: DNA
<213> ORGANISM: Homo sapiens

<400> SEQUENCE: 30
gaggctacag tattgccagc        20

<210> SEQ ID NO 31
<211> LENGTH: 19
<212> TYPE: DNA
<213> ORGANISM: Homo sapiens

<400> SEQUENCE: 31
cctgcatctt tggcttcag        19

<210> SEQ ID NO 32
<211> LENGTH: 21
<212> TYPE: DNA
<213> ORGANISM: Homo sapiens

<400> SEQUENCE: 32
gaaacaggat ctcactccat c        21

<210> SEQ ID NO 33
<211> LENGTH: 18
<212> TYPE: DNA
<213> ORGANISM: Homo sapiens

<400> SEQUENCE: 33
tcagccaact ggcctcag        18

<210> SEQ ID NO 34
<211> LENGTH: 18
<212> TYPE: DNA
<213> ORGANISM: Homo sapiens

<400> SEQUENCE: 34
cctgaggcca gttggctg        18

<210> SEQ ID NO 35
<211> LENGTH: 21
<212> TYPE: DNA
<213> ORGANISM: Homo sapiens

<400> SEQUENCE: 35
aatgggcaat ccaagatgat g        21

<210> SEQ ID NO 36
<211> LENGTH: 21
<212> TYPE: DNA
<213> ORGANISM: Homo sapiens

<400> SEQUENCE: 36
acattgggta acaacgggtc t        21

<210> SEQ ID NO 37
<211> LENGTH: 21
<212> TYPE: DNA
<213> ORGANISM: Homo sapiens

<400> SEQUENCE: 37

```
gctggtgatg cgttaattct g                                               21

<210> SEQ ID NO 38
<211> LENGTH: 20
<212> TYPE: DNA
<213> ORGANISM: Homo sapiens

<400> SEQUENCE: 38
cctaatctca gcctccgtca                                                 20

<210> SEQ ID NO 39
<211> LENGTH: 20
<212> TYPE: DNA
<213> ORGANISM: Homo sapiens

<400> SEQUENCE: 39
ctgggagctg catcaagaag                                                 20

<210> SEQ ID NO 40
<211> LENGTH: 19
<212> TYPE: RNA
<213> ORGANISM: Artificial
<220> FEATURE:
<223> OTHER INFORMATION: siRNA

<400> SEQUENCE: 40
ggagacaucc uuccgcaaa                                                  19

<210> SEQ ID NO 41
<211> LENGTH: 19
<212> TYPE: RNA
<213> ORGANISM: Artificial
<220> FEATURE:
<223> OTHER INFORMATION: siRNA

<400> SEQUENCE: 41
gaugggaucu gcacuguaa                                                  19

<210> SEQ ID NO 42
<211> LENGTH: 19
<212> TYPE: RNA
<213> ORGANISM: Artificial
<220> FEATURE:
<223> OTHER INFORMATION: siRNA

<400> SEQUENCE: 42
gaaauuaggu cuggggaua                                                  19

<210> SEQ ID NO 43
<211> LENGTH: 19
<212> TYPE: RNA
<213> ORGANISM: Artificial
<220> FEATURE:
<223> OTHER INFORMATION: siRNA

<400> SEQUENCE: 43
gcaggaagga ccucuagaa                                                  19

<210> SEQ ID NO 44
<211> LENGTH: 19
<212> TYPE: RNA
<213> ORGANISM: Artificial
<220> FEATURE:
<223> OTHER INFORMATION: siRNA

<400> SEQUENCE: 44
```

```
ggauugagga gaaacguaa                                                19

<210> SEQ ID NO 45
<211> LENGTH: 20
<212> TYPE: RNA
<213> ORGANISM: Artificial
<220> FEATURE:
<223> OTHER INFORMATION: siRNA

<400> SEQUENCE: 45
cccacgagcu uguaggaaaa                                               20

<210> SEQ ID NO 46
<211> LENGTH: 19
<212> TYPE: RNA
<213> ORGANISM: Artificial
<220> FEATURE:
<223> OTHER INFORMATION: siRNA

<400> SEQUENCE: 46
ggcuauaacu cgccuagug                                                19

<210> SEQ ID NO 47
<211> LENGTH: 19
<212> TYPE: RNA
<213> ORGANISM: Artificial
<220> FEATURE:
<223> OTHER INFORMATION: siRNA

<400> SEQUENCE: 47
ccacacaacu gagcccaug                                                19

<210> SEQ ID NO 48
<211> LENGTH: 19
<212> TYPE: RNA
<213> ORGANISM: Artificial
<220> FEATURE:
<223> OTHER INFORMATION: siRNA

<400> SEQUENCE: 48
gcccgucuau gacaagaaa                                                19

<210> SEQ ID NO 49
<211> LENGTH: 19
<212> TYPE: RNA
<213> ORGANISM: Artificial
<220> FEATURE:
<223> OTHER INFORMATION: siRNA

<400> SEQUENCE: 49
ccauugagcg gaagauuca                                                19

<210> SEQ ID NO 50
<211> LENGTH: 19
<212> TYPE: RNA
<213> ORGANISM: Artificial
<220> FEATURE:
<223> OTHER INFORMATION: siRNA

<400> SEQUENCE: 50
gcacagauga auuggagau                                                19

<210> SEQ ID NO 51
<211> LENGTH: 19
<212> TYPE: RNA
```

<213> ORGANISM: Artificial
<220> FEATURE:
<223> OTHER INFORMATION: siRNA

<400> SEQUENCE: 51
cugcggauuu gccgaauua                                           19

<210> SEQ ID NO 52
<211> LENGTH: 19
<212> TYPE: RNA
<213> ORGANISM: Artificial
<220> FEATURE:
<223> OTHER INFORMATION: siRNA

<400> SEQUENCE: 52
ggacaggcca cuaccuaug                                           19

<210> SEQ ID NO 53
<211> LENGTH: 19
<212> TYPE: RNA
<213> ORGANISM: Artificial
<220> FEATURE:
<223> OTHER INFORMATION: siRNA

<400> SEQUENCE: 53
acgcagaggc cuacagaca                                           19

<210> SEQ ID NO 54
<211> LENGTH: 19
<212> TYPE: RNA
<213> ORGANISM: Artificial
<220> FEATURE:
<223> OTHER INFORMATION: siRNA

<400> SEQUENCE: 54
gcugguggcu uuauggugg                                           19

<210> SEQ ID NO 55
<211> LENGTH: 19
<212> TYPE: RNA
<213> ORGANISM: Artificial
<220> FEATURE:
<223> OTHER INFORMATION: siRNA

<400> SEQUENCE: 55
ccaagaagcg ccugauugu                                           19

<210> SEQ ID NO 56
<211> LENGTH: 19
<212> TYPE: RNA
<213> ORGANISM: Artificial
<220> FEATURE:
<223> OTHER INFORMATION: siRNA

<400> SEQUENCE: 56
gauaaaacgu ccaugguua                                           19

<210> SEQ ID NO 57
<211> LENGTH: 19
<212> TYPE: RNA
<213> ORGANISM: Artificial
<220> FEATURE:
<223> OTHER INFORMATION: siRNA

<400> SEQUENCE: 57
gaaccaguga caaguaauu                                           19

-continued

<210> SEQ ID NO 58
<211> LENGTH: 19
<212> TYPE: RNA
<213> ORGANISM: Artificial
<220> FEATURE:
<223> OTHER INFORMATION: siRNA

<400> SEQUENCE: 58
aagaugaggu guuguuaga                                                19

<210> SEQ ID NO 59
<211> LENGTH: 19
<212> TYPE: RNA
<213> ORGANISM: Artificial
<220> FEATURE:
<223> OTHER INFORMATION: siRNA

<400> SEQUENCE: 59
gauagagacu ugagaucgu                                                19

<210> SEQ ID NO 60
<211> LENGTH: 19
<212> TYPE: RNA
<213> ORGANISM: Artificial
<220> FEATURE:
<223> OTHER INFORMATION: siRNA

<400> SEQUENCE: 60
ggaaguuuca gaucuugua                                                19

<210> SEQ ID NO 61
<211> LENGTH: 19
<212> TYPE: RNA
<213> ORGANISM: Artificial
<220> FEATURE:
<223> OTHER INFORMATION: siRNA

<400> SEQUENCE: 61
ggucuccgag cuccuauuu                                                19

<210> SEQ ID NO 62
<211> LENGTH: 19
<212> TYPE: RNA
<213> ORGANISM: Artificial
<220> FEATURE:
<223> OTHER INFORMATION: siRNA

<400> SEQUENCE: 62
gugaggaggu ggcucugaa                                                19

<210> SEQ ID NO 63
<211> LENGTH: 19
<212> TYPE: RNA
<213> ORGANISM: Artificial
<220> FEATURE:
<223> OTHER INFORMATION: siRNA

<400> SEQUENCE: 63
ccaagacccu ccacagaug                                                19

<210> SEQ ID NO 64
<211> LENGTH: 19
<212> TYPE: RNA
<213> ORGANISM: Artificial
<220> FEATURE:

<223> OTHER INFORMATION: siRNA

<400> SEQUENCE: 64
caucgacggu caaggcaac                                                  19

<210> SEQ ID NO 65
<211> LENGTH: 19
<212> TYPE: RNA
<213> ORGANISM: Artificial
<220> FEATURE:
<223> OTHER INFORMATION: siRNA

<400> SEQUENCE: 65
gaaggcaucc agaccagaa                                                  19

<210> SEQ ID NO 66
<211> LENGTH: 19
<212> TYPE: RNA
<213> ORGANISM: Artificial
<220> FEATURE:
<223> OTHER INFORMATION: siRNA

<400> SEQUENCE: 66
cccaagaaca gcucguuua                                                  19

<210> SEQ ID NO 67
<211> LENGTH: 19
<212> TYPE: RNA
<213> ORGANISM: Artificial
<220> FEATURE:
<223> OTHER INFORMATION: siRNA

<400> SEQUENCE: 67
guacagcucc ggacucuuc                                                  19

<210> SEQ ID NO 68
<211> LENGTH: 23
<212> TYPE: DNA
<213> ORGANISM: Homo sapiens

<400> SEQUENCE: 68 cagcaattttt cagtgtcaga agc                                            23

<210> SEQ ID NO 69
<211> LENGTH: 21
<212> TYPE: DNA
<213> ORGANISM: Homo sapiens

<400> SEQUENCE: 69
tcatcctgtc cttgaggcag t                                               21

<210> SEQ ID NO 70
<211> LENGTH: 20
<212> TYPE: DNA
<213> ORGANISM: Homo sapiens

<400> SEQUENCE: 70
aactgcttcc gacaatcaac                                                 20

<210> SEQ ID NO 71
<211> LENGTH: 19
<212> TYPE: DNA
<213> ORGANISM: Homo sapiens

```
<400> SEQUENCE: 71
cctccttctc cctccaaaa                                                                    19
```

REPRESSOR ON IFN-λ PROMOTER AND SIRNA AGAINST GATA1, EVI1, AND CRX TO ALTER IFN-λ GENE ACTIVITY

CROSS-REFERENCE TO RELATED APPLICATIONS

The present application is a Continuation of U.S. application Ser. No. 13/771,855, filed Feb. 20, 2013, which is a Continuation-In-Part of U.S. Pat. No. 8,802,648 filed Dec. 4, 2012, which is a Divisional of U.S. Pat. No. 8,349,808, filed May 5, 2010, which claims the benefit of priority under 35 U.S.C. §119(e) to U.S. Provisional Application No. 61/215,428 filed May 5, 2009, the entire disclosures of which are hereby incorporated by reference in their entirety.

FIELD OF THE INVENTION

The present invention relates generally to the identification of a novel repressor on IFN-λ1 promoter located between ~1.2 kb and ~1.6 kb from the IFN-λ1 translation start site, and a method of using siRNA to regulate IFN-λ gene promoter activity. Specifically, the present invention relates to the compositions and methods of using siRNA against ZEB1 to reduce their binding to the novel repressor on the IFN-λ gene promoter in order to increase IFN-λ1 gene activity. Also, the present invention is directed to the compositions and methods of using siRNA against BLIMP-1 to reduce their binding to IFN-λ gene promoter independent of the repressor region in order to increase IFN-λ1 gene activity.

BACKGROUND OF THE INVENTION

Interferon is a class of immunomodulators that possess an anti-viral activity. Based on their functions and protein structures, there are three types of interferons (type I, type II and type III). Type-III interferon family comprises three members; namely, IFN-λ1, IFN-λ2 and IFN-λ3 that share a high degree of homology. Type-III IFNs represent the most recently identified interferons (Sheppard et al., 2003; Kotenko et al., 2003); therefore, many aspects of their regulation and function are unclear. IFN-λ proteins are encoded by three separate respective IFN-λ genes, which are all located on chromosome 19q13. The genomic nucleotide sequences upstream from the start codon for IFN-λ1, IFN-λ2 and IFN-λ3 have been reported. However, the regulatory elements of these genomic upstream structures have not been defined. The high sequence homology (~95%) between the IFN-λ2 and IFN-λ3 upstream regions render the regulatory study for these promoters difficult. IFN-λ1 has a relatively diverse sequence (~70%) compared to IFN-λ2 and IFN-λ3 promoters, but attempts in characterizing the regulatory elements of the IFN-λ1 promoter has met only limited success.

Several research groups have examined the IFN-λ1 promoter. Despite these efforts, the regulation of the IFN-λ1 promoter is far from clear; let alone the structural organization and the role of transcription sites in the IFN-λ1 promoter. Onoguchi et al. identified a ~600 bp upstream region containing one (1) NF-κB and three (3) IRF sites that activates IFN-λ1 gene expression in murine fibrosarcoma cells in response to NewCastle disease virus stimulation (Onoguchi et al., 2007). In a similar vein, Osterlund et al. showed that transfection of human embryonic kidney cells with plasmids encoding NF-κB or IRF protein increases IFN-λ1 reporter gene activity (Osterlund et al., 2007). Thomson et al. examined a further upstream region (~1.1 kb from the IFN-λ1 translation start codon) and discovered three (3) additional NF-κB sites. Using siRNA, this group showed a role of NF-κB in activation of IFN-λ1 gene expression in response to bacterial stimulation (Thomson et al., 2009). Given that IFN-λ1 is not constitutively expressed in human but induced following viral/bacterial stimulation, it is possible that there exists a repressor mechanism (yet to be uncovered) that keeps the IFN-λ1 expression at bay. To the best of the inventors' knowledge, there is simply no scientific support for this contention.

Accordingly, there is a continuing need in defining the regulatory elements of IFN-λ1 promoter and means to regulate the IFN-λ1 promoter activity. The present invention cures the deficiency of these prior art. The present inventors surprisingly discovered a novel repressor region between (~1.2 kb and ~1.6 kb from the IFN-λ1 translation start site) in the IFN-λ1 gene, and provide a novel means to regulate the IFN-λ1 promoter activity using siRNA against specific regions (BLIMP-1 and ZEB1) of the repressor. The present invention has practical utility in the treatment of viral infection and asthma.

Other features and advantages of the invention will be apparent from the following description of the embodiments discussed in the detailed description, and from the claims.

SUMMARY OF THE INVENTION

In one aspect, the present invention provides a siRNA oligonucleotide 15-30 nucleobases in length targeted against a transcriptional factor mRNA selected from the group consisting of ZEB1 and BLIMP-1, wherein, when transfected into a cell, said siRNA oligonucleotide is capable of increasing the gene activity of IFN-λ1.

In one aspect, the present invention provides a siRNA molecule having a RNA interfering activity against ZEB1 mRNA, wherein the siRNA molecule comprises a sequence complementary to a ZEB1 mRNA. The nucleotide sequence for ZEB1 mRNA having GenBank Accession Numbers of NM_001128128 or NM_030751.

In one aspect, the present siRNA molecule comprises an anti-sense strand comprising a nucleotide sequence that is complementary to ZEB1 mRNA.

In one aspect, the present invention provides a siRNA oligonucleotide targeted against ZEB1 mRNA, wherein the siRNA oligonucleotide is at least one siRNA oligonucleotide selected from the group consisting of SEQ ID NO: 12, SEQ ID NO: 13, SEQ ID NO: 14, and SEQ ID NO: 15.

In one aspect, the present invention provides a siRNA molecule having a RNA interfering activity against BLIMP-1 RNA, wherein the siRNA molecule comprises a sequence complementary to a BLIMP-1 mRNA. The nucleotide sequence for BLIMP-1 mRNA having GenBank Accession Numbers of NM_001198.3 or NM_182907.

In one aspect, the present siRNA molecule comprises an anti-sense strand comprising a nucleotide sequence that is complementary to BLIMP-1 mRNA.

In one aspect, the present invention provides a siRNA oligonucleotide targeted against BLIMP-1 mRNA, wherein said siRNA oligonucleotide is at least one siRNA oligonucleotide selected from the group consisting of SEQ ID NO: 8, SEQ ID NO: 9, SEQ ID NO: 10, and SEQ ID NO: 11.

In one aspect, the present invention provides a siRNA oligonucleotide that is capable of increasing IFN-λ1 gene activity. An increased IFN-λ1 gene activity may be measured by an increase in IFN-λ1 mRNA or an increase in IFN-λ1 protein. Preferably, the IFN-λ1 mRNA is measured by qPCR. Preferably, the IFN-λ1 protein is measured by an ELISA.

In one aspect, the present invention provides a siRNA oligonucleotide that is capable of decreasing IFN-λ1 gene activity. A decreased IFN-λ1 gene activity may be measured by a decrease in IFN-λ1 mRNA or a decrease in IFN-λ1 protein. Preferably, the IFN-λ1 mRNA is measured by qPCR. Preferably, the IFN-λ1 protein is measured by an ELISA.

In one aspect, the present siRNA oligonucleotide comprises a modified inter-nucleoside linkage. Preferably, the modified inter-nucleoside linkage is a phosphorothioate linkage.

In one aspect, the present siRNA oligonucleotide comprises a modified sugar moiety. Preferably, the modified sugar moiety is a 2'-O-methyl sugar moiety.

In one aspect, the present invention provides a pharmaceutical composition comprising a siRNA and a pharmaceutical acceptable excipient, wherein siRNA oligonucleotide is 15-30 nucleobases in length and is targeted against a transcriptional factor mRNA selected from the group consisting of ZEB1 and BLIMP-1, wherein, when transfected into a cell. The siRNA oligonucleotide is capable of increasing the gene activity of IFN-λ1.

In one aspect, the present invention provides a pharmaceutical composition comprising a siRNA and a pharmaceutical acceptable excipient, wherein the siRNA oligonucleotide is at least one siRNA oligonucleotide selected from the group consisting of SEQ ID NO: 12, SEQ ID NO: 13, SEQ ID NO: 14, and SEQ ID NO: 15.

In one aspect, the present invention provides a pharmaceutical composition comprising a siRNA and a pharmaceutical acceptable excipient, wherein the siRNA oligonucleotide is at least one siRNA oligonucleotide selected from the group consisting of SEQ ID NO: 8, SEQ ID NO: 9, SEQ ID NO: 10, and SEQ ID NO: 11.

In one aspect, the present invention provides a method of increasing expression of IFN-λ1 protein in a mammalian cell, comprising the step of exposing a siRNA oligonucleotide to a mammalian cell, wherein said siRNA oligonucleotide targets against a transcriptional factor mRNA selected from the group consisting of ZEB1 and BLIMP-1, thereby enhancing the production of IFN-λ1 protein. Preferably, the mammalian cell may be airway epithelial cells or colon epithelial cells.

In one aspect, the present invention provides a method of increasing expression of IFN-λ1 protein in a mammalian cell, comprising the step of exposing a siRNA oligonucleotide to a mammalian cell, wherein said siRNA oligonucleotide targeted against ZEB1 mRNA is at least one siRNA oligonucleotide selected from the group consisting of SEQ ID NO: 12, SEQ ID NO: 13, SEQ ID NO: 14, and SEQ ID NO: 15. Preferably, the mammalian cell may be airway epithelial cells or colon epithelial cells.

In yet one aspect, the present invention provides a method of increasing expression of IFN-λ1 protein in a mammalian cell, comprising the step of exposing a siRNA oligonucleotide to a mammalian cell, wherein the siRNA oligonucleotide targeted against EVI1 or CRX mRNA. The siRNA oligonucleotide is at least one siRNA oligonucleotide selected from the group consisting of SEQ ID NOs: 56, 57, 58, 59, 60, 61, 62 and 63.

In one aspect, the present invention provides a method of decreasing expression of IFN-λ1 protein in a mammalian cell, comprising the step of exposing a siRNA oligonucleotide to a mammalian cell, wherein the siRNA oligonucleotide targeted against GATA1 mRNA. The siRNA oligonucleotide is at least one siRNA oligonucleotide selected from the group consisting of SEQ ID NOs: 52, 53, 54 and 55. Preferably, the mammalian cell is airway epithelial cell.

In one aspect, the present invention provides a method of treating a human subject inflicted with an asthmatic disease, comprising the step of administering a therapeutically effective amount of a siRNA oligonucleotide to said human subject, said siRNA oligonucleotide is targeted against ZEB1 mRNA or BLIMP-1 mRNA, and induces the production of an IFN-λ1 protein having an amino acid sequence set forth in NCBI Accession No. NP_742152.

In one aspect, the present invention provides a method of treating a human subject inflicted with an asthmatic disease, comprising the step of administering a therapeutically effective amount of a siRNA to said human subject, said siRNA oligonucleotide is at least one oligonucleotide selected from the group consisting of SEQ ID NO: 12, SEQ ID NO: 13, SEQ ID NO: 14, and SEQ ID NO: 15, and said ZEB1 mRNA has a nucleotide sequence set forth in GenBank Accession No: NM_030751 or Accession No: NM_001128128.

In one aspect, the present invention provides a method of treating a human subject inflicted with an asthmatic disease, comprising the step of administering a therapeutically effective amount of a siRNA to said human subject, said siRNA oligonucleotide is at least one oligonucleotide selected from the group consisting of SEQ ID NO: 8, SEQ ID NO: 9, SEQ ID NO: 10, and SEQ ID NO: 11, and said BLIMP-1 mRNA has a nucleotide sequence set forth in GenBank Accession No: NM_001198 or NM_182907.

In one aspect, the present invention provides a method of treating a human subject inflicted with a colon disease (in needs of upregulation of IFN-λ1 protein), comprising the step of administering a therapeutically effective amount of a siRNA oligonucleotide to said human subject, said siRNA oligonucleotide is targeted against ZEB1 mRNA or BLIMP-1 mRNA, and induces the production of an IFN-λ1 protein having an amino acid sequence set forth in NCBI Accession No. NP_742152.

In one aspect, the present invention provides a method of treating a human subject inflicted with a colon disease (in needs of upregulation of IFN-λ1 protein), comprising the step of administering a therapeutically effective amount of a siRNA to said human subject, said siRNA oligonucleotide is at least one oligonucleotide selected from the group consisting of SEQ ID NO: 12, SEQ ID NO: 13, SEQ ID NO: 14, and SEQ ID NO: 15, and said ZEB1 mRNA has a nucleotide sequence set forth in GenBank Accession No: NM_030751 or Accession No: NM_001128128.

In one aspect, the present invention provides a method for identifying a compound that affects (activates or inhibits) IFN-λ1 promoter activity, comprising the steps of: (a) providing an IFN-λ1 promoter construct that is fused with a reporter gene, wherein said IFN-λ1 promoter construct is at least one promoter construct selected from the group consisting of SEQ ID NO: 1, SEQ ID NO: 2, SEQ ID NO: 3, SEQ ID NO: 4, SEQ ID NO: 5, SEQ ID NO: 6, or SEQ ID NO: 7; (b) transfecting a mammalian cell with said IFN-λ1 promoter construct; (c) screening a compound with said transfected cell by: (a') exposing said compound to said transfected cell; and (b') determining said reporter gene activity of said transfected cell, wherein a change in said reporter gene activity is indicative of an activating or inhibitory activity of said compound towards said IFN-λ1 promoter activity. Preferably, the reporter gene is a luciferase gene. Preferably, the mammalian cell is a human airway epithelial cell.

In one aspect, the screened compounds possess an ability to increase IFN-λ1 promoter activity. The compound may be a siRNA oligonucleotide, and it targets against ZEB1 mRNA or BLIMP-1 mRNA.

In one aspect, step (a) is performed by providing an IFN-λ1 promoter construct comprising SEQ ID NO: 5 and SEQ ID NO: 6.

In one aspect, the present invention provides a pharmaceutical composition containing siRNA against ZEB1 mRNA that can be used to increase the expression of IFN-λ1 gene. The increased IFN-λ1 gene expression enhances the production of IFN-λ1 protein which possesses anti-viral activity to combat viral infection as well as alleviate symptoms associated with a disease condition (e.g., asthma or colon disease). The use of siRNA against ZEB1 to regulate IFN-λ1 gene represents a novel means to modulate the treatment for viral infection and asthma in human.

In one aspect, the present invention provides a pharmaceutical composition containing siRNA against BLIMP-1 mRNA that can be used to increase the expression of IFN-λ1 gene. The increased IFN-λ1 gene expression enhances the production of IFN-λ1 protein which possesses anti-viral activity to combat viral infection as well as alleviate symptoms associated with a disease condition (e.g., asthma). The use of siRNA to against BLIMP-1 regulate IFN-λ1 gene represents a novel means to modulate the treatment for viral infection and asthma in human.

In one aspect, the present invention is directed to a siRNA molecule comprises an anti-sense strand oligonucleotide having about 15 to about 30 nucleotides, wherein the anti-sense strand is complementary to a portion of the ZEB1 or BLIMP-1 mRNA sequences. Preferably, the siRNA is about 15 to about 22 nucleotides.

In one aspect, the present invention provides a method of increasing expression of IFN-λ1 protein in a colon epithelial cell, comprising the steps of: i) providing a colon epithelial cell in needs thereof; and ii) exposing a siRNA oligonucleotide targets against the ZEB1 transcriptional factor mRNA to the colon epithelial cell, thereby increasing the IFN-λ1 protein expression by said colon epithelial cell, wherein the ZEB1 mRNA has a nucleotide sequence set forth in Accession No: NM_030751 or Accession No: NM_001128128. Preferably, the siRNA oligonucleotide targeted against ZEB1 mRNA consists of SEQ ID NO: 12, SEQ ID NO: 13, SEQ ID NO: 14, and SEQ ID NO: 15. The increased IFN-λ1 protein expression can be measured by an increase in IFN-λ1 protein secretion; and the increased IFN-λ1 protein expression can be measured by an ELISA. Preferably, the colon epithelial cell is a human colon epithelial cell.

In another aspect, the present invention provides a method of treating a human subject inflicted with a colon disease, comprising the step of administering a therapeutically effective amount of a siRNA oligonucleotide to the human subject, the siRNA oligonucleotide is targeted against ZEB1 mRNA, and induces the production of an IFN-λ1 protein having an amino acid sequence set forth in GenBank Accession No. NP_742152, and the ZEB1 mRNA has a nucleotide sequence set forth in GenBank Accession No: NM_030751 or GenBank Accession No: NM_001128128. Preferably, the siRNA oligonucleotide is at least one oligonucleotide selected from the group consisting of SEQ ID NO: 12, SEQ ID NO: 13, SEQ ID NO: 14, and SEQ ID NO: 15.

BRIEF DESCRIPTION OF THE DRAWINGS

FIG. 2 depicts the nucleotide sequence of the ~4 kb IFN-λ1 promoter (SEQ ID NO: 1). The 4,068 bp IFN-λ1 promoter fragment was obtained through PCR amplification from a genomic DNA using primers directed to amplify positions 12051212-12055279 on the NT_011109.15|Hs19_11266 Homo sapiens chromosome 19 genomic contig, reference assembly.

FIG. 7A depicts a schematic representation of the putative transcription sites present on the ~0.6 kb IFN-λ1 promoter fragment (SEQ ID NO: 7). FIG. 7B depicts a lack of change in luciferase activity in BEAS-2B cells that were transfected with the ~0.6 kb IFN-λ1 reporter construct and stimulated with poly I:C. A SV40 promoter reporter construct was used to indicate success in transfection. Negative control included vector only. Data from three (3) replicate experiments were averaged and means (+/−SEM) are shown.

FIG. 11A depicts the time course of IFN-λ1 mRNA expression in naïve BEAS-2B cells following poly I:C challenge. BEAS-2B cells were treated with poly I:C for the indicated lengths of time. The IFN-λ1 mRNA expression peaked at 180 minutes and returned to nearly baseline level at 360 minutes. FIG. 11B depicts a schematic representation of the forward primer (SEQ ID NO: 28) and the reverse primer (SEQ ID NO: 29) positions to detect ZEB1 binding by ChIP assay. FIG. 11C depicts the immunoprecipitation of ZEB1 binding to the IFN-λ1 promoter in a ChIP assay. BEAS-2B cells were challenged with poly I:C for various times (0-270 minutes) and nuclear extracts of these cells were prepared. The DNA-protein complex (i.e., ZEB1 bound to IFN-λ1 promoter) in the nuclear extracts was obtained by immunoprecipation (using an antibody against ZEB1). qPCR of the immunoprecipitates (containing ZEB1 bound to IFN-λ1 promoter) was performed using the F1 and R1 site-specific primers. The data are represented as average IP fold-enrichment (calculated as $2^{[(Ct(ZEB1)-Ct(input))-(Ct(IgG)-Ct\ (input))]}$) (see Materials and Methods).

FIG. 16A depicts the mRNA expression of Mx1 (an anti-viral response gene) using qPCR. QPCR was performed on BEAS-2B cells transfected with siRNA against ZEB1 or BLIMP-1. Non-targeting siRNA (NT siRNA) served as a negative control. Transfectants were challenged with poly I:C. siRNA against ZEB1 and BLMP1 increased the mRNA expression of the anti-viral Mx1 gene (e.g., 24 hours). FIG. 16B depicts the mRNA expression of OAS1 (another anti-viral gene) using qPCR. siRNA against ZEB1 and BLIMP-1 increased the mRNA expression of the anti-viral OAS1 gene. Altogether, siRNA against ZEB1 and BLIMP-1 increases the expression of anti-viral genes, probably via upregulation of IFN-λ1 gene expression.

7082) was added in the culture. Note that the NF-κB inhibitor completely abrogated the virally induced IFN-λ1 reporter gene activation.

Figure 22A:
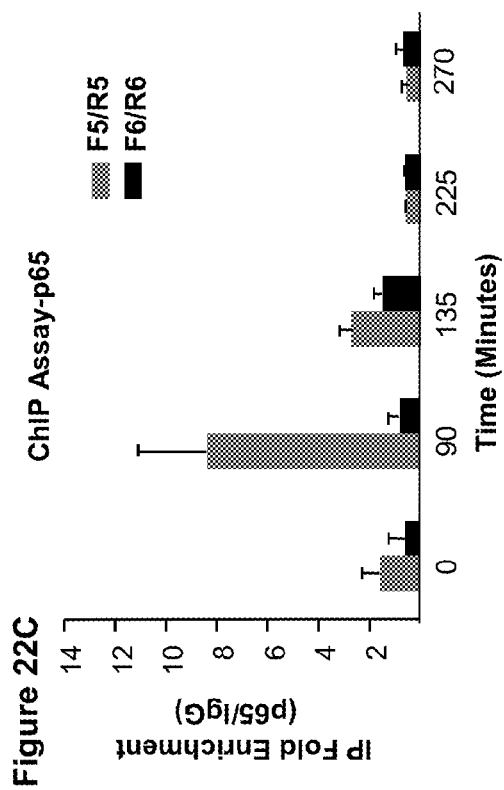
Figure 22C:
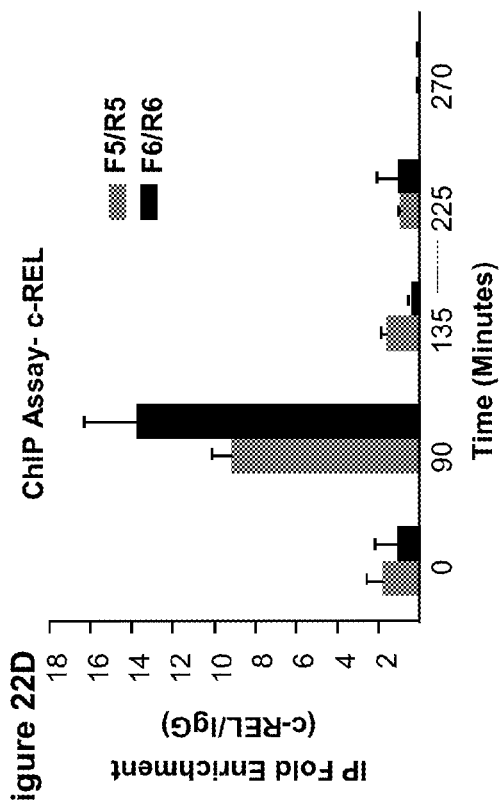
Figure 22B:
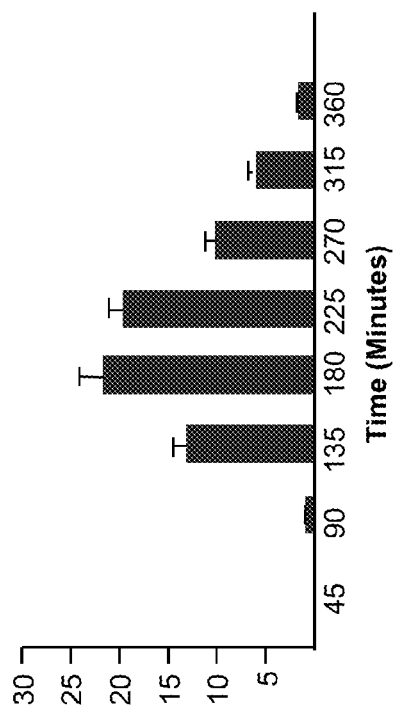
Figure 22D:
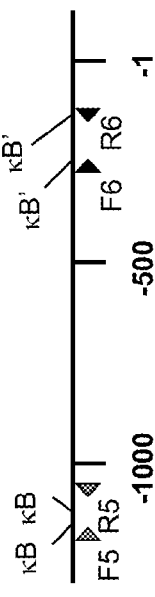

FIG. 22A depicts the time course of IFN-λ1 mRNA expression in naïve BEAS-2B cells following poly I:C challenge. FIG. 22B depicts a schematic representation of two (2) primer sets (F5-R5 and F6-R6) (i) Forward 5 (F5) and Reverse 5 (R5) (SEQ ID NOs: 36 and 37) to amplify the κB region of the IFN-λ1 promoter (near the −1,000 bp); and (ii) Forward 6 (F6) and Reverse 6 (R6) (SEQ ID NOs: 38 and 39) to amplify the κB' (additional κB sites) region of the IFN-λ1 promoter (between the −100 and −500 bp region). FIG. 22C depicts a ChIP assay for p65 (a NF-κB subunit). In this assay, p65 was immunoprecipitated using a specific anti-p65 antibody, followed by qPCR using the F5-R5 and F6-R6 primer pairs directed against the two NF-κB regions (described in FIG. 22B) in the IFN-λ1 promoter. Note that the κB site (near the −1,000 bp) is essential, but the κB' site plays no significant role in mediating the NF-κB binding with the IFN-λ1 promoter. FIG. 22D depicts a ChIP assay for c-REL (another NF-κB subunit). In this assay, c-REL was immunoprecipitated using a specific anti-c-REL antibody, followed by qPCR using the same F5-R5 and F6-R6 primer pairs. Note that the both κB site (near the −1,000 bp) and κB' site mediate the c-REL binding to the IFN-λ1 promoter.

Figures 23A, 23B:
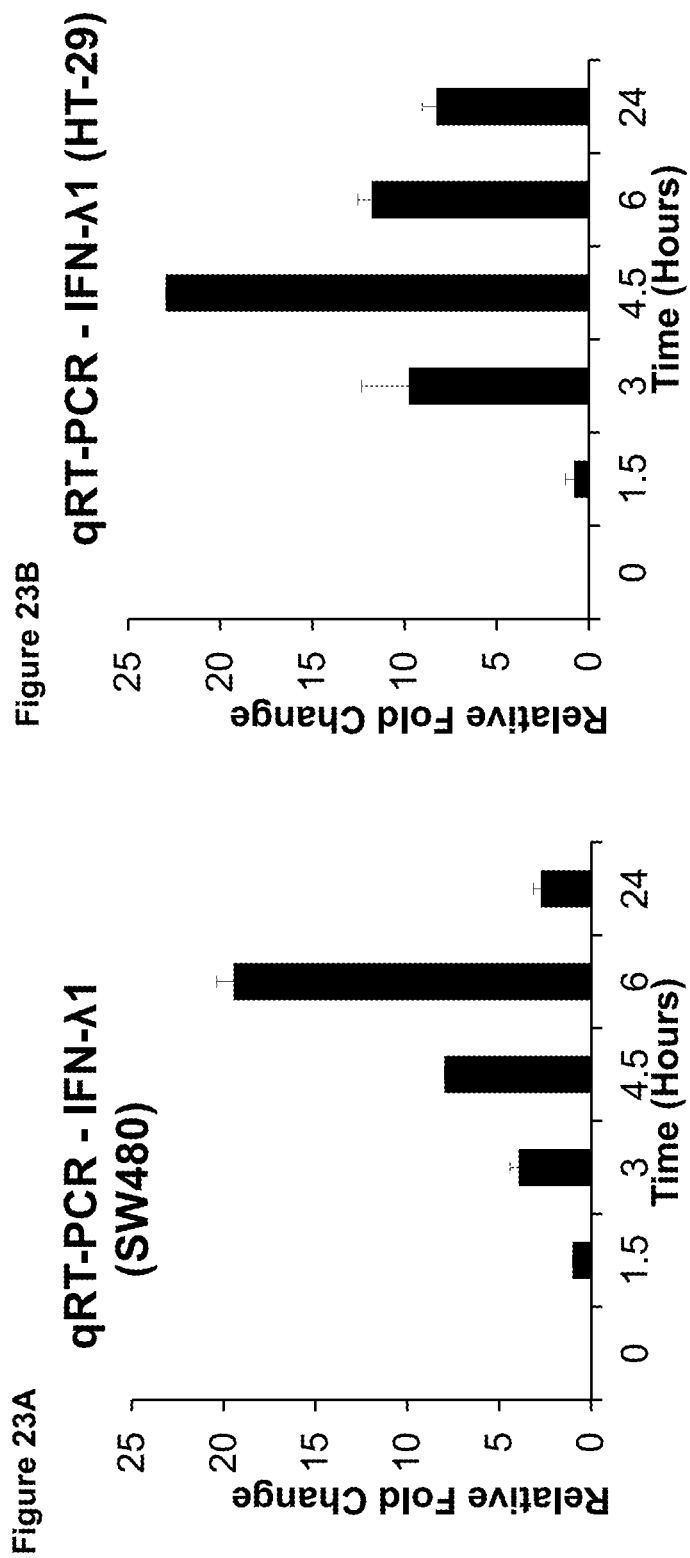

FIG. 23A depicts the time course of IFN-λ1 mRNA expression in SW480 colon epithelial cells following poly I:C challenge (i.e., to mimic viral infection). SW480 cells were treated with poly I:C for 1.5, 3, 4.5, 6 or 24 hours. Total cellular RNA was isolated from SW480 cells. qRT-PCR was performed to quantify mRNA expression of IFN-λ1. Note that IFN-λ1 mRNA expression peaked at 6 hours post-poly I:C challenge. FIG. 23B depicts the time course of IFN-λ1 mRNA expression in HT-29 colon epithelial cells following poly I:C challenge. HT-29 cells were treated with poly I:C for 1.5, 3, 4.5, 6 or 24 hours. Total cellular RNA was isolated from HT-29 cells. qRT-PCR was similarly performed to quantify mRNA expression of IFN-λ1. Note that IFN-λ1 mRNA expression peaked at 4.5 hours post-poly I:C challenge.

Figure 24:
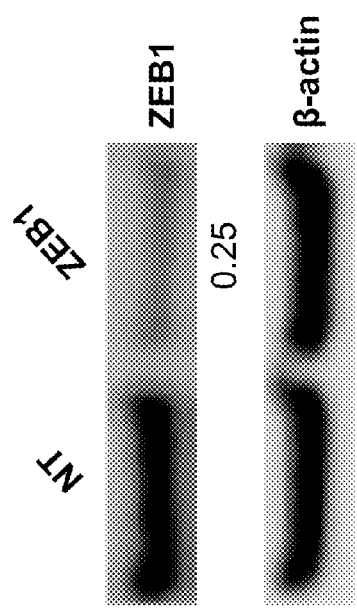

FIG. 24 depicts the Western blot analysis of the SW480 cells transfected with siRNA (a pool of four siRNA oligonucleotides consisting of SEQ ID NOs: 12, 13, 14, and 15) against ZEB1 mRNA. Note that siRNA treatment reduced the targeted ZEB1 protein, without altering the β-actin level, indicating specificity.

Figure 25:
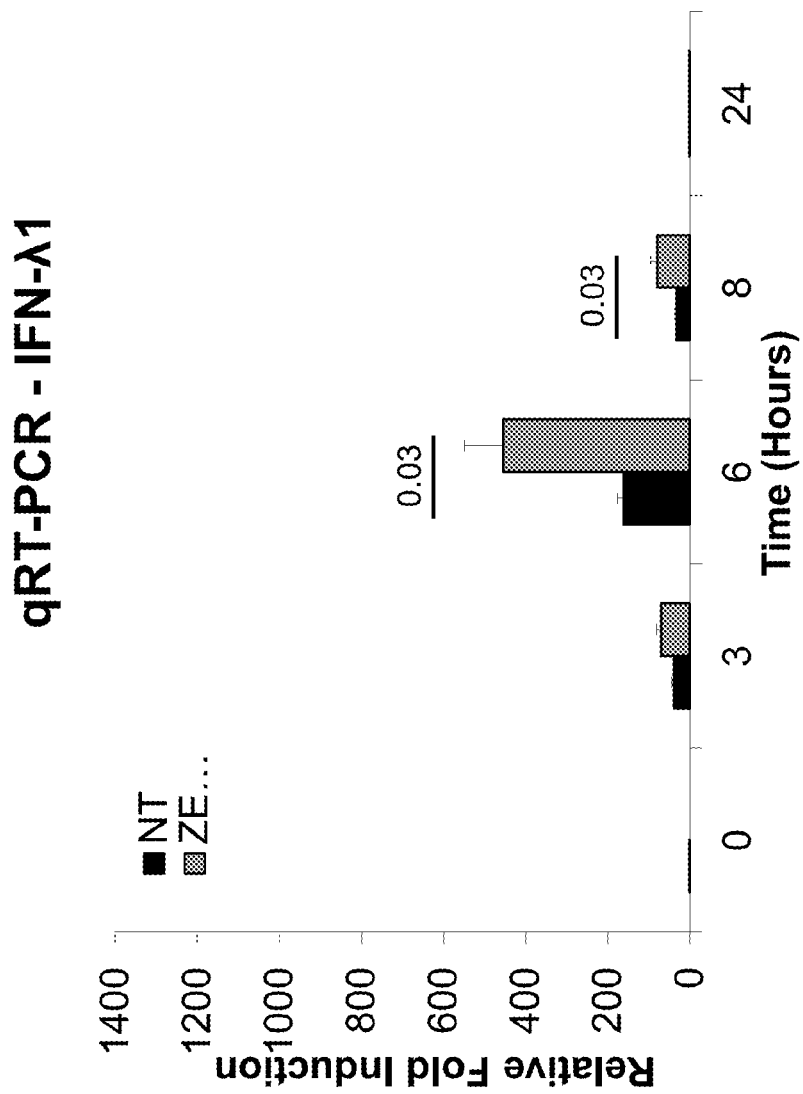

FIG. 25 depicts the effects of ZEB1 siRNA (a pool of four siRNA oligonucleotides consisting of SEQ ID NOs: 12, 13, 14, and 15) on IFN-λ1 mRNA expression. SW480 cells were first transfected with ZEB1 siRNA (a pool of four siRNA oligonucleotides consisting of SEQ ID NOs: 12, 13, 14, and 15). Transfected cells were challenged with poly I:C for 24 hours. qRT-PCR was then performed to monitor the mRNA expression of the IFN-λ1 gene. Note that at 6 and 8 hours, ZEB1 siRNA treatment increased IFN-λ1 mRNA expression. Statistical analysis was performed using a Student's t-test; the p-values are indicated.

Figure 26:
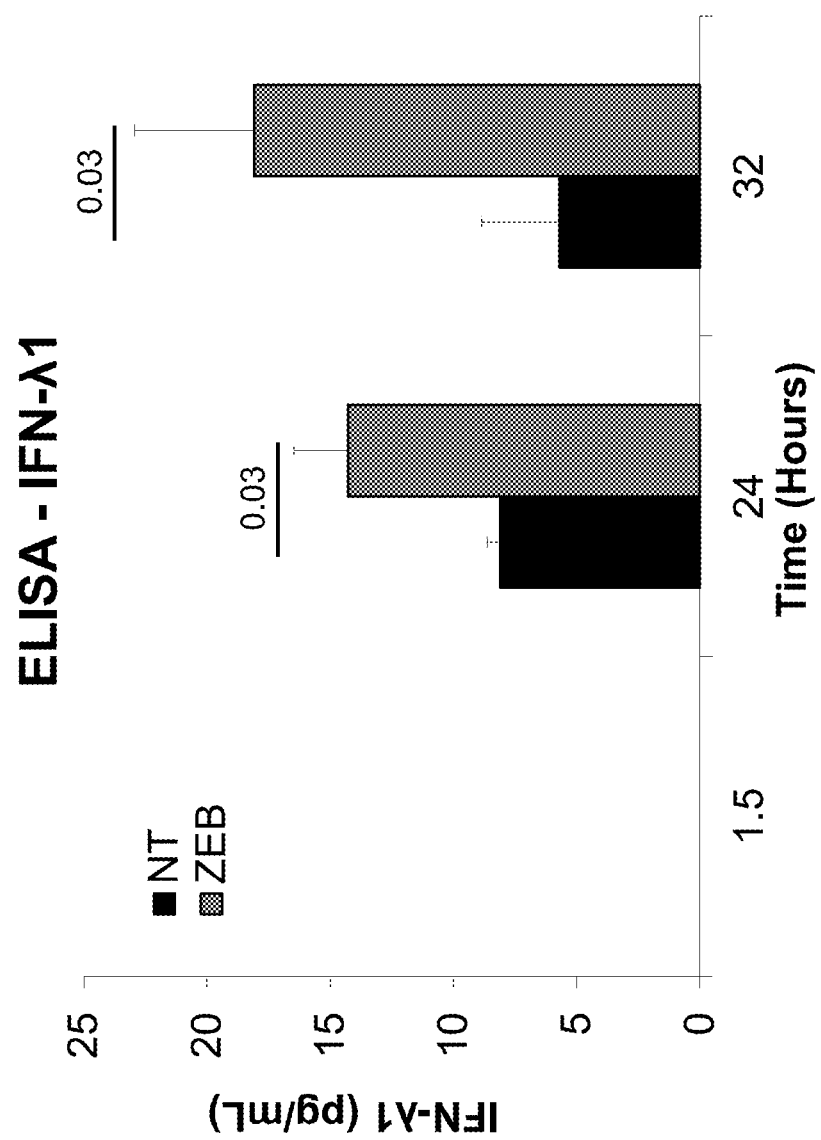

FIG. 26 depicts an ELISA experiment showing the IFN-λ1 concentration from ZEB1 siRNA-transfected SW480 cells. SW480 cell supernatants were obtained from the ZEB1 siRNA-transfected cells that were challenged with poly I:C for varying time periods. Note that the IFN-λ1 concentration increased in the ZEB1 siRNA group as compared to that of control, non-targeting (NT) siRNA-transfected groups from 24 hours to 32 hours. Non-targeting siRNA is a control siRNA pool of four oligonucleotides having sequences designed to not target any known mammalian mRNA sequences and confirmed by genome-wide microarray analysis to have minimal effects within the cell (obtained from Thermo Scientific, Catalogue #D-001810-10-05). Statistical analysis was performed using a Student's t-test; the p-values are indicated.

Figure 27:
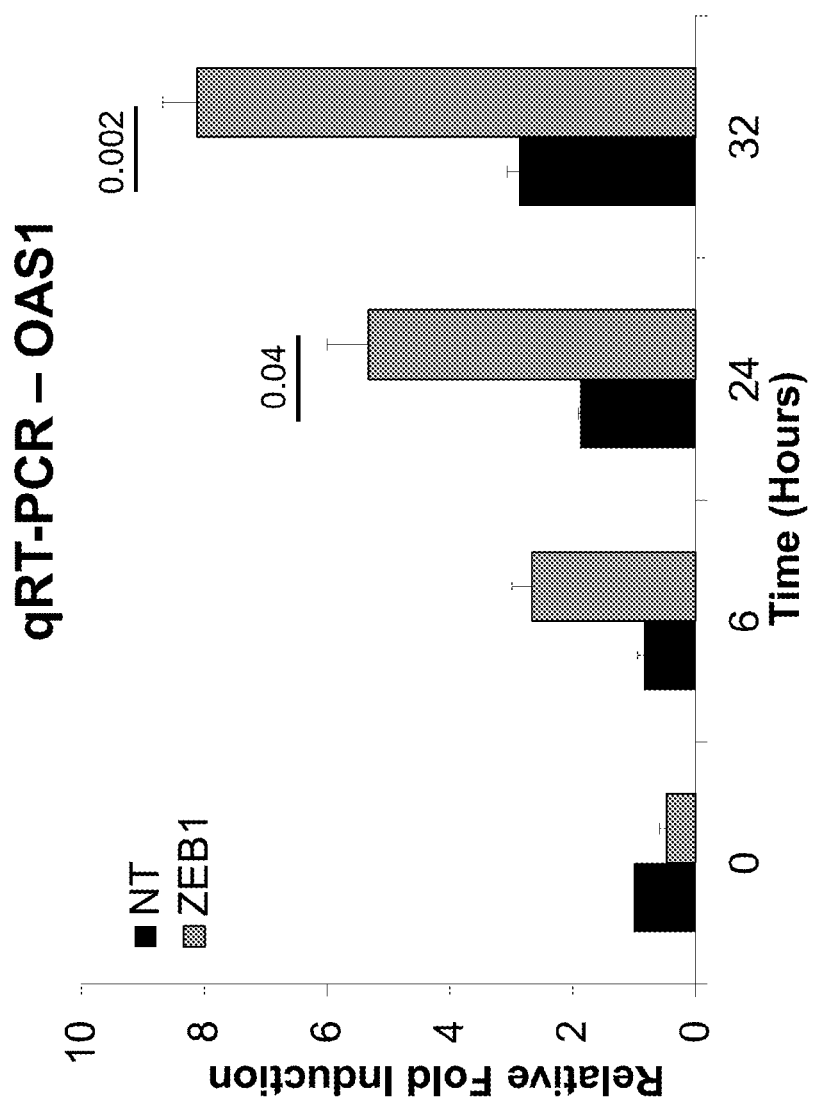

FIG. 27 depicts the mRNA expression of OAS1 (an anti-viral response gene) using qRT-PCR. qRT-PCR was performed on SW480 cells transfected with siRNA against ZEB1 (a pool of four siRNA oligonucleotides consisting of SEQ ID NOs: 12, 13, 14, and 15). Non-targeting (NT) siRNA served as a negative control. Transfectants were challenged with poly I:C. Note that siRNA against ZEB1 increased the mRNA expression of the anti-viral OAS1 gene at 24 and 32 hours. Together, siRNA against ZEB1 is shown to increase the expression of anti-viral genes, probably via the upregulation of IFN-λ1 gene expression. Statistical analysis was performed using a Student's t-test; the p-values are indicated.

Figure 28:
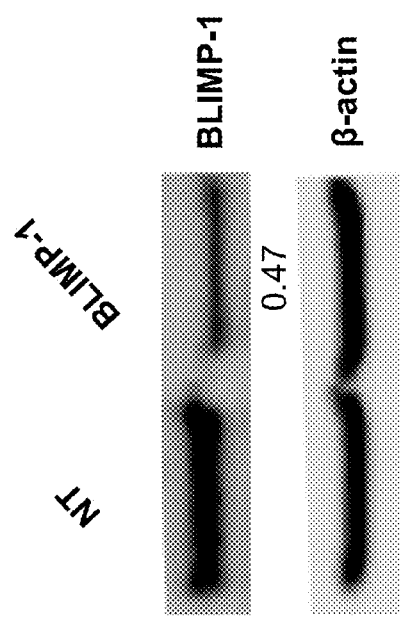

FIG. 28 depicts the Western blot analysis of the SW480 cells transfected with siRNA against BLIMP-1 mRNA (a pool of four siRNA oligonucleotides consisting of SEQ ID NOs: 8, 9, 10, and 11). Note that siRNA treatment reduced the targeted BLIMP-1 protein, without altering the β-actin level, indicating specificity.

Figure 29:
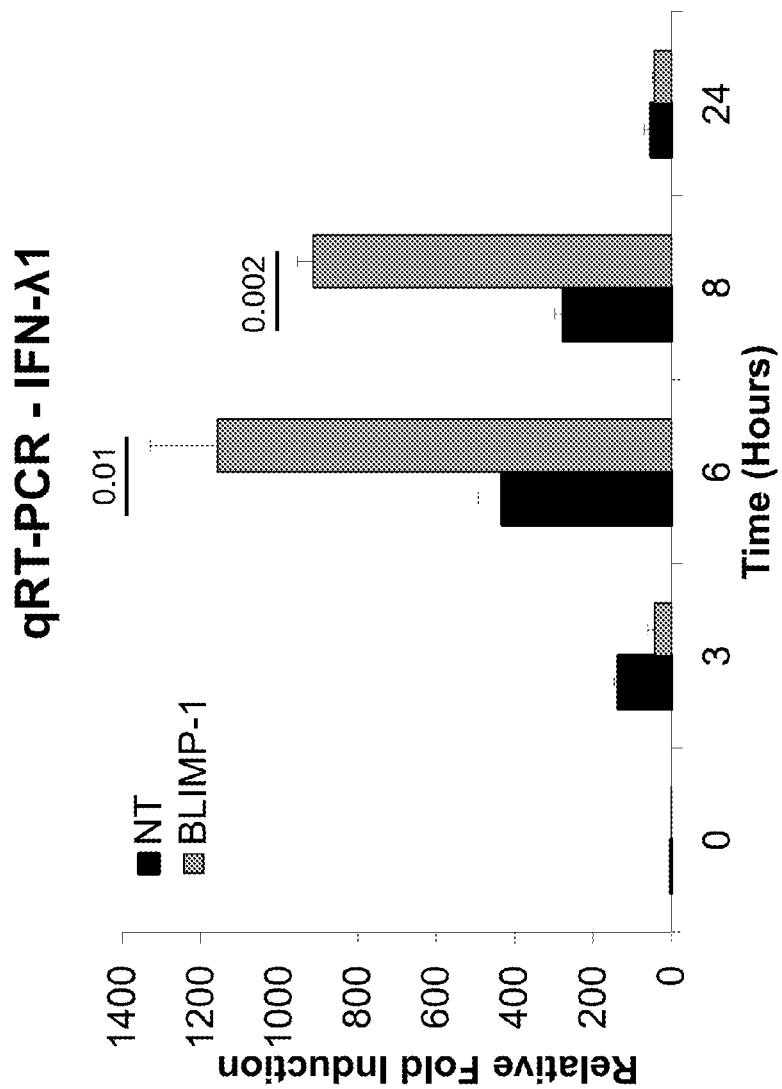

FIG. 29 depicts the effects of BLIMP-1 siRNA on IFN-λ1 mRNA expression. SW480 cells were first transfected with BLIMP-1 siRNA (a pool of four siRNA oligonucleotides consisting of SEQ ID NOs: 8, 9, 10, and 11). Transfected cells were challenged with poly I:C for 24 hours. qRT-PCR was then performed to monitor the mRNA expression of the IFN-λ1 gene. Note that at 6 and 8 hours, BLIMP-1 siRNA treatment increased IFN-λ1 mRNA expression. Statistical analysis was performed using a Student's t-test; the p-values are indicated.

Figure 30:
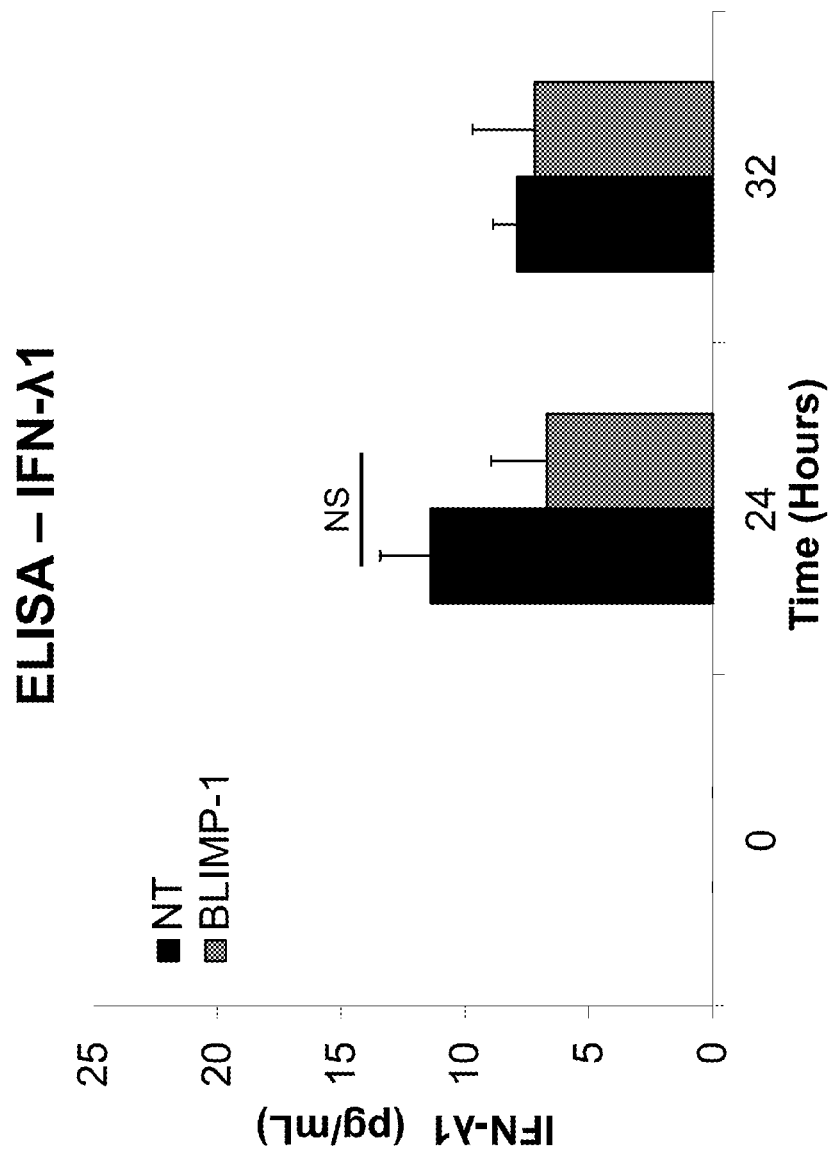

FIG. 30 depicts an ELISA experiment showing the IFN-λ1 concentration from BLIMP-1 siRNA-transfected SW480 cells. SW480 cell supernatants were obtained from the BLIMP-1 siRNA-transfected cells that were challenged with poly I:C for varying time periods. Note that the IFN-λ1 concentration was not altered in the BLIMP-1 siRNA group as compared to that of control (NT) groups.

Figure 31:
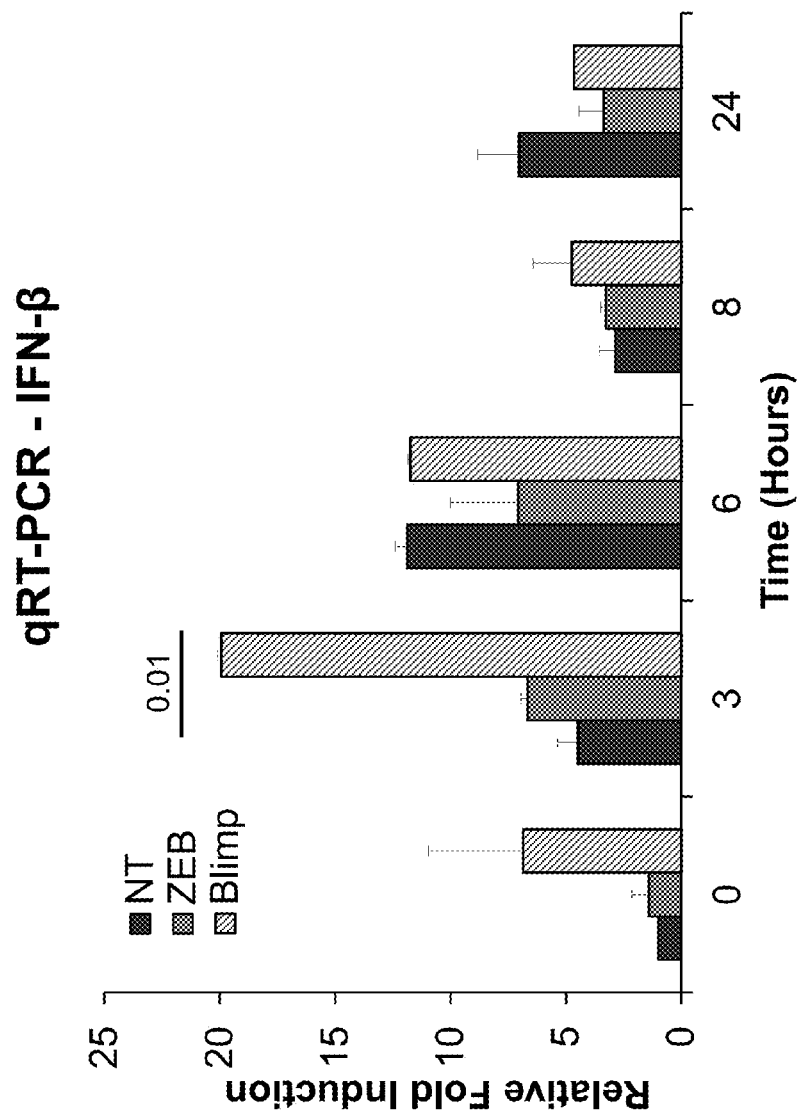

FIG. 31 depicts the specificity of BLIMP-1 siRNA on IFN-β1. siRNA against BLIMP-1 (a pool of four siRNA oligonucleotides consisting of SEQ ID NOs: 8, 9 10, and 11) increased the IFN-β1 mRNA expression (3 hours) while siRNA against ZEB1 (a pool of four siRNA oligonucleotides consisting of SEQ ID NOs: 12, 13, 14, and 15) did not effect the IFN-β1 mRNA expression. Statistical analysis was performed using a Student's t-test; the p-values are indicated.

Figure 32B:
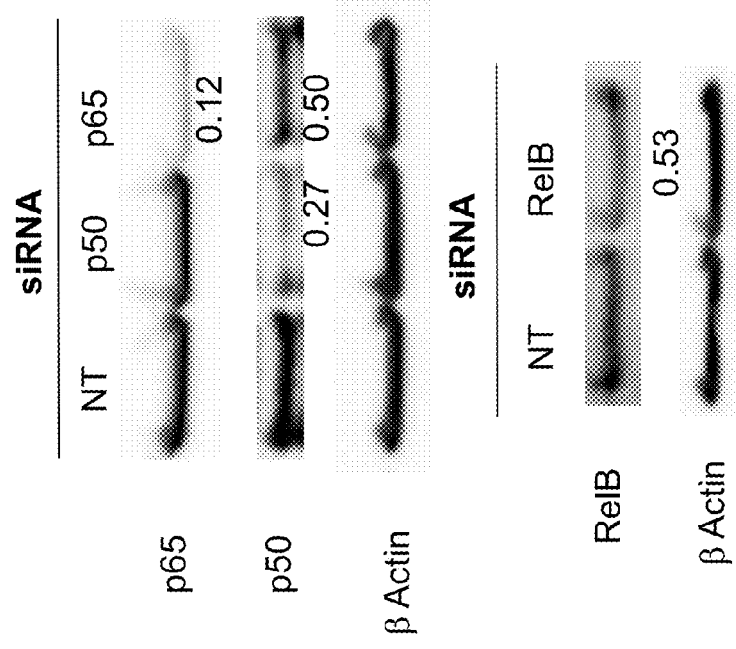
Figure 32A:
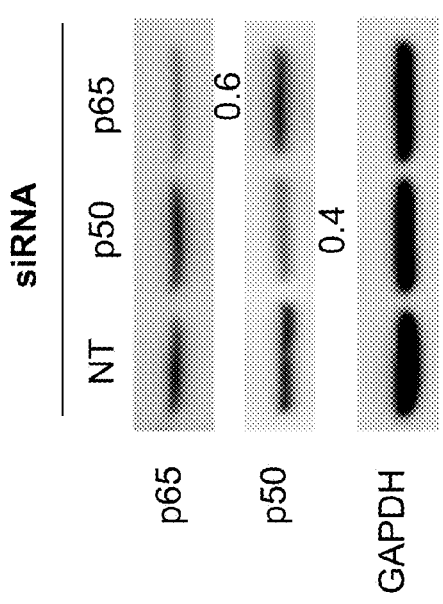

FIG. 32A depicts the Western blot analysis of the BEAS-2B cells transfected with siRNA against the NF-κB p50 (a pool of four siRNA oligonucleotides consisting of SEQ ID NOs: 40, 41, 42, and 43) or NF-κB p65 mRNA (a pool of four siRNA oligonucleotides consisting of SEQ ID NOs: 44, 45, 46, and 47). siRNA treatment reduced the targeted proteins, without altering the GAPDH level, indicating specificity. FIG. 32B depicts the Western blot analysis of the SW480 cells transfected with siRNA against the NF-κB p50 (a pool of four siRNA oligonucleotides consisting of SEQ ID NOs: 40, 41, 42, and 43), NF-κB p65 (a pool of four siRNA oligonucleotides consisting of SEQ ID NOs: 44, 45, 46, and 47), or RelB (a pool of four siRNA oligonucleotides consisting of SEQ ID NOs: 48, 49, 50, and 51). siRNA treatment reduces the targeted proteins, without altering the β-actin level, indicating specificity.

Figure 33B:
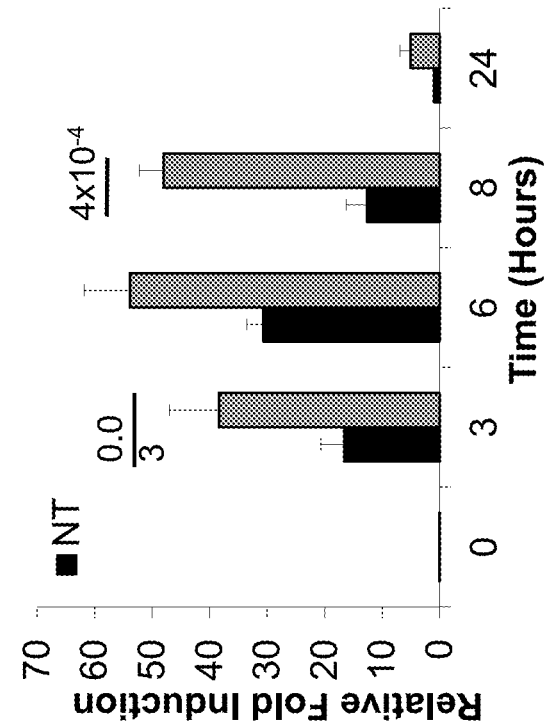
Figure 33A:
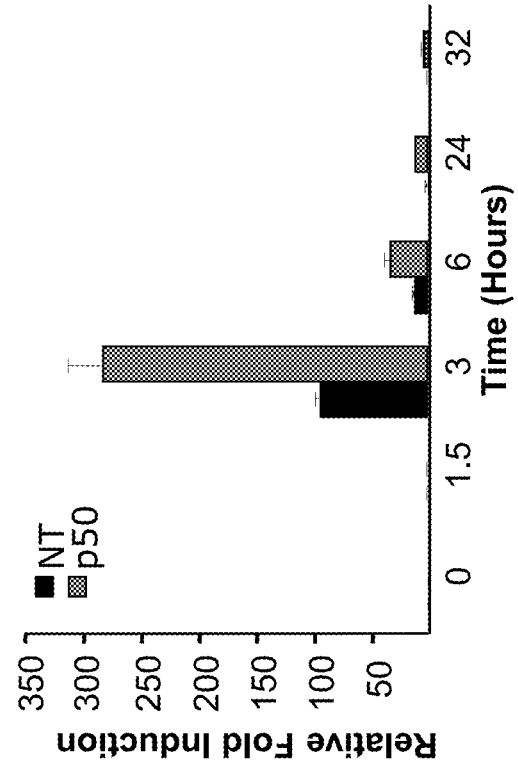

FIG. 33A depicts the effects of NF-κB p50 siRNA on IFN-λ1 mRNA expression in BEAS-2B cells. BEAS-2B cells were first transfected with NF-κB p50 siRNA (a pool of four siRNA oligonucleotides consisting of SEQ ID NOs: 40, 41, 42, and 43). The transfected cells were challenged with poly I:C for 32 hours. qRT-PCR was then performed to monitor the mRNA expression of the IFN-λ1 gene. Note that at 3, 6, 24, and 32 hours, NF-κB p50 siRNA treatment increased IFN-λ1 mRNA expression. FIG. 33B depicts the effects of NF-κB p50 siRNA on IFN-λ1 mRNA expression in SW480 cells. SW480 cells were first transfected with NF-κB p50 siRNA (a pool of four siRNA oligonucleotides consisting of SEQ ID NOs: 40, 41, 42, and 43). The transfected cells were challenged with poly I:C for 24 hours. qRT-PCR was then performed to monitor the mRNA expression of the IFN-λ1 gene. Note that at 3 and 8 hours, NF-κB p50 siRNA treatment increased IFN-λ1 mRNA expression. Statistical analysis was performed using a Student's t-test; the p-values are indicated.

Figure 34A:
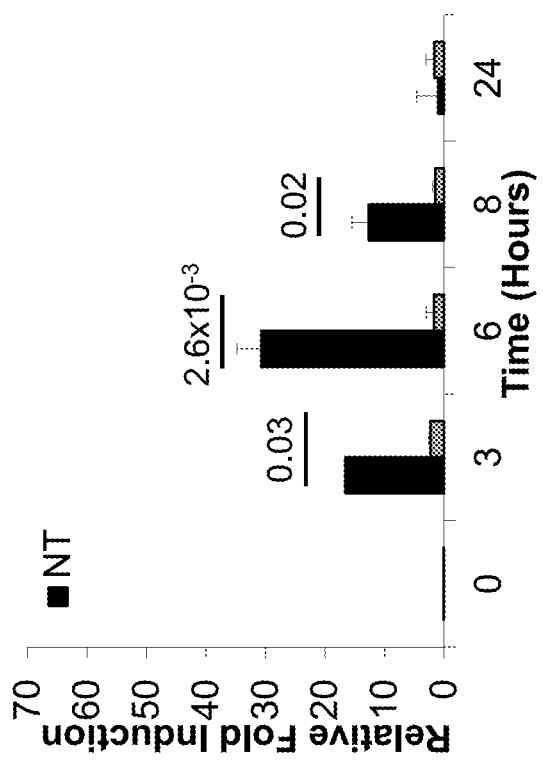
Figure 34B:
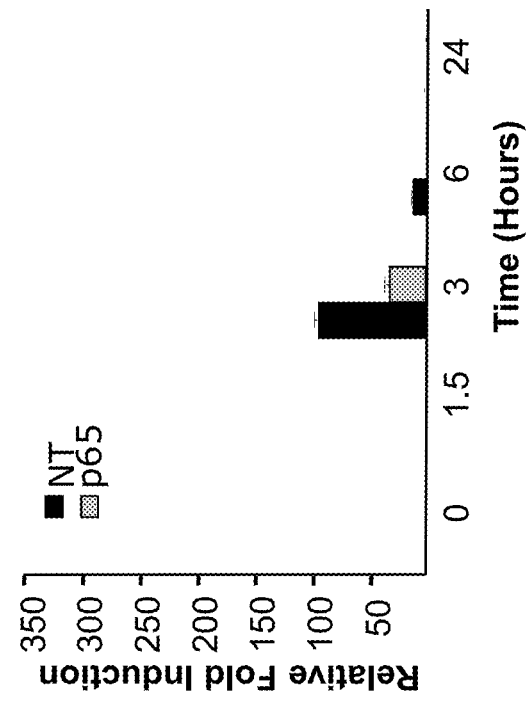

FIG. 34A depicts the effects of NF-κB p65 siRNA (a pool of four siRNA oligonucleotides consisting of SEQ ID NOs: 44, 45, 46, and 47) on IFN-λ1 mRNA expression in BEAS-2B cells. The transfected cells were challenged with poly I:C for 24 hours. qRT-PCR was then performed to monitor the mRNA expression of the IFN-λ1 gene. Note that at 3 and 6 hours, NF-κB p65 siRNA treatment decreased IFN-λ1 mRNA expression. FIG. 34B depicts the effects of NF-κB p65 siRNA (a pool of four siRNA oligonucleotides consisting of SEQ ID NOs: 44, 45, 46, and 47) on IFN-λ1 mRNA expression in SW480 cells. The transfected cells were challenged with poly I:C for 24 hours. qRT-PCR was then performed to monitor the mRNA expression of the IFN-λ1 gene. Note that at 3, 6, and 8 hours, NF-κB p65 siRNA treatment decreased IFN-λ1 mRNA expression. Statistical analysis was performed using a Student's t-test; the p-values are indicated.

Figure 35:
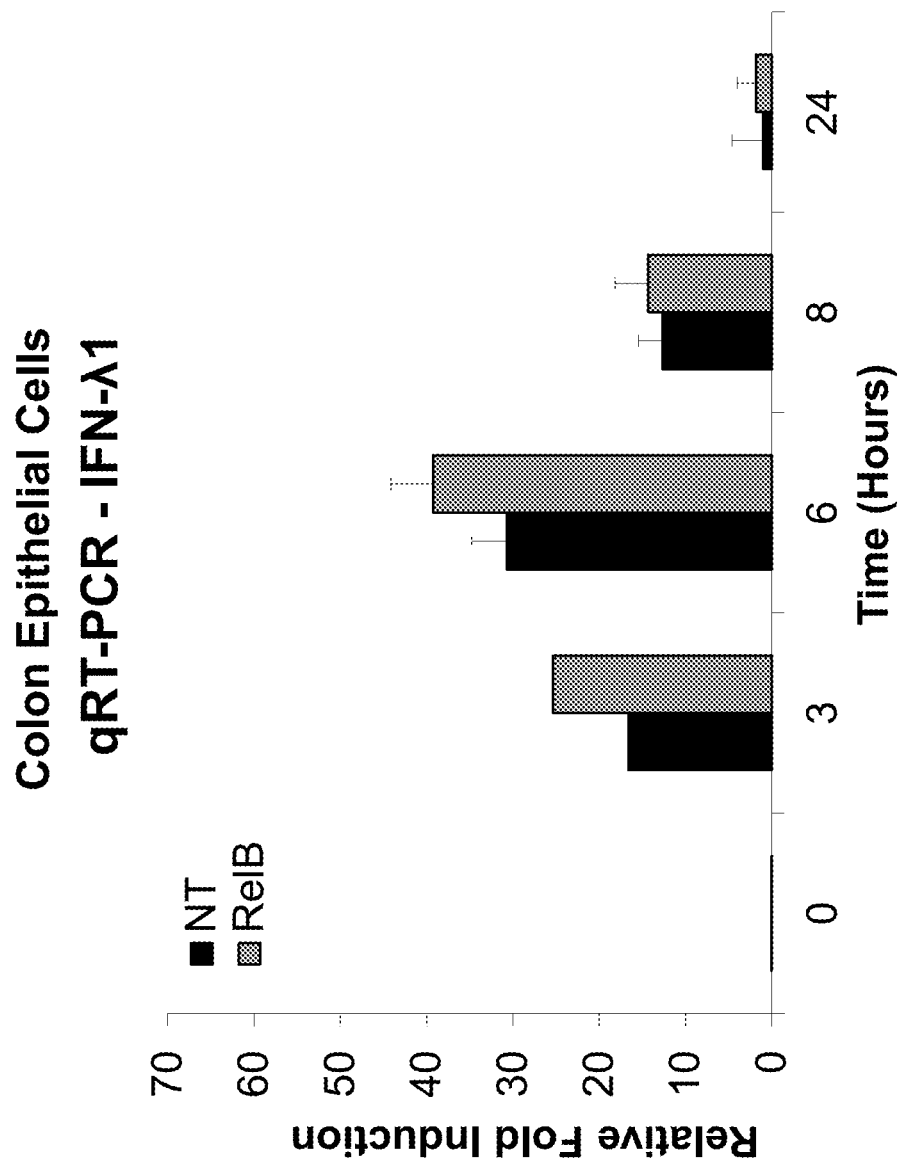

FIG. 35 depicts the effects of RelB siRNA (a pool of four siRNA oligonucleotides consisting of SEQ ID NOs: 48, 49, 50, and 51) on IFN-λ1 mRNA expression in SW480 cells. The transfected cells were challenged with poly I:C for 24 hours. qRT-PCR was then performed to monitor the mRNA expression of the IFN-λ1 gene. Note that RelB siRNA treatment did not alter IFN-λ1 mRNA expression.

Figure 36A:
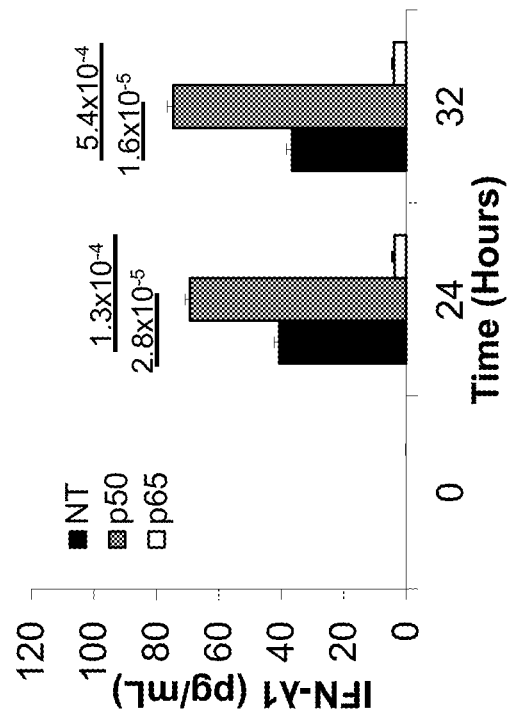
Figure 36B:
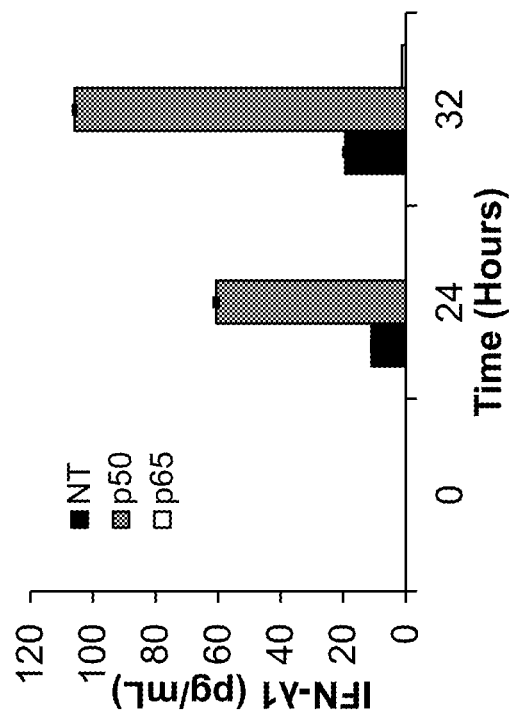

FIG. 36A depicts an ELISA experiment showing the IFN-λ1 concentration from siRNA-transfected BEAS-2B cells. BEAS-2B cell supernatants were obtained from the siRNA-transfected cells that were challenged with poly I:C for varying time periods. Note that the IFN-λ1 concentration increased in the NF-κB p50 siRNA group and decreased in the NF-κB p65 siRNA group as compared to that of control (NT) groups from 24 hours to 32 hours. FIG. 36B depicts an ELISA experiment showing the IFN-λ1 concentration from siRNA-transfected SW480 cells. SW480 cell supernatants were obtained from the siRNA-transfected cells that were challenged with poly I:C for varying time periods. Note that the IFN-λ1 concentration increased in the NF-κB p50 siRNA group and decreased in the NF-κB p65 siRNA group as compared to that of control (NT) groups from 24 hours to 32 hours. Statistical analysis was performed using a Student's t-test; the p-values are indicated.

Figure 37:
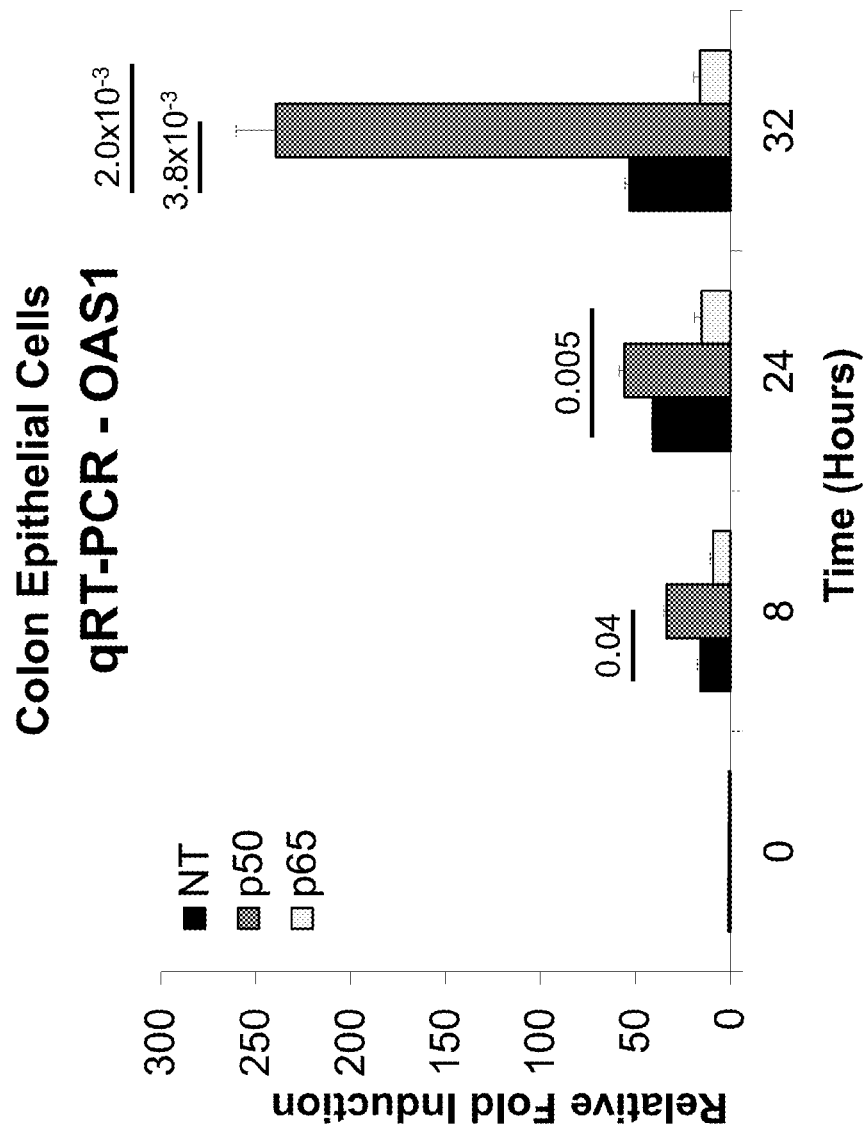

FIG. 37 depicts the mRNA expression of OAS1 (an anti-viral response gene) using qRT-PCR. qRT-PCR was performed on SW480 cells transfected with siRNA against NF-κB p50 or NF-κB p65. Control, non-targeting siRNA (NT) served as a negative control. Transfectants were challenged with poly I:C. siRNA against NF-κB p50 (a pool of four siRNA oligonucleotides consisting of SEQ ID NOs: 40, 41, 42, and 43) increased the mRNA expression of the anti-viral OAS1 gene at 8 and 32 hours. Conversely, siRNA against NF-κB p65 (a pool of four siRNA oligonucleotides consisting of SEQ ID NOs: 44, 45, 46, and 47) decreased the mRNA expression of the anti-viral OAS1 gene at 24 and 32 hours. Altogether, siRNA against NF-κB p50 increases and siRNA against NF-κB p65 decreases the expression of anti-viral genes, probably via the upregulation of IFN-λ1 gene expression. Statistical analysis was performed using a Student's t-test; the p-values are indicated.

Figure 38:
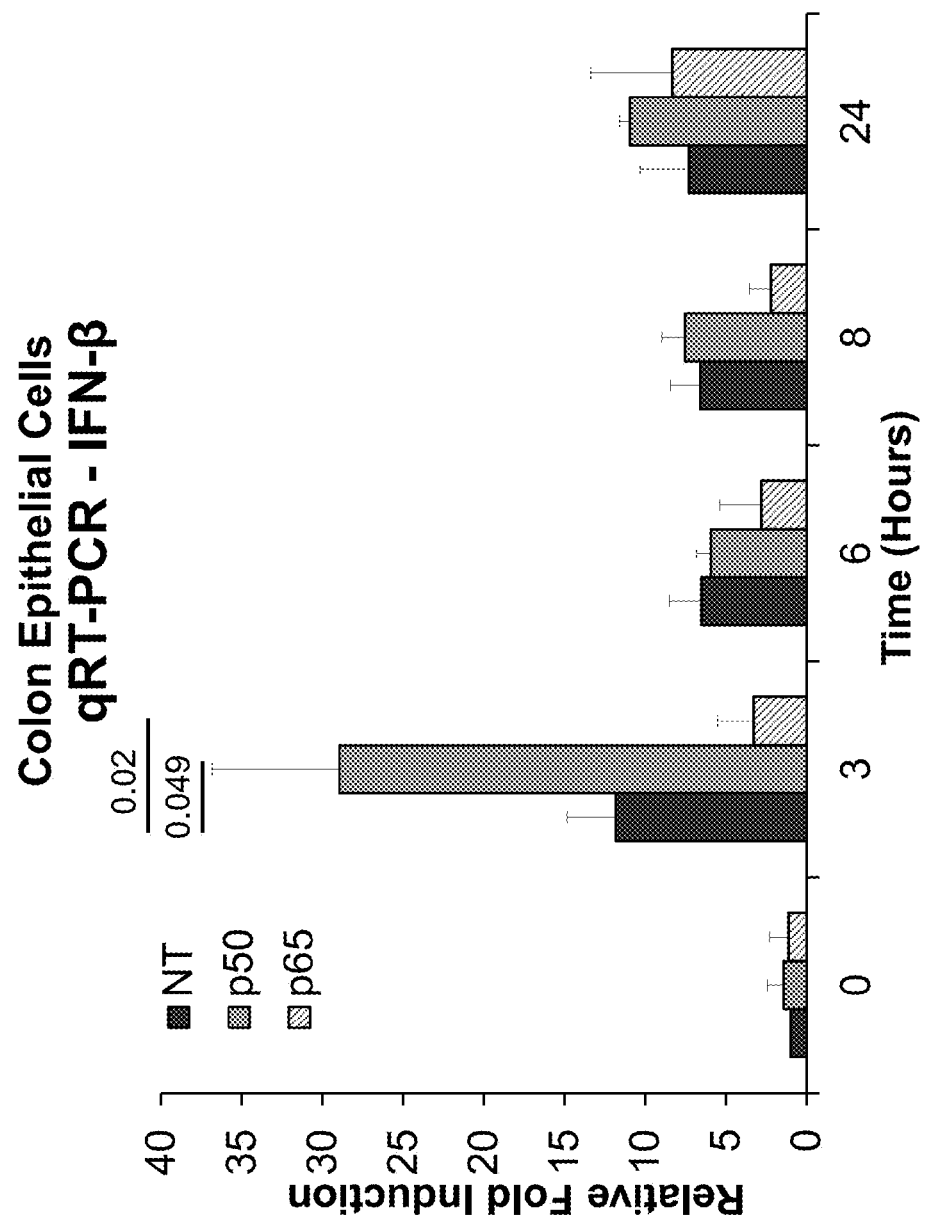

FIG. 38 depicts the specificity of NF-κB p50 and NF-κB p65 siRNA on IFN-β1. siRNA against NF-κB p50 (a pool of four siRNA oligonucleotides consisting of SEQ ID NOs: 40, 41, 42, and 43) increased the IFN-β1 mRNA expression while siRNA against NF-κB p65 (a pool of four siRNA oligonucleotides consisting of SEQ ID NOs: 44, 45, 46, and 47) decreased the IFN-β1 mRNA (3 hours). Statistical analysis was performed using a Student's t-test; the p-values are indicated.

DETAILED DESCRIPTION OF THE INVENTION

Definitions

The following definitions are used for this application:

The term "ChIP Assay" refers to chromatin immunoprecipitation (ChIP) and is an assay used to determine the location of DNA binding sites on the genome for a particular protein of interest. The assay provides information of protein-DNA interactions that occur inside the nucleus of a living cell or tissue.

The term "Luciferase" refers to a class of oxidative enzymes used in bioluminescence and is distinct from a photoprotein. Luciferase is an enzyme purified from the firefly Photinus pyralis.

The term "Luciferase Assay" refers to the use of luciferase is used as a reporter to assess the transcriptional activity in a cell that is transfected with a genetic construct containing the luciferase gene under the control of a promoter of interest.

The term "Promoter" refers to a region of DNA that facilitates the transcription of a particular gene.

The term "qPCR" refers to a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

The term "siRNA" refers to a small interfering RNA (aka short interfering RNA or silencing RNA). RNA interference refers to the process of sequence-specific post-transcriptional gene silencing in animals mediated by short interfering RNA. siRNA is a class of double-stranded RNA molecules, 20-25 nucleotides that are involved in the RNA interference (RNAi) pathway, where it interferes with the expression of a specific gene. siRNA oligonucleotides target the BLIMP-1 or ZEB1 mRNA for degradation via sequence-specific complementary base pairing such that the target mRNA is recognized by the siRNA that has been incorporated into an RNA-induced silencing complex (RISC). Once recognized by the RISC complex, the targeted mRNA is then degraded by RNase-mediated cleavage in P-body cytoplasmic compartment (reviewed in Wu and Belasco 2008).

The term "interferon" refers to a group of glycoproteins that are produced by different cell types in response to various stimuli, such as exposure to a virus, bacterium, parasite, or other antigen, and that prevents viral replication in newly infected cells and, in some cases, modulates specific cellular functions.

The term "IFN-λ1" refers a protein of the helical cytokine family and is a type III interferon. It is also known as Interleukin-29 (IL-29). IFN-λ1 plays an important role in host defenses against microbes and its gene is highly up-regulated in cells infected with viruses. The IFN-λ1 gene is found on chromosome 19 in humans.

The term "IFN-λ2" refers to a protein the helical cytokine family and is a type III interferon. It is also known as Interleukin-28a (IL-28a). The IFN-λ2 gene is located near IL-29 on chromosome 19 in humans.

The term "IFN-λ3" refers to a protein the helical cytokine family and is a type III interferon. It is also known as Interleukin-28b (IL-28b). The IFN-λ3 gene is located near IL-29 on chromosome 19 in humans.

The term "mRNA" refers to the template for protein synthesis; the form of RNA that carries the information from DNA in the nucleus to the ribosome for protein synthesis in the cell.

The term "transcription" refers to RNA synthesis, a process of creating an equivalent RNA copy of a sequence of DNA. A DNA sequence is read by RNA polymerase, which produces a complementary, anti-parallel RNA strand. Transcription is the first step leading to gene expression. If the gene transcribed encodes for a protein, the result of transcription is messenger RNA (mRNA), which will then be used to create that protein via the process of translation.

The term "transfection" refers to a process by which agents (such as IFN-λ1 reporter constructs or siRNAs) are introduced into a cell (such as a mammalian cell). The transfection methods include, but not limited to, calcium phosphate-based transfection, DEAE-dextran-based transfection, lipid-based transfection, molecular conjugate-based transfection (e.g. polylysine-DNA conjugates), electroporation, microinjection and the like.

The term "expression" refers to the process by which information from a gene is used in the synthesis of a functional gene product. This term is used to refer to mRNA or protein levels in the cell.

The term "transcriptional site" refers to a binding site in a region of the DNA to which a transcription factor binds.

The term "transcription factor" refers to a protein that binds to specific DNA sequences and thereby controls the transfer (or transcription) of genetic information from DNA to mRNA.

The term "transcriptional repressor" refers to proteins that bind to specific sites on DNA and prevent transcription of nearby genes.

The term "transcriptional activator" refers to proteins that bind to specific sites on DNA and enhance transcription of nearby genes.

The term "occupancy" refers to the binding of a transcription factor to its binding site within a gene promoter.

The term "translation" refers the first stage of protein biosynthesis (part of the overall process of gene expression). In translation, messenger RNA (mRNA) produced in transcription is decoded to produce a specific amino acid chain, or polypeptide, that will later fold into an active protein.

The term "ZEB1" refers to the zinc finger E-box binding homeobox 1 gene that encodes a zinc finger transcription factor. This zinc finger transcription factor is also referred to with multiple names such as: AREB6, DELTA-EF12, TCF8, NIL-2A2, and ZFHEP2.

The term "BLIMP-1" refers to the B-lymphocyte-induced maturation protein gene that encodes a transcriptional repressor of gene expression. The protein binds specifically to the PRDI (positive regulatory domain I element) of gene promoters. Transcription of this gene increases upon virus induction. Two alternatively spliced transcript variants that encode different isoforms have been reported. BLIMP-1 is also known as PRDM1 or PRDI-BF1.

The term "NF-κB" refers to the nuclear factor kappa-light-chain-enhancer of activated B cells, a protein complex that controls the transcription of DNA. This protein complex is found in almost all animal cell types and is involved in cellular responses to stimuli such as stress, cytokines, free radicals, ultraviolet irradiation, oxidized LDL, and bacterial or viral antigens. There are five (5) NF-κB family members namely, p65, RelB, c-Rel, p50 and p52.

The term "reporter" refers to a transfected gene that produces a signal, such as luciferase, GFP or β-Galactodidase, when it is expressed; it is typically included in a larger cloned gene that is introduced into an organism to study gene expression.

The term "transfected" refers to the deliberate delivery of nucleic acids into cells.

The term "poly I:C" refers to polyinosinic:polycytidylic acid which is an immunostimulant. It is used in the form of a sodium salt to simulate viral infections. Poly I:C is known to interact with toll-like receptor (TLR) 3. It is structurally similar to double-stranded RNA, which is present in some viruses and is a "natural" stimulant of TLR3. Thus, it can be considered a synthetic analog of double-stranded RNA and is a common tool for scientific research on the immune system.

The term "anti-viral response" refers to the human body's ability to suppress a viral infection by limiting its ability to replicate or inhibits its capability to multiply and reproduce.

The term "asthma" refers to a common chronic inflammatory disease of the airways characterized by variable and recurring symptoms, airflow obstruction, and bronchospasm. Symptoms include wheezing, cough, chest tightness, and shortness of breath. Public attention in the developed world has increased recently because of its rapidly increasing prevalence, affecting up to one quarter of urban children.

The term "colon disease" (for purposes of this application) refers to an inflammatory condition where the inflammatory condition is characterized by an overt production of Th2 cytokines (e.g., IL-13, IL-4, IL-5 etc) in the colon tissue. It is generally believed that the over-production of Th2 cytokines is a result of an insufficient production of IFN-λ1. Exemplary colon diseases include inflammatory bowel disease (such as Crohn's disease and ulcerative colitis), inflammatory bowel syndrome, and inflammation-driven colon cancer.

The term "therapeutically effective amount" means the total amount of each active component of the pharmaceutical composition or method that is sufficient to show a meaningful patient benefit, e.g., amelioration of symptoms of, healing of, or increase in rate of healing of such conditions.

The present inventors surprisingly discovered a novel repressor region on the IFN-λ, promoter. This particular repressor is found on IFN-λ1 promoter located between ~1.2 kb and ~1.6 kb from the IFN-λ1 translation start site. The repressor region has a nucleotide sequence that corresponds with nucleotide 12054025 to nucleotide 12053759 of the IFN-λ1 gene with the Accession No. NT_011109.

The present inventors further discovered three (3) potential ZEB1 binding sites present within the repressor region of the IFN-λ1 promoter. Without wishing to be bound by a theory, it is believed that ZEB1 binding to IFN-λ1 promoter would repress the IFN-λ1 gene activity. This is consistent with our finding that siRNA against ZEB1 mRNA reduces ZEB1 binding to IFN-λ1 promoter (possibly via mRNA degradation pathway) and increases IFN-λ1 gene activity.

Interestingly, the present inventors also found that three (3) potential BLIMP-1 binding sites that are located outside the repressor region of the IFN-λ1 promoter. We demonstrate that siRNA against BLIMP-1 mRNA reduces BLIMP-1 binding to the IFN-λ1 promoter (possibly via the same mRNA degradation pathway) and increases IFN-λ1 gene activity. The utilization of siRNA targeted against ZEB1 and BLIMP-1 mRNAs represent a novel means of regulating IFN-λ1 gene activity.

The present IFN-λ1 reporter constructs have practical research and drug screening applications. An exemplary, but non-limiting application, of the present invention is for a pharmaceutical company to identify a compound that inhibits IFN-λ1 repressor region, and hence increase the production of IFN-λ1 protein.

IFN-λ1 Reporter Constructs and Compound Screening Application

In one embodiment, the study provides a total of seven (7) IFN-λ1 reporter constructs for studying regulatory elements present within the IFN-λ1 promoter. The present IFN-λ1 promoter luciferase constructs including the ~4.0 kb (SEQ ID NO. 1; corresponding with nucleotide 12051212 to nucleotide 12055279 of the IFN-λ1 gene with the Accession No. NT_011109), ~3.5 kb (SEQ ID NO. 2; corresponding with nucleotide 12051862 to nucleotide 12055279 of the IFN-λ1 gene with the Accession No. NT_011109), ~2.2 kb (SEQ ID NO. 3; corresponding with nucleotide 12053168 to nucleotide 12055279 of the IFN-λ1 gene with the Accession No. NT_011109), ~1.8 kb (SEQ ID NO. 4; corresponding with nucleotide 12053526 to nucleotide 12055279 of the IFN-λ1 gene with the Accession No. NT_011109), ~1.6 kb (SEQ ID NO. 5; corresponding with nucleotide 12053759 to nucleotide 12055279 of the IFN-λ1 gene with the Accession No. NT_011109), ~1.2 kb (SEQ ID NO. 6; corresponding with nucleotide 12054085 to nucleotide 12055279 of the IFN-λ1 gene with the Accession No. NT_011109), and ~0.6 kb (SEQ ID NO. 7; corresponding with nucleotide 12054651 to nucleotide 12055279 of the IFN-λ1 gene with the Accession No. NT_011109). The nucleotide sequence of these IFN-λ1 promoter constructs is included in FIG. 2.

In some embodiments, the present invention provides IFN-λ1 reporter constructs for assaying compounds that affects (i.e., inhibit or activate) IFN-λ1 promoter activity. In a preferred embodiment, the reporter constructs comprise specific restriction endonuclease sites that are not overlapping with putative transcriptional sites (e.g., NF-κB, IRF etc; see FIG. 9). A portion of the IFN-λ1 gene promoter is linked to a reporter gene (e.g., luciferase, green fluorescent protein, beta-galactosidase, and the like) to prepare a reporter construct. The linking of a gene promoter to a reporter gene can be achieved through DNA ligation and such methodology is well known to those skilled in the art. Exemplary IFN-λ1 reporter constructs of the present invention are described in FIG. 4 and illustrative examples are detailed below.

Suitable plasmids include the pGL4.10-IFN-λ1-4 kb plasmid. The pGL4.10 plasmid backbone (Promega, Madison, Wis.) contains various restriction enzymes necessary for the IFN-λ1 gene fragment insertion. Other suitable plasmid backbones are known to those skilled in the art and may be utilized in the methods of the present invention. Examples of other vectors suitable for use with the present application include, but are not limited to, the standard transient reporter vectors such as pGLUC-basic (New England Biolabs, Ipswich, Mass.) or pGL4.23 (Promega, Madison, Wis.), standard stable reporter vectors such as pGL4.14 (Promega, Madison, Wis.), adenoviruses such as AD-CMV-LUC (Vector Biolabs, Philadelphia, Pa.), or lentivirus-based vectors such as pLVX-DD-ZSGREEN (Clontech, Mountain View, Calif.), and the like.

In an embodiment, reporter constructs of the present invention are inserted into a cell through transfection. Transfection includes transiently or stably expressing the IFN-λ1 reporter constructs. The methodology for transient transfection and stable transfection is well recognized to those ordinary skills in the art.

In preferred embodiments of the present invention, the reporter constructs of the present invention exhibit an increase of reporter gene activity (e.g., fluorescence) when specific IFN-λ1 reporter constructs are used. For example, the use of the ~1.2 kb (SEQ ID NO: 6) and ~1.6 kb (SEQ ID NO: 5) reporter constructs permits possible identification of inhibitor(s) that remove the repressor's activity present on the IFN-λ1 promoter. The use of other IFN-λ1 reporter constructs (i.e., the ~4.0 kb, ~3.5 kb, ~2.2 kb, ~1.8 kb, ~1.6 kb or ~0.6 kb reporters) permits the identification of activator(s) that increases IFN-λ1 promoter activity. The application of a screening system is further illustrated in examples below.

The methods of the present invention are suitable for screening compounds that may have inhibitory or enhancing activity towards the IFN-λ1 promoter. The test compounds of the present invention can be obtained by a combinatorial library method known in the art, including biological libraries; peptide libraries (libraries of molecules having the functionalities of peptides etc. The biological library and peptide library approaches are preferred for use with peptide libraries, while other library includes small molecule libraries of compounds as known by one skill in the art.

siRNA

It is generally considered that a major mechanism for siRNA in mammalian cells is mRNA degradation. Without wishing to be bound by a theory, it is believed that the present siRNA, when bound to the target mRNA (e.g., ZEB1 mRNA or BLIMP-1 mRNA), leads to mRNA incorporation into a siRNA-RISC complex and subsequent mRNA degradation within P-bodies of the cytoplasm. Therefore, the present siRNA is expected to lead to a decrease in steady-state mRNA for ZEB1 or BLIMP-1. Consequently, the siRNA would reduce the binding of ZEB1 or BLIMP-1 to the IFN-λ1 promoter. The reduced binding of a transcriptional factor is expected to affect its gene activity.

Complete complementary (100%) between siRNA and its target is preferred, but not required. For example, it may be 90-95% complementary. For purposes of this application, it is intended to cover a siRNA against ZEB1 mRNA and BLIMP-1 mRNA, insofar as it possesses an ability to reduce the steady-state mRNA for ZEB1 or BLIMP-1 (as measured by qPCR) and binding of ZEB1 or BLIMP-1 to IFN-λ1 promoter (as measured by ChIP assay). According to the present bioinformatics study, there are three (3) ZEB1 binding sites and three (3) BLIMP-1 binding sites present on IFN-λ1 promoter. The three (3) ZEB1 binding sites are all present within the repressor region (i.e., ~1.2 kb to ~1.6 kb) (see, FIG. 11, and Example 12). The three (3) BLIMP-1 binding sites are all present outside the repressor region (see, FIG. 12, and Example 13). It is noted that the reduced transcriptional factor binding would lead to an increase in IFN-λ1 gene activity as manifested by an increase in IFN-λ1 mRNA (as measured by qPCR or Northern blot) or IFN-λ1 protein (as measured by Western blot or ELISA).

The present siRNA exhibits sequence specificity in reducing ZEB1 or BLMP1 binding to IFN-λ1 promoter and hence increases the production of IFN-λ1 protein. These properties make siRNA (against ZEB1 and BLIMP-1 mRNA) a potentially valuable tool for increasing IFN-λ1 gene expression and drug target validation. Moreover, siRNAs against these transcriptional factors are potentially useful as therapeutic agents against: (1) diseases that are caused by under-expression of IFN-λ1 gene; and (2) diseases brought about by over-expression of other cytokines that act secondarily on the repressor region of the IFN-λ1 gene.

In one embodiment, the present invention provides a method for gene silencing against transcription factors that bind within the repressor region on IFN-λ1 promoter. This is achieved by permitting selection of an optimal siRNA. A siRNA selected according to the present invention may be used individually, or in conjunction with other siRNAs, each of which may has its activity. The combination could thus maximize their efficiency to increase IFN-λ1 gene activity.

The degree to which it is possible to select a siRNA against the ZEB1 or BLIMP-1 mRNA that maximizes these criteria will depend, in part, on the nucleotide sequence of the ZEB1 and BLIMP-1 mRNAs. The present method requires a siRNA at least partially complementary to the ZEB1 mRNA or BLIMP-1 mRNA. As described supra, while the siRNA complementarity is not absolute (i.e., complete complementarity between siRNA and mRNA of the transcriptional factor is not required), in some instances, up to ~5 mismatched bases in a 20-mer oligonucleotide may be tolerated. One skilled in the art would recognize that insofar as there is substantial complementarity between siRNA and the mRNA for ZEB1 or BLIMP-1 so as to allow siRNA to reduce binding of ZEB1 or BLIMP-1 to IFN-λ1 promoter and increases IFN-λ1 protein production, such siRNA is encompassed by the present invention. The present invention provides detailed protocols for one skilled artisan to assay ZEB1 and BLIMP-1 binding to IFN-λ1 promoter. For example, a ChIP assay may be used to determine the binding. The present invention also provides a method of quantifying a change in IFN-λ1 gene activity (i.e., increase or decrease) by qPCR to determine steady-state IFN-λ1 mRNA, as well as ELISA or Western blot to quantify the amount of expressed IFN-λ1 protein. The methodologies are included in the "Materials and Methods."

In another embodiment, the present invention provides a pool of at least two siRNAs. The pool may be present in the form of a kit or therapeutic reagent, wherein each siRNA represents an anti-sense strand complementary to a portion of the ZEB1 or BLIMP-1 mRNA. Most preferably, each siRNA is 15-30 base pairs in length, and one strand of each of the siRNAs is 100% complementary to a portion of the target mRNA. In a preferred embodiment, a pool of four (4) siRNAs is used to silence ZEB1 mRNA or BLIMP-1 mRNA.

The present method also encompasses the use of an increased number of siRNAs directed to a target (e.g., ZEB1 or BLIMP-1). For example, one skilled in the art would appreciate the use of a pool or a kit of siRNAs (e.g., four (4) siRNAs). The use of multiple siRNA is expected to increase the likelihood of success in reducing target mRNA levels. This may be benefited by an additive or synergistic effect of the siRNA pool. When a siRNA directed against an mRNA does not have a satisfactory level of functionality, if combined in a pool of siRNAs, together they may act additively or synergistically to promote mRNA degradation and increase IFN-λ1 promoter activity. The use of multiple siRNAs in the present method increases the probability of silencing the target mRNA, and improves the economics of operation (as compared to adding individual siRNA).

The present invention provides different pools of siRNA against various components of NF-κB. In one embodiment, the present invention provides a pool of four siRNA oligonucleotides (e.g., which consists of SEQ ID NOs: 40, 41, 42, and 43) against NF-κB p50 so as to increase the mRNA expression of the IFN-λ1 gene and OAS1 gene. NF-κB p50 mRNA has a nucleotide sequence set forth in Accession No: NM_003998. In another embodiment, the present invention provides a pool of four siRNA oligonucleotides (e.g., which consists of SEQ ID NOs: 44, 45, 46, and 47) against NF-κB p65. NF-κB p65 mRNA has a nucleotide sequence set forth in Accession No: NM_021975. The various pools may be present in the form of a kit containing therapeutic reagents, wherein each siRNA represents an anti-sense strand complementary to a portion of the NF-κB p50 or p65 mRNA. More preferably, siRNA is 15-30 base pairs in length, and the siRNA strand is 100% complementary to a portion of the target mRNA. Specifically, a pool of four (4) siRNAs is used to silence NF-κB p50 mRNA or NF-κB p65 mRNA.

It is a surprising finding that siRNA against NF-κB p50 increases IFN-λ1 gene expression in airway and colon epithelial cells. In contrast, siRNA against NF-κB p65 decreases IFN-λ1 gene expression in airway and colon epithelial cells. siRNA against RelB did not alter IFN-λ1 gene expression, illustrating specificity. RelB mRNA has a nucleotide sequence set forth in Accession No: NM 006509. Exemplary siRNAs against RelB consist of SEQ ID NOs: 48, 49, 50, and 51. siRNA against different subunits of the NF-κB family exert a differential effect on IFN-λ1 gene expression in airway and colon epithelial cells. This is the first report regarding siRNA's effect on various subunits of the NF-κB family in regulation of IFN-λ1 gene expression.

In one embodiment, the present invention provides a method of increasing expression of IFN-λ1 protein in an airway epithelial cell, comprising the steps of: i) providing an airway epithelial cell in need thereof; and ii) exposing a siRNA oligonucleotide targeted against the EVI1 or CRX transcription factor mRNA to said airway epithelial cell, thereby increasing the IFN-λ1 protein expression by said airway epithelial cell, wherein said EVI1 mRNA has a nucleotide sequence set forth in Accession No: NM_001105077. CRX mRNA has a nucleotide sequence set forth in Accession No: NM_000554.

In one embodiment, the present invention provides a method of decreasing expression of IFN-λ1 protein in a airway epithelial cell, comprising the steps of: i) providing an airway epithelial cell in need thereof; and ii) exposing a siRNA oligonucleotide targeted against the GATA1 transcription factor mRNA to said airway epithelial cell, thereby increasing the IFN-λ1 protein expression by said airway epithelial cell, wherein said GATA1 mRNA has a nucleotide sequence set forth in Accession No: NM_002049.

In yet one embodiment, the present invention provides a method of increasing expression of IFN-λ1 protein in a colon epithelial cell, comprising the steps of: i) providing a colon epithelial cell in need thereof; and ii) exposing a siRNA oligonucleotide targeted against the ZEB1 transcription factor mRNA to said colon epithelial cell, thereby increasing the IFN-λ1 protein expression by said colon epithelial cell, wherein said ZEB1 mRNA has a nucleotide sequence set forth in Accession No: NM_030751 or Accession No: NM_001128128.

Preferably, exemplary siRNA oligonucleotide targeted against ZEB1 mRNA consists of SEQ ID NO: 12, SEQ ID NO: 13, SEQ ID NO: 14, and SEQ ID NO: 15. Preferably, the increased IFN-λ1 protein expression is measured by an increase in IFN-λ1 protein secretion. More preferably, the increased IFN-λ1 protein expression is measured by an ELISA.

The present invention provides a method of increasing expression of IFN-λ1 protein in a colon epithelial cell or an airway epithelial cell.

In one embodiment, the present invention provides a method of treating a human subject afflicted with a colon disease, comprising the step of administering a therapeutically effective amount of a siRNA oligonucleotide to the human subject. The siRNA oligonucleotide is targeted against ZEB1 mRNA, and induces the production of an IFN-λ1 protein having an amino acid sequence set forth in GenBank Accession No. NP_742152, and wherein said ZEB1 mRNA has a nucleotide sequence set forth in GenBank Accession No: NM_030751 or GenBank Accession No: NM_001128128. Preferably, exemplary siRNA oligonucleotide is at least one oligonucleotide selected from the group consisting of SEQ ID NO: 12, SEQ ID NO: 13, SEQ ID NO: 14, and SEQ ID NO: 15.

The siRNAs of the present invention may be modified. Modified siRNAs include altering the natural structures of a nucleic acid. For example, siRNAs may include altering the phosphodiester linkage, sugars (ribose for RNA and deoxyribose for DNA) and purine/pyrimidine bases, and the siRNAs may include one or more chemical modifications described herein. Modifications can be made to an oligonucleotide insofar as they retain ability to hybridize to the target nucleic acid.

Preferably, modifications of the phosphodiester linkage render siRNAs more stable against nucleases, as well as enhancing cellular uptake and bioavailability. Modified phosphodiester linkages include phosphorothioate, methylphosphonate, phosphorodithioate, or boranophosphate linkages. The siRNAs of the present invention may contain all of these modified linkages, including a mixture of different modified linkages and unmodified linkages. The synthesis of the modified siRNAs is recognized by one of the ordinary skill in the art.

In one embodiment, modification of siRNA includes the incorporation of modified sugar groups such as alpha-anomers or the sugars incorporated into 2'-O-methyloligonucleotides to protect the siRNA from nuclease degradation.

In one embodiment, modification of siRNA includes linkage of a chemical group to the siRNA. The linkage is preferably through a covalent bond. An exemplary chemical group includes, for example, steroids, or a lipid-based hydrophobic group (i.e., cholesterol). The chemically modified siRNAs exhibit an increased circulation time in the body of a mammal. Such increased circulatory time is expected to facilitate uptake of siRNA by the mammalian cells.

Also contemplated in the present invention are the modifications of the nucleotide purine or pyrimidine bases. Naturally-occurring nucleobases include the purine bases adenine (A) and guanine (G), and the pyrimidine bases thymine (T), cytosine (C) and uracil (U). Modified nucleobases include, but not limited to, synthetic and natural nucleobases (such as 5-methylcytosine, 5-hydroxymethyl cytosine, xanthine, hypoxanthine, 2-aminoadenine, 2-thiouracil, 2-thiothymine, 2-thiocytosine, 5-propynyl uracil, 6-azo uracil, cytosine and thymine, 5-uracil, 4-thiouracil, 5-halo, particularly 5-bromo, 5-trifluoromethyl, 7-methyl- guanine, 7-methyladenine, 8-azaguanine, 8-azaadenine, 7-deazaguanine, 7-deazaadenine, 3-deazaguanine, 3-deazaacdenine and the like).

The siRNA compounds used in accordance with this invention may be conveniently and routinely made through the well-known technique of solid phase synthesis. For example, equipment for such synthesis is sold by several vendors including, for example, Applied Biosystems (Foster City, Calif.). Other means for such synthesis known in the art may also be employed. It is well known to use similar techniques to prepare oligonucleotides such as the phosphorothioates and alkylated derivatives.

The present invention encompasses an optimal length of the siRNAs that function to induce degradation of transcriptional factors (e.g., ZEB1 or BLIMP-1) and thereby reduce binding to IFN-λ1 promoter. Preferably, the siRNAs are about 10 to 50 nucleotides in length. Preferably, the siRNAs are about 15 to 30 nucleotides in length, and more preferably about 15 to 22 nucleotides in length. The length of siRNAs may conveniently be optimized. For example, the optimization is achieved by determining the expression of the IFN-λ1 promoter using, for example, the QPCR assay described herein. The presence of a modification in the siRNAs may influence the optimal length and the overall efficiency of the siRNA oligonucleotides.

Several factors may be taken into consideration when it comes to optimization of the siRNA length. Shorter siRNAs may have the advantage of being more easily internalized by cells. However, if they are less than 10 nucleotides in length, they may not form a stable hybrid with the target sequence. On the other hand, longer siRNAs (e.g., greater than 100 nucleotides in length) may stably hybridize to their target sequence but may not be efficiently taken up by cells or may be cytotoxic.

siRNA Pharmaceutical Composition and Clinical Application

The present invention further provides a pharmaceutical composition for alleviating viral infection or asthma in a subject and comprises a siRNA oligonucleotide targeted against ZEB1 mRNA or BLIMP-1 mRNA and a pharmaceutically acceptable carrier.

Pharmaceutically acceptable carrier encompasses any standard pharmaceutical carriers. The present pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for airway administration include aerosol inhalation, intranasal application, intratracheal installation, or insufflation.

Aerosol preparation is well known by one skilled in the art and may be in the form of liquid drops in gaseous medium or suspensions of solid material. There are three (3) commonly used aerosol delivery methods: namely, nebulizers, metered-dose inhalers (MDI) and dry powder inhalers (DPI). Preferably, the siRNA would be delivered using a pulmonary MDI with a hydrofluoroalkane (HFA) propellant. Other suitable aerosol delivery methods may be used as well.

Examples of pharmacologically acceptable carriers include aqueous solutions such as water, saline, or buffers solutions. Delivery vehicles include, for example, saline, liposomes, microspheres, or surfactant. Delivery vehicles can be utilized to enhance in vivo stability. In a preferred embodiment, saline can be used as a delivery vehicle because of its demonstrated ability to mediate siRNA delivery to the lung, and minimal toxicity, and ability to be delivered in a metered-dose inhaler. siRNA-saline suspensions may be made by a variety of techniques known in the art. These methods generally involve first synthesizing the siRNA and dissolving it in saline. In an embodiment, the pharmaceutical composition is suitable for administering a nasal route to a subject. An example includes aerosolized siRNA-saline droplets for intranasal inhalation.

The exact dosage and number of doses of the pharmaceutical compositions described herein depends upon several factors such as the disease indication, the route of administration, the delivery vehicle and the siRNA oligonucleotide composition. Duration of treatment will depend on the effects of the treatment on the disease symptoms, and may include multiple daily doses for extended periods of time.

The present method of using siRNAs against ZEB1 mRNA or BLIMP-1 mRNA may be used to alleviate or treat IFN-λ1-associated inflammatory diseases or immune disorders. Non-limiting examples of IFN-λ1-associated inflammatory diseases or immune disorders that can be treated or prevented include, but are not limited to, viral infection, Crohn's disease, intrinsic asthma, allergic asthma, graft-versus-host disease, and allergy such as, atopic allergy and the like. Preferred diseases or disorders that can be treated by administration of siRNAs, include airway inflammation, pulmonary exacerbations due to allergy, viral infection, or bacterial infections in same.

In one embodiment, pharmaceutical compositions comprising siRNAs may be administered in combination therapy, i.e., combined with another therapeutic agent such as steroid or other anti-inflammatory molecules including corticosteroids (e.g. budesonide or fluticasone), short-acting β-agonists (e.g., albuterol or terbutaline), long-acting β-agonists (e.g., formoterol or salmeterol) and the like. The combined compositions are useful for treating immune disorders or inflammatory diseases (such as asthma or airway inflammation). The term "in combination" in this context means that the agents may be given substantially contemporaneously, either simultaneously or sequentially.

The present invention will be better understood from the following experimental studies. One of ordinary skill in the art would readily appreciate that the specific methods and results discussed therein are not intended to limit the invention. The experimental studies merely serve illustrative purposes, and the invention is more fully described by the claims that follow thereafter.

EXPERIMENTAL STUDIES

Example 1

Cloning of IFN-λ1 Promoters

We studied the genomic structure of the IFN-λ1 promoter and the role of transcriptional regulation in IFN-λ1 promoter. Onoguchi et al. in 2007 prepared a promoter construct containing a ~600 bp IFN-λ1 promoter linked to a minimal promoter of IFN β gene (i.e., containing a TATA element). Using the hybrid promoter construct, Onoguchi et al. showed that transcriptional sites (NF-κB and IRF) are involved in IFN-λ1 promoter regulation following stimulation with a mouse virus (i.e., Newcastle disease virus) (Onoguchi et al., 2007). The hybrid promoter, while yielding limited information about IFN-λ1 transcription; nevertheless it does not represent the authentic IFN-λ1 promoter. It should be noted that the ~600 bp IFN-λ1 promoter simply cannot account for the complex IFNλ1 gene regulation.

Figure 1:
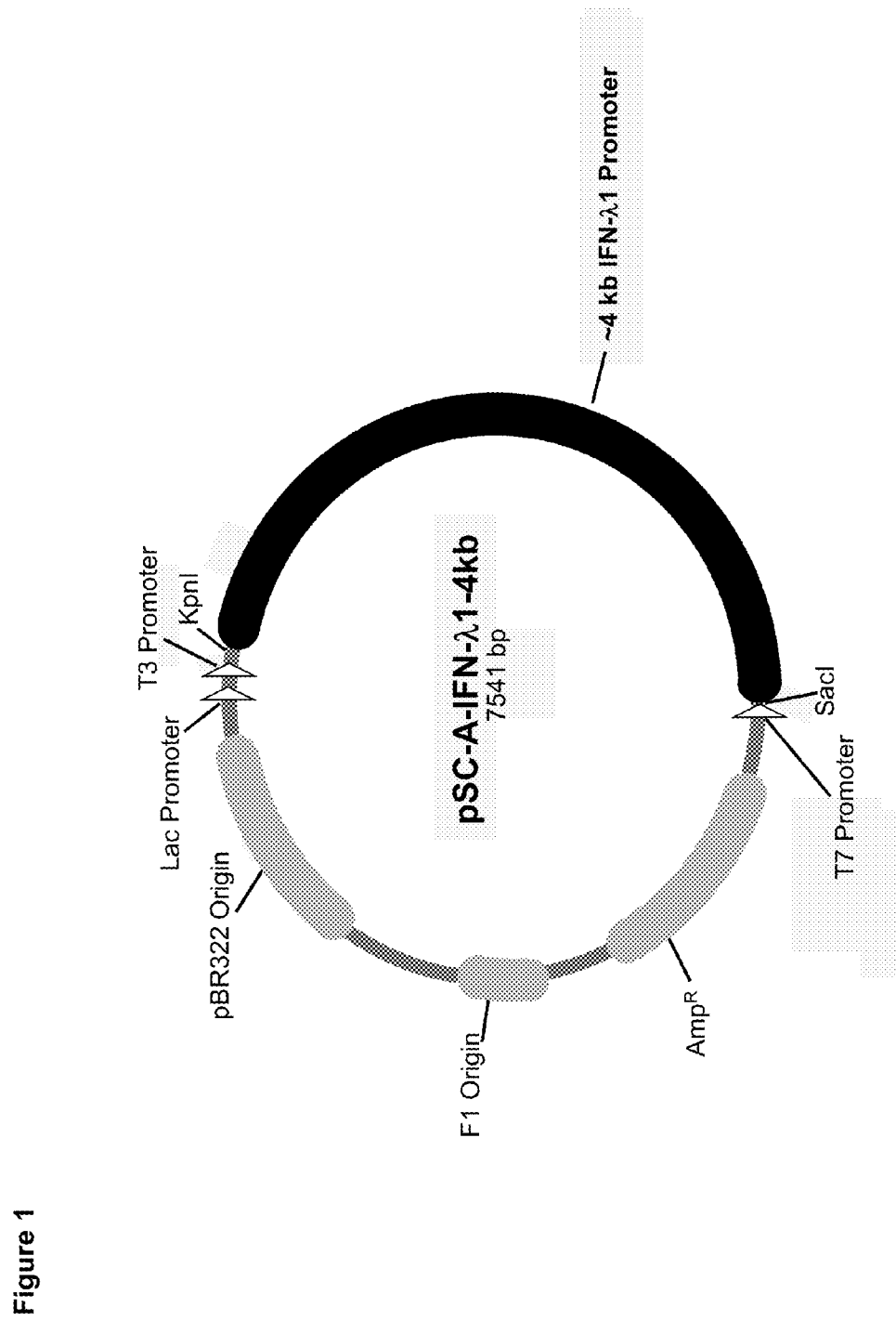
FIG. 1 depicts a schematic representation of the pSC-A-IFN-λ1-4 kb plasmid. This plasmid is 7,541 bp in length and contains 4,068 bp upstream of the IFN-λ1 coding gene region (~4 kb IFN-λ1 promoter) (Black). Additional features of the pSC-A vector (Invitrogen) are indicated, including the Kpn1 and Sac1 restriction sites.

In this study, we first prepared an IFN-λ1 promoter construct upstream from that of the IFN-λ1 translation start site (i.e., ATG). We used PCR approach with a specific primer pair (SEQ ID NOs: 16 and 17) (See, Table 1) designed to amplify nucleotide positions 12051212-12055279 of the IFN-λ1 gene with the GenBank Accession Number, NT_011109.15. The cloned DNA consisted of a promoter fragment containing ~4 kb that is upstream of the IFN-λ1 translational start site (i.e., ATG). The amplified ~4 kb promoter fragment was purified using a gel extraction protocol. We then used TA-cloning (Invitrogen) to insert the amplified ~4 kb promoter fragment into the pSC-A vector backbone (FIG. 1).

Example 2

Nucleotide Sequence of the ~4 kb IFN-λ1 Promoter Fragment

The ~4 kb promoter fragment was sequence-verified. We used multiple primers directed against the forward and reverse strands using the DTCS Quick Start method performed on a CEQ 8000 Genomic Analyzer (Beckman Coultier). We compared the nucleotide sequence of the ~4 kb promoter fragment with the nucleotide sequence of the IFN-λ1 gene (GenBank Accession Number, NT_011109) and verified that there were no mutations introduced through PCR cloning. The nucleotide sequence (SEQ ID NO: 1) of our ~4 kb IFN-λ1 promoter fragment is listed in FIG. 2.

Example 3

Cloning of a Luciferase Reporter Construct Containing the ~4 kb IFN-λ1 Promoter

Figure 3:
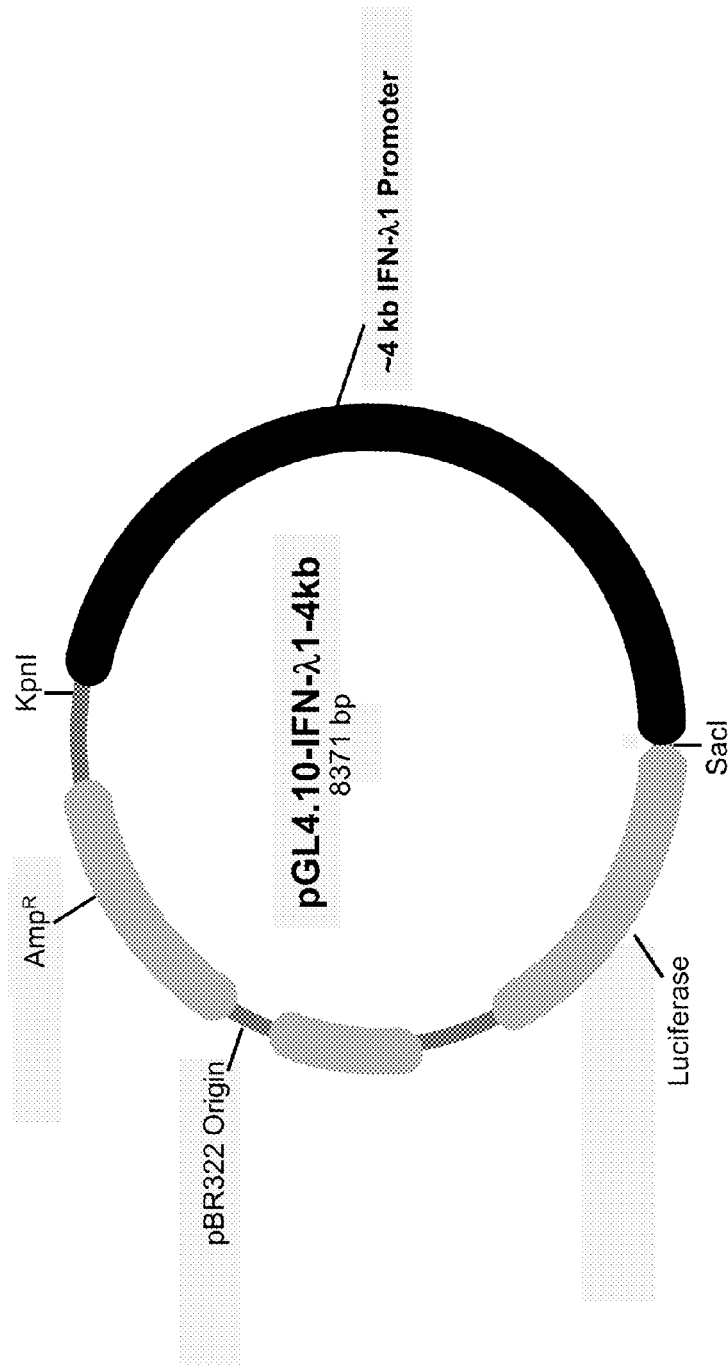
FIG. 3 depicts a schematic representation of the pGL4.10-IFN-λ1-4 kb plasmid. This plasmid is 8,371 bp in length and contains 4,066 bp upstream of the IFN-λ1 coding gene region (~4 kb IFN-λ1 promoter) (Black). The ~4 kb IFN-λ1 promoter was sub-cloned into the pGL4.10 vector backbone from the pSC-A-IFN-λ1-4 kb plasmid (described in FIG. 1) using the Kpn1 and Sac1 restriction enzyme sites.

In this study, we sub-cloned the ~4 kb IFN-λ1 promoter fragment into a luciferase reporter construct (i.e., pGL4.10 luciferase reporter which contains solely the luciferase coding region and no regulatory elements) (FIG. 3). We used restriction endonucleases Kpn1 and Sac1 for the sub-cloning. The resulting luciferase reporter construct containing the ~4 kb IFN-λ1 promoter fragment is named pGL4.10-IFN-λ1-4 kb plasmid. (FIG. 3)

Example 4

~4 kb IFN-λ1 Promoter Luciferase Construct Responds to Viral Infection

In normal epithelial cells, viral infection leads to IFN-λ1 gene activation (Brand et al., 2005; Ank et al., 2008; Sommereyns et al., 2008). The IFN-λ1 gene promoter is believed to be upregulated in response to viral infection. We examined the prepared full-length IFN-λ1 promoter fragment to determine if it responds to viral infection. In this study, we first transfected the pGL4.10-IFN-λ1-4 kb plasmid into human airway epithelial cells (i.e., BEAS-2B cells from ATCC). At 16-hours post-transfection, we treated the transfectant cells with poly I:C in order to mimic viral infection as a model.

Figure 5:
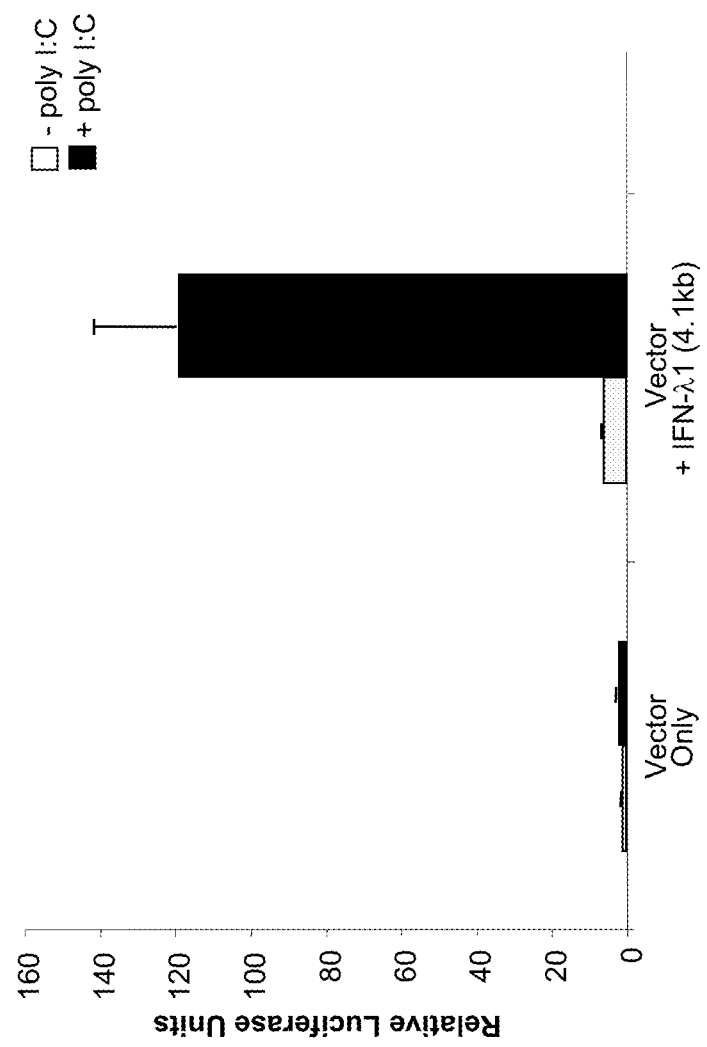
FIG. 5 depicts that the ~4 kb IFN-λ1 reporter construct responsive to viral infection. Human airway BEAS-2B cells were transfected with the ~4 kb IFN-λ1 reporter construct (vector+IFN-λ1 4.0 kb) (SEQ ID NO: 1) or vector control (vector alone) and stimulated with poly I:C (a mimic of viral infection) or medium alone for 3 hours prior to performing a luciferase assay. Data from three (3) replicate experiments were averaged. Means (+/−SEM) are shown.

We monitored the IFN-λ1 gene promoter activity using the luciferase assay detailed in "Materials & Methods" (infra). Transfected cells were treated with 50 µg/ml poly I:C for ~3 hours, and controls included media alone. BEAS-2B cells transfected with the pGL4.10-IFN-λ1-4 kb plasmid had a 15-20 fold increase in luciferase activity (FIG. 5). In contrast, pGL4.10 plasmid alone had minimal activity (FIG. 5). These data indicate that the ~4 kb IFN-λ1 promoter fragment can regulate IFN-λ1 gene transcription following viral infection.

Example 5

Figure 6B:
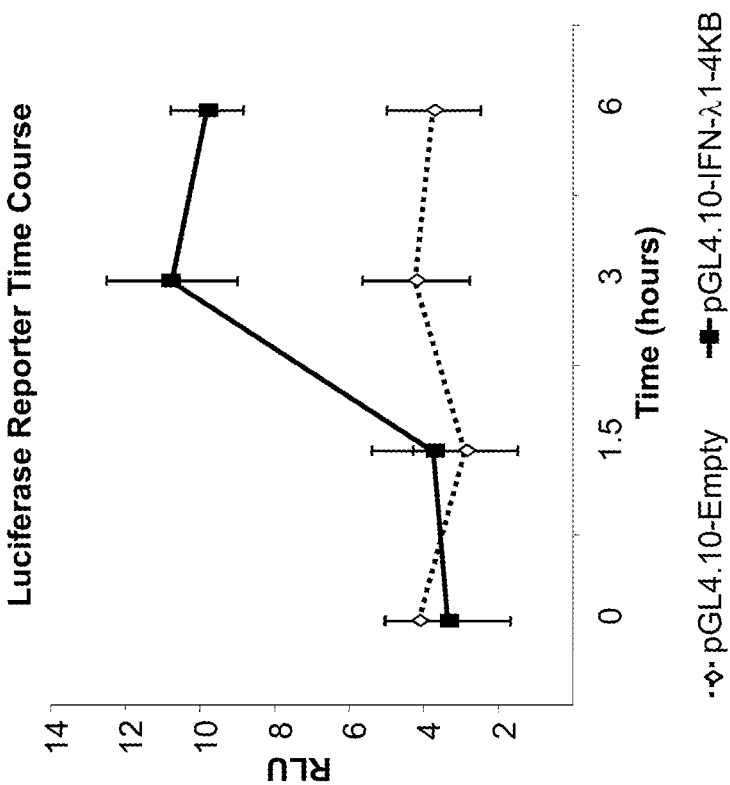
FIG. 6B depicts the time course of ~4 kb IFN-λ1 reporter gene activation in transfected BEAS-2B cells following poly I:C challenge. BEAS-2B cells were first transfected with pGL4.10 vector or pGL4.10-IFN-λ1-4 kb. The transfected cells were challenged with poly I:C for 1.5, 3, or 6 hours. The ~4 kb IFN-λ1 reporter gene activity was monitored by a luciferase assay. The ~4 kb IFN-λ1 reporter gene activity peaked at 3-6 hours.
Figure 6A:
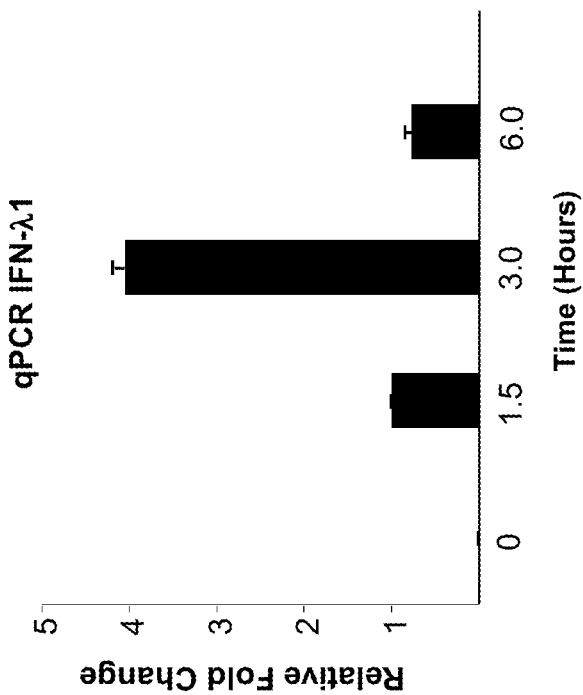
FIG. 6A depicts the time course of IFN-λ1 mRNA expression in BEAS-2B cells following poly I:C challenge. BEAS-2B cells were treated with poly I:C for 1.5, 3 or 6 hours. Total cellular RNA was isolated from BEAS-2B cells. qRT-PCR was performed to quantify mRNA expression of IFN-λ1. IFN-λ1 mRNA expression peaked at 3 hours post-poly I:C challenge.

IFN-λ1 Gene in Untransfected Cells and IFN-λ1 Promoter Construct (~4 kb) in Transfected Cells Behave Similarly to Viral Infection In this study, we compared the virally-induced gene response in the naïve BEAS-2B cells (i.e., non-transfected BEAS-2B) as to that in the BEAS-2B cells transfected with the ~4 kb IFN-λ1 promoter construct (SEQ ID NO: 1). Viral stimulation was mimicked by poly I:C challenge. IFN-λ1 mRNA expression in naïve BEAS-2B cells was monitored by qPCR. Specific primer sets against IFN-λ1 gene were used (SEQ ID NOs: 18 and 19) (see Methods). The ~4 kb IFN-λ1 promoter construct activity was monitored by luciferase activity. As shown in FIG. 6A, IFN-λ1 mRNA expression peaked at 3 hours of poly I:C challenge. Similarly, the luciferase activity increased in the transfected BEAS-2B cells (containing the ~4 kb IFN-λ1 promoter construct) following poly I: C challenge and peaked at 3 hours (FIG. 6B). These data indicate that the ~4 kb IFN-λ1 promoter construct behaves similarly as to the IFN-λ1 gene in the naïve cells (both exhibited a similar temporal relationship for its promoter activity following viral stimulation).

Example 6

Additional IFN-λ1 Promoter Constructs (~3.5 kb, ~2.2 kb, ~1.8 kb, ~1.6 kb, ~1.2 kb, and ~0.6 kb)

So far, we have established that the ~4 kb IFN-λ1 promoter activity is increased in response to viral infection and that the construct behaves similarly to that of the naïve IFN-λ1 gene. In this study, we sought to determine the minimal region on the IFN-λ1 promoter required for viral response. We also wanted to identify the respective role of the putative transcriptional sites present on this IFN-λ1 promoter region. To do so, we first took the initiative to generate additional IFN-λ1 promoter constructs (in addition to the ~4 kb IFN-λ1 promoter construct).

A) Cloning of Additional IFN-λ1 Promoter Constructs

We cloned six (6) additional IFN-λ1 promoter luciferase reporter constructs with various IFN-λ1 promoter lengths from ~3.5 kb to ~0.6 kb. We digested the pGL4.10-IFN-λ1-4 kb plasmid with various restriction enzymes to generate the ~3.5 kb to ~0.6 kb IFN-λ1 promoter lengths. The ~3.5 kb IFN-λ1 promoter construct (SEQ ID NO: 2) was generated using restriction enzymes KpnI and BsaxI. The ~2.2 kb IFN-λ1 promoter construct (SEQ ID NO: 3) was generated using restriction enzymes KpnI and NdeI. The ~1.8 kb IFN-λ1 promoter construct (SEQ ID NO: 4) was generated using restriction enzymes KpnI and XcmI. The ~1.6 kb IFN-λ1 promoter construct (SEQ ID NO: 5) was generated using restriction enzymes KpnI and StuI. The ~1.2 kb IFN-λ1 promoter construct (SEQ ID NO: 6) was generated using restriction enzymes KpnI and BbsI. The ~0.6 kb IFN-λ1 promoter construct (SEQ ID NO: 7) was generated using restriction enzymes KpnI and XmnI.

B) Preparation of Additional IFN-λ1 Promoter Luciferase Reporter Constructs

Figure 4:
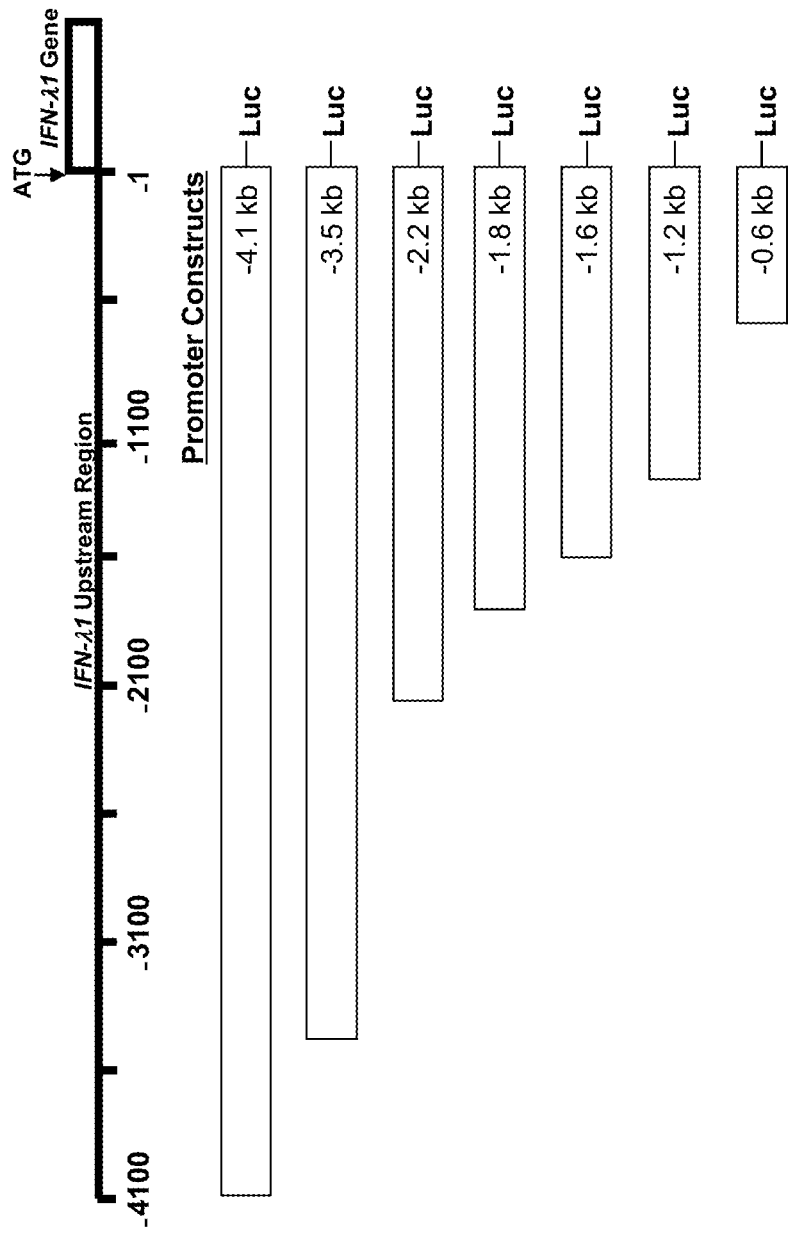
FIG. 4 depicts a schematic representation of a total of seven (7) IFN-λ1 promoter Luciferase (Luc) reporter constructs (reporter construct). Each of these reporter constructs contains an IFN-λ1 promoter fragment (from ~4 kb to ~0.6 kb in length upstream of the IFN-λ1 translation start site (i.e., ATG)) that is fused with the Luc reporter gene.

As shown in FIG. 4, the prepared luciferase reporter constructs carried various IFN-λ1 promoter fragments. These fragment sizes were carefully selected using specific restriction endonuclease sites that were not overlapping with putative transcriptional sites (e.g., NF-κB, IRF etc) (See, FIG. 9).

Table 1 summarizes the prepared additional IFN-λ1 promoter luciferase constructs including the ~3.5 kb, ~2.2 kb, ~1.8 kb, ~1.6 kb, ~1.2 kb, and ~0.6 kb IFN-λ1 promoter (upstream from translation start codon). The nucleotide sequence of these IFN-λ1 promoter constructs is included in FIG. 2. The SEQ ID numbers for these constructs are also indicated.

TABLE 1

IFN-λ1 Promoter Constructs Used In This Study

| Designation | Nucleotides | SEQ ID NO: |
|---|---|---|
| IFN-λ1 (−4.0 kb) | 1-4068 | 1 |
| IFN-λ1 (−3.5 kb) | 651-4068 | 2 |
| IFN-λ1 (−2.2 kb) | 1957-4068 | 3 |
| IFN-λ1 (−1.8 kb) | 2314-4068 | 4 |
| IFN-λ1 (−1.6 kb) | 2548-4068 | 5 |
| IFN-λ1 (−1.2 kb) | 2874-4068 | 6 |
| IFN-λ1 (−0.6 kb) | 3439-4068 | 7 |

Example 7

The ~0.6 kb IFN-λ1 Promoter Construct Failed to Respond to Viral Stimulation

Onoguchi et al. initially reported that the ~600 bp upstream IFN-λ1 promoter fragment is functional following viral challenge. Using the prepared ~0.6 kb IFN-λ1 promoter construct (SEQ ID NO: 7), we examined if this ~600 bp IFN-λ1 promoter fragment can respond to viral stimulation using poly I:C as a model for viral infection.

To our surprise, the ~0.6 kb IFN-λ1 promoter construct failed to respond to poly I:C challenge in our assay as there was a lack of luciferase activity observed (see FIG. 7). Note that the positive control (SV40 promoter) had high luciferase activity, indicating that both the vector and luciferase assay were functional. Our present finding is contrary to that of Onoguchi. We observed a lack of promoter activity for the ~0.6 kb IFN-λ1 promoter construct. The basis for the difference is unknown. Onoguchi et al. used an artificial promoter element (e.g., TATA) and showed IFN-λ1 regulation via one NF-κB and two IRF transcriptional sites when challenged with NewCastle disease virus (Onoguchi et al., 2007).

Example 8

A Novel Activation Region on the IFN-λ1 Promoter (Between ~0.6 kb to ~1.2 kb Upstream)

Because the ~0.6 kb IFN-λ1 promoter construct was found to fail in response to viral stimulation, we continued to examine upstream regions of the IFN-λ1 promoter (i.e., beyond the ~0.6 kb region) required for the viral response.

Figure 8:
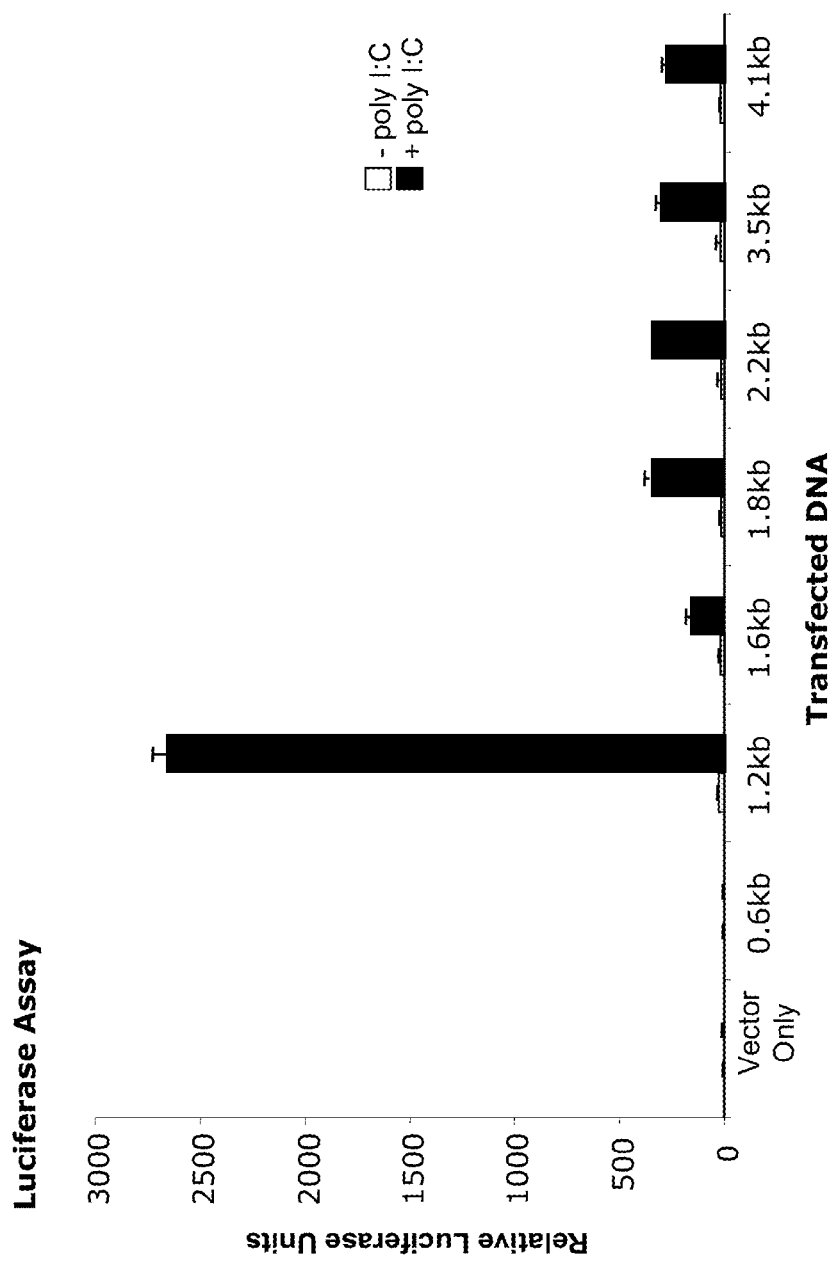
FIG. 8 depicts the luciferase activity of the seven (7) IFN-λ1 reporter constructs. BEAS-2B cells were first transfected with an IFN-λ1 reporter construct (~0.6 to ~4.0 kb) or vector alone. The transfectant cells were challenged with poly I:C (to mimic viral infection) for 3 hours. Data from three (3) replicate experiments were averaged and means (+/−SEM) are shown. Note that the 1.2 kb IFN-λ1 reporter construct has the highest luciferase activity, whereas the 1.6 kb, 1.8 kb, 2.2 kb, 3.5 kb, and 4.0 kb IFN-λ1 reporter constructs exhibited a modest increase (statistically significant) in luciferase activity. The 0.6 kb IFN-λ1 reporter construct had no change in luciferase activity.

In this study, we chose the five (5) additional IFN-λ1 promoter constructs having a length of ~1.2 kb to ~3.5 kb. BEAS-2B cells were transfected the IFN-λ1 promoter constructs (i.e., ~0.6 kb, ~1.2 kb, ~1.6 kb, ~1.8 kb, ~2.2 kb, ~3.5 kb or ~4.0 kb), followed by poly I:C challenge. A ~60 fold increase in luciferase activity was observed when the ~1.2 kb IFN-λ1 promoter construct was used (FIG. 8). Note that there was minimal luciferase reporter activity for the ~0.6 kb IFN-λ1 promoter construct (FIG. 8). This suggests that a novel activation region between ~0.6 kb and ~1.2 kb upstream of the IFN-λ translation start site (i.e., ATG). The activation region has a nucleotide sequence that corresponds with nucleotide 12054651 to nucleotide 12054085 of the IFN-λ1 gene with the GenBank Accession No. NT_011109. This minimal region on the IFN-λ1 promoter is required for viral response.

Example 9

Identification of A Novel Repressor Region on the IFN-λ1 Promoter (Between ~1.2 kb to ~1.6 kb Upstream)

So far, we have identified a novel activation region (although the exact location differs from that reported by Onoguchi) present between ~0.6 kb and ~1.2 kb region of the IFN-λ1 promoter. To the best of the present inventor's knowledge, there has been no report regarding if a repressor region exists on the IFN-λ1 promoter, let alone its exact location.

To this end, the present inventors have surprisingly discovered a repressor region present within the ~1.2 kb to ~1.6 kb of the IFN-λ1 promoter. The repressor region has a nucleotide sequence that corresponds with nucleotide 12054025 to nucleotide 12053759 of the IFN-λ1 gene with the GenBank Accession No. NT_011109.

The observed high luciferase activity of the ~1.2 kb IFN-λ1 promoter construct was abrogated when the ~1.6 kb IFN-λ1 promoter construct was used (FIG. 8). The high ~1.2 kb IFN-λ1 promoter construct (2,700 relative light units) was reduced to 400 relative light units for the ~1.6 kb IFN-λ1 promoter construct when both were challenged by poly I:C. The data indicate (for the first time) the presence of a repressor region present between ~1.6 kb and ~1.2 kb upstream of the IFN-λ1 translation start site (i.e., ATG). The repressor region appears to exercise a higher hierarchy over the activation region on the IFN-λ1 promoter, when it comes to transcriptional control of the IFN-λ1 gene.

Example 10

The ~4 kb IFN-λ1 Promoter Contains Multiple Putative Transcriptional Sites

Figure 9:
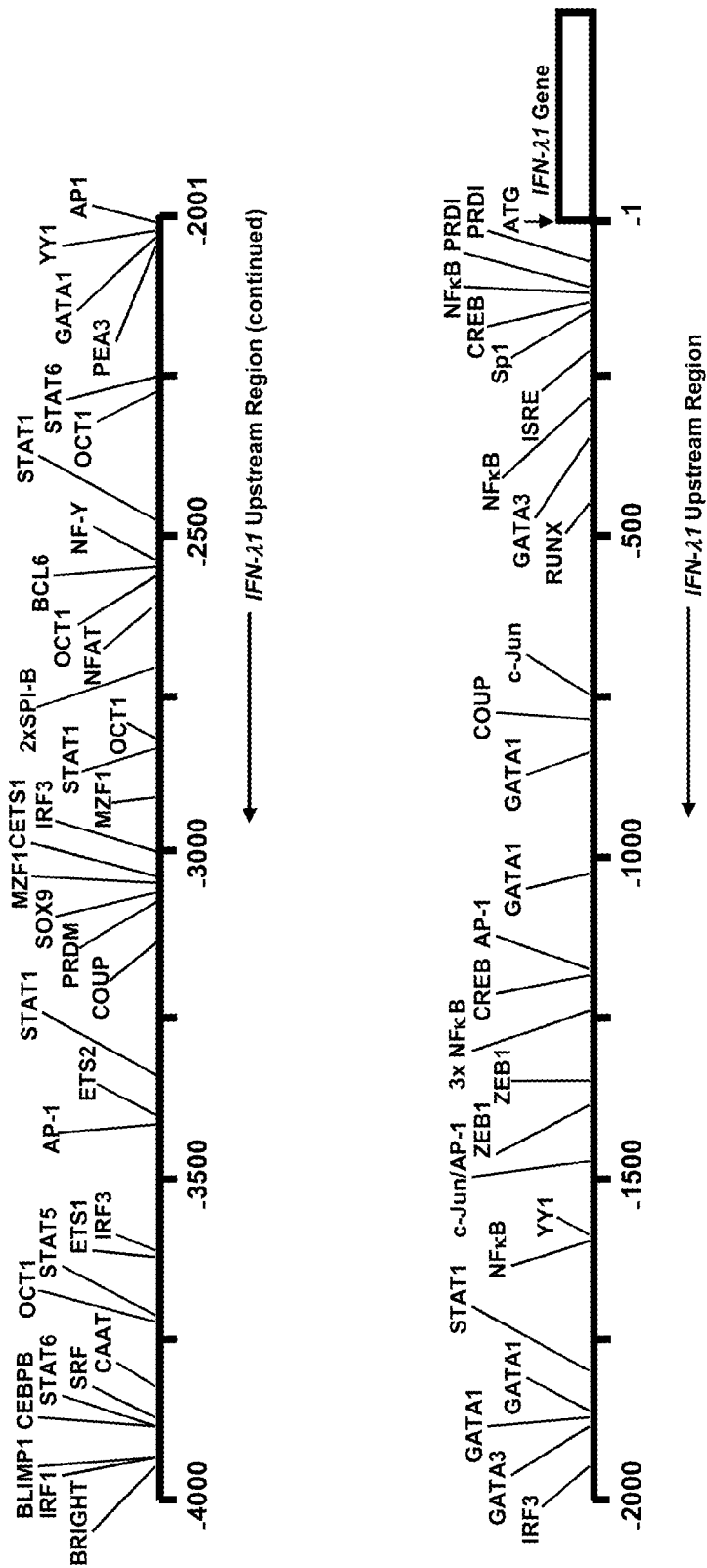
FIG. 9 depicts a schematic representation of putative transcription sites spanning the entire ~4 kb IFN-λ1 promoter from the translation start site (i.e., ATG). The putative transcription sites do not represent an exhaustive list and the transcription sites were identified using a bioinformatics program.

The IFN-λ1 promoter is speculated to be regulated through binding of transcription factors to the transcriptional sites present on the novel activation and repressor regions. We next sought to identify putative transcriptional sites present within the ~4 kb IFN-λ1 promoter. To do this, we performed a bioinformatics analysis of the ~4 kb IFN-λ1 promoter construct in order to identify putative transcriptional sites present in this fragment. We used two (2) bioinformatics programs: (i) "TESS" (http://www.cbil.upenn.edu/cgi-bin/tess/tess) and (ii) "Genomatix" (http://www.genomatix.de). Using the programs, we predicted >2,000 putative transcriptional sites. FIG. 9 depicts the complexity of the putative transcriptional sites present on ~4 kb IFN-λ1 promoter. Note that there are additional four (4) NF-κB sites and four (4) IRF sites predicted which Onoguchi or Osterlund did not report.

Example 11

Putative Transitional Sites within the Repressor Region on IFN-λ1 Promoter

Figure 10:
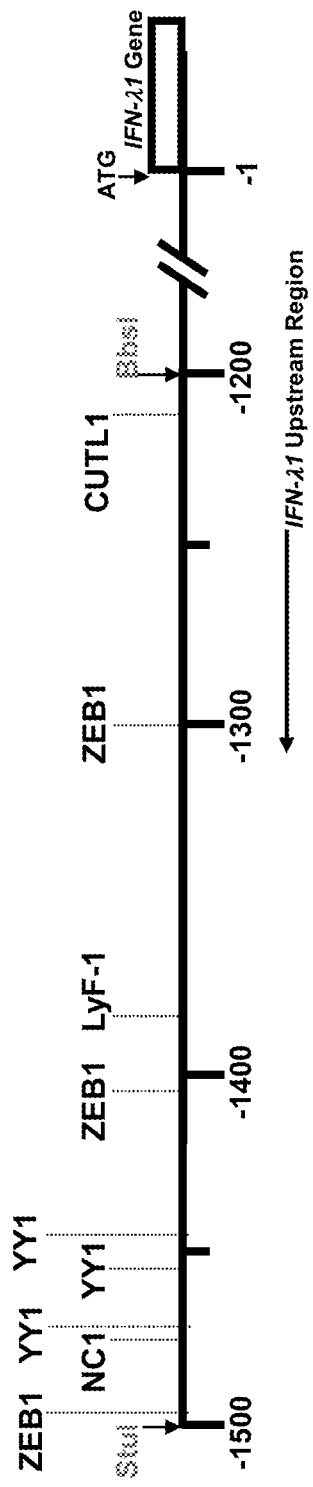
FIG. 10 depicts a schematic representation of the repressive promoter region of the IFN-λ1 gene. The repressive promoter region is located between 1.2 kb to 1.6 kb upstream of the IFN-λ1 gene from translation start site. The putative repressive transcription sites present within the repressive promoter region of the IFN-λ1 gene are indicated. The repressor region has a nucleotide sequence that corresponds with nucleotide 12054025 to nucleotide 12053759 of the IFN-λ1 gene with the Accession No. NT_011109.

We conducted a bioinformatics analysis to identify putative transcriptional sites within the repressor region on the IFN-λ1 promoter. We used the bioinformatics programs described supra and identified ~350 putative transcriptional sites. When the low-scoring sites (i.e., score <12.0) were eliminated, ~75 putative transcriptional sites remained in the analysis. Eight (8) of these sites were predicted to be bound by repressors that are present in mammals (FIG. 10).

The highest scoring repressor sites were those recognized by ZEB1 (aka AREB6, deltaEF1 and TCF8). ZEB1 is a zinc-finger transcription factor and is known to be functional in human epithelial cells (Vandewalle et al., 2009). FIG. 10 also depicts the ZEB1 site at −1,471 bp (having a score <12.0).

Example 12

ZEB1 Binds to the Repressor Region (~1.6 kb to ~1.2 kb) of IFN-λ1 Promoter in Resting Cells So far, we have identified three (3) putative binding sites for ZEB1 (a zinc-finger transcriptional factor) within the repressor region (~1.6 kb to ~1.2 kb) on the IFN-λ1 promoter. We sought to establish if ZEB1 binds to the repressor region during viral stimulation. We developed a cell system and determined the temporal change in IFN-λ1 mRNA expression using human airway epithelial cells. BEAS-2B cells were challenged with poly I:C (to mimic viral stimulation). IFN-λ1 mRNA expression was monitored using qPCR with specific primers (nucleotide sequences for the primers; see Methods). As shown in FIG. 11A, IFN-λ1 mRNA expression increased (from control values) between 90 and 315 minutes. The bell-shape curve for the temporal mRNA expression indicates an initial increase followed by a subsequent decrease in IFN-λ1 mRNA expression.

We performed a chromatin immunoprecipitation (ChIP) assay to determine if ZEB1 can bind to the two (2) specific ZEB1 binding sites within the repressor region (Site 1: 1,431 bp to 1,442 bp upstream of the IFN-λ1 translation start site; corresponding to nucleotide 12053857 to nucleotide 12053868 of the IFN-λ1 gene with the GenBank Accession No. NT_011109, Site 2: 1,319 bp to 1,332 bp upstream of the IFN-λ1 translation start site; corresponding to nucleotide 12053969 to nucleotide 12053982 of the IFN-λ1 gene with the GenBank Accession No. NT_011109) on the IFN-λ1 promoter. Chromatin from BEAS-2B cells following poly I:C challenge was isolated at 90, 135, 225, and 270 minutes post-challenge. Using a specific polyclonal antibody against ZEB1, we immunoprecipitated the ZEB1-chromatin complex. We amplified the immunoprecipitated ZEB1-chromatin complex using a pair of primer set (i.e., F1/R1; SEQ ID NOs: 28 and 29) (FIG. 11B) and the amount of immunoprecipitated chromatin is quantified using qPCR.

As shown in FIG. 11C, a significant ZEB1 binding occurred in resting cells (i.e., 0 min.). At 90 and 135 minutes, there was a decrease in ZEB1 binding. However, at 225 and 270 minutes post poly I:C challenge, ZEB1 binding increased (FIG. 11C). These data show that ZEB1 binds to the repressor region (through the two (2) ZEB1 binding sites) during viral stimulation.

Example 13

BLIMP-1 Binds (in a Delayed Fashion) to the IFN-λ1 Promoter (~4.0 kb to ~3.7 kb) after Viral Stimulation Previous study indicates a role for BLIMP-1 as a repressor in IFN-β (a member of type I class interferon). Although the ~1.2 kb to ~1.6 kb repressor region does not contain any BLIMP-1 transcriptional site, we sought to see if there may exist BLIMP-1 putative transcriptional sites outside of the repressor region of the IFN-λ1 promoter (but within the ~4 kb IFN-λ1 promoter).

Bioinformatics analysis has identified three (3) putative ISRE/PRDI or ISRE sites that the transcriptional factor BLIMP-1 can bind to. The first ISRE/PRDI site is located at 3,894 bp to 3,927 bp upstream of the IFN-λ1 translation start site, corresponds with nucleotide 12051354 to nucleotide 12051379 of the IFN-λ1 gene with the GenBank Accession No. NT_011109. The second ISRE site is located at 212 bp to 231 bp upstream of the IFN-λ1 translation start site, corresponding to nucleotide 12055050 to nucleotide 12055070 of the IFN-λ1 gene with the Accession No. NT_011109. The third ISRE/PDRI site is located at 81 bp to 101 bp upstream of the IFN-λ1 translation start site, corresponding to nucleotide 12055179 to nucleotide 12055198 of the IFN-λ1 gene with the GenBank Accession No. NT_011109 (see, FIG. 12A).

Figure 12A:
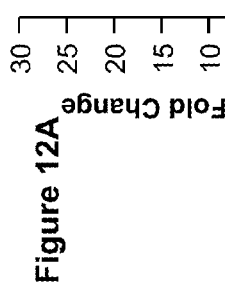
FIG. 12A depicts the time course of IFN-λ1 mRNA expression in naïve BEAS-2B cells following poly I:C challenge.
Figure 12B:
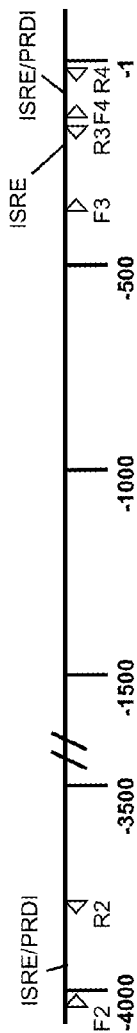
FIG. 12B depicts a schematic representation of three (3) forward and reverse primer sets: (i) F2 and R2 (SEQ ID NOs: 30 and 31) to amplify the ISRE/PDR1 region; (ii) F3 and R3 (SEQ ID NOs: 32 and 33) to amplify ISRE region; and (iii) F4 and R4 (SEQ ID NOs: 34 and 35) to amplify ISRE/PDR1' region. All these regions were examined for their ability to bind to BLIMP-1 in a ChIP assay.
Figure 12C:
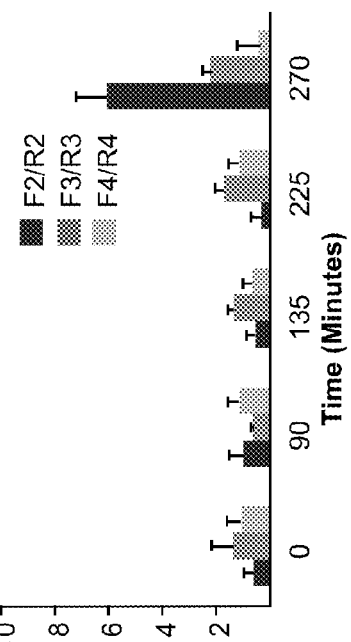
FIG. 12C depicts the immunoprecipitation of BLIMP-1 binding to the three (3) regions within the IFN-λ1 promoter (described in FIG. 12B). The IP fold-enrichment in F2 and R2 primer pair had the highest binding; that is, BLIMP-1 binds to most highly to the ISRE/PDR1 site on the IFN-λ1 promoter. The site has a nucleotide sequence that corresponds with nucleotide 12051354 to nucleotide 12051379 of the IFN-λ1 gene with the Accession No. NT_011109.

We performed ChIP assays for BLIMP-1's binding to the three (3) putative ISRE/PRDI or ISRE sites. We observed a significant binding of BLIMP-1 to the first ISRE/PRDI site that is ~3.8 kb upstream of the IFN-λ1 translation start site using the F2/R2 primer set (FIG. 12C). The time course of BLIMP-1 binding to this site was consistent with the timing of IFN-λ1 mRNA down-regulation (FIG. 12A). We observed only a modest BLIMP-1 binding to the third ISRE/PRDI site that is ~100 bp from the IFN-λ1 transcription start site that was visualized with the F4/R4 primer set (FIG. 12C). No BLIMP-1 binding was observed with the second IRSE site. These data show that BLIMP-1 can bind to IFN-λ1 gene (via two ISRE/PRDI sites) following viral stimulation, albeit with a delay time course.

Example 14

Optimization of siRNA Transfection

We have shown that ZEB1 and BLIMP-1 may be transcriptional repressors for IFN-λ1 gene. In this study, we utilized siRNA technology to target against these two (2) transcription factors (i.e., ZEB1 and BLIMP-1) in order to confirm their functional role in IFN-λ1 gene regulation.

In the initial experiments, we optimized siRNA transfection conditions by examining three (3) parameters; namely: (i) optimal transfectant cell density; (ii) types of culture media; (iii) types of transfection media (Table 2). The optimal conditions were determined by % transfection efficiency. Table 2 depicts the evaluation of optimal siRNA transfection conditions for BEAS-2B cells. The cells were transfected using different cell seeding densities, culture medium, and transfection medium. The transfection efficiency (%) was monitored 48 hours post-transfection using flow cytometry to detect a fluorescently labeled siRNA. For each optimization series, untransfected cells are included to show the background fluorescence.

We transfected BEAS-2B cells using Lipofectamine 2000 with a FITC-labeled siRNA (the siRNA is a control non-complementary oligonucleotide obtained from Dharmacon). The % transfection efficiency was determined using Flow Cytometry to detect the number of cells that were fluorescently labeled (Table 2). Out of the 12 conditions tested, we found the optimal transfection condition as followed: (i) optimal cell density of $0.2 \times 10^6$ cells/ml; (ii) LHC-9 culture medium; and (iii) Opti-MEM Lipofectamine 2000 as transfection medium. This transfection condition provides a consistent high % transfection efficiency (i.e., 85.1%), and a minimum background (2.98%) (Table 2).

TABLE 2

Conditions for siRNA Transfection

| Condition | Seeding Density (Cells/Well) | Culture Medium | Transfection Medium | Transfection Efficiency (%) |
|---|---|---|---|---|
| 1 | $0.2 \times 10^5$ | LHC-9 | Untransfected | 2.98 |
| 2 | $0.2 \times 10^5$ | LHC-9 | Opti-MEM | 85.1* |
| 3 | $0.2 \times 10^5$ | LHC-9 | RPMI-1640 | 74.6 |
| 4 | $0.2 \times 10^5$ | LHC-9 | LHC-9 | 75.2 |
| 5 | $0.2 \times 10^5$ | RPMI-1640, 10% FBS | Untransfected | 9.8 |
| 6 | $0.2 \times 10^5$ | RPMI-1640, 10% FBS | Opti-MEM | 86.2 |
| 7 | $0.2 \times 10^5$ | RPMI-1640, 10% FBS | RPMI-1640 | 78.9 |
| 8 | $0.2 \times 10^5$ | RPMI-1640, 10% FBS | LHC-9 | 81.8 |
| 9 | $0.4 \times 10^5$ | LHC-9 | Untransfected | 3.65 |
| 10 | $0.4 \times 10^5$ | LHC-9 | Opti-MEM | 78.3 |
| 11 | $0.4 \times 10^5$ | LHC-9 | RPMI-1640 | 72.2 |
| 12 | $0.4 \times 10^5$ | LHC-9 | LHC-9 | 83.3 |
| 13 | $0.4 \times 10^5$ | RPMI-1640, 10% FBS | Untransfected | 7.36 |
| 14 | $0.4 \times 10^5$ | RPMI-1640, 10% FBS | Opti-MEM | 75.1 |
| 15 | $0.4 \times 10^5$ | RPMI-1640, 10% FBS | RPMI-1640 | 63.4 |
| 16 | $0.4 \times 10^5$ | RPMI-1640, 10% FBS | LHC-9 | 74.1 |

*This represents the optimal condition that was used in subsequent siRNA transfection studies.

Example 15

Sequences of the BLIMP-1 and ZEB1 siRNA Oligonucleotides

Using the transfection procedure described above, BEAS-2B were transfected with a pool of four (4) oligonucleotides directed against either ZEB1 (GenBank accession numbers: NM_001128128 or NM_030751) or BLIMP-1 (GenBank Accession Numbers: NM_001198 or NM_182907) mRNA target sequence. ZEB1 protein is encoded by two (2) mRNA splice forms of the ZEB1 gene. The two (2) splice mRNA variants differ from each other at their N-termini. The GenBank Accession No. NM_030751 represents the shorter splice mRNA variant. This variant utilizes an alternative in-frame splice site. The GenBank Accession No. NM_001128128 represents the longer splice mRNA variant. This variant has an extended 5'UTR.

Similarly, the BLIMP-1 protein is encoded by two (2) mRNA splice forms. The BLIMP-1 mRNA with the GenBank Accession Number: NM_001198 is the longer splice form; whereas the BLIMP-1 mRNA with the GenBank Accession No. NM_182907 is the shorter splice form with a truncated N-terminus. The nucleotide sequences of the siRNA oligonucleotides (19 bp in length) that target the ZEB1 or BLIMP-1 mRNA splice forms are indicated in Table 3.

TABLE 3

Sequences of BLIMP-1 and ZEB1 siRNA Oligonucleotides

| SEQ ID NO. | siRNA Oligonucleotide Sequence | |
|---|---|---|
| | | Complementary Region on BLIMP-1 mRNA Accession No. NM_001198 |
| 8 | CCGAAUCAAUGAAGAAAUC | 2406-2424 |
| 9 | GAGAGUACAGCGUGAAAGA | 971-989 |
| 10 | GCAACUGGAUGCGCUAUGU | 701-719 |
| 11 | CCUCUACCGUUCUAACAUU | 1029-1047 |
| | | Complementary Region on ZEB1 mRNA Accession No. NM_030751 |
| 12 | CUGUAAGAGAGAAGCGGAA | 3018-3036 |
| 13 | CUGAAAUCCUCUCGAAUGA | 3071-3089 |
| 14 | GCGCAAUAACGUUACAAAU | 111-129 |
| 15 | GCAACAGGGAGAAUUAUUA | 2286-2304 |

Example 16 siRNA Efficiently Reduced BLIMP-1 and ZEB1 mRNA And Protein Levels

To first determine whether siRNA-mediated targeting of BLIMP-1 and ZEB1 mRNA could be achieved, BEAS-2B cells were transfected with pooled siRNA oligonucleotides that target BLIMP-1 or ZEB1 using the optimized transfection methodology. We examined the efficiency of the siRNA to mediate BLIMP-1 or ZEB1 degradation using both qPCR and Western blotting.

Figure 13B:
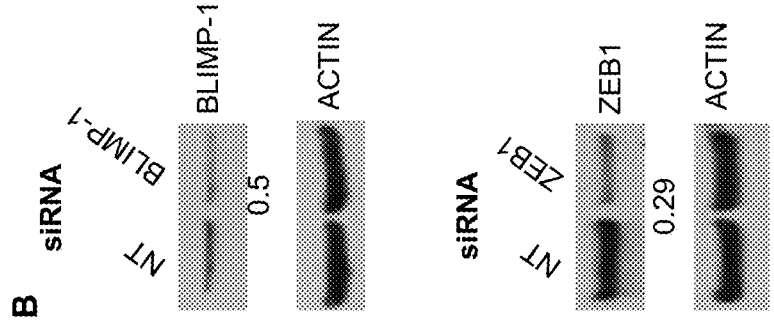
FIG. 13B depicts the Western blot analysis of the BEAS-2B cells transfected with siRNA against the BLIMP-1 and ZEB1 mRNA. siRNA treatment reduces both BLIMP-1 or ZEB1 proteins, without altering the actin level, indicating specificity.
Figure 13A:
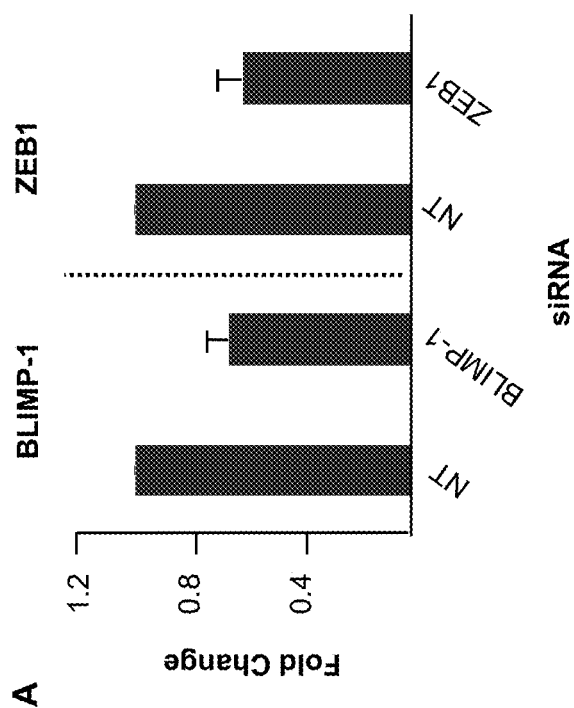
FIG. 13A depicts the BLIMP-1 and ZEB1 mRNA levels using qPCR in BEAS-2B cells. siRNA were transfected into the BEAS-2B cells. siRNA (SEQ ID NOs: 8, 9, 10, and 11) was used to target against the BLIMP-1 mRNA, and siRNA (SEQ ID NOs: 12, 13, 14, and 15) was used to target against the ZEB1 mRNA. The siRNA-transfected cells showed a decrease in the mRNA levels of BLIMP-1 and ZEB1.

As detected by qPCR, the BLIMP-1 siRNA pool led to a ~30% reduction of BLIMP-1 mRNA; and the ZEB1 siRNA pool led to a ~40% reduction in ZEB1 mRNA (FIG. 13A). Western blotting showed that this corresponded to a ~50% reduction in BLIMP-1 protein and a ~71% reduction in ZEB1 protein compared to non-targeting control siRNA (NT) (FIG. 13B). The reduction of BLIMP-1 and ZEB1 protein was still apparent at 64 hours post-transfection, indicating the stability of the siRNA in our experiments (FIG. 13B).

Figures 14A, 14B:
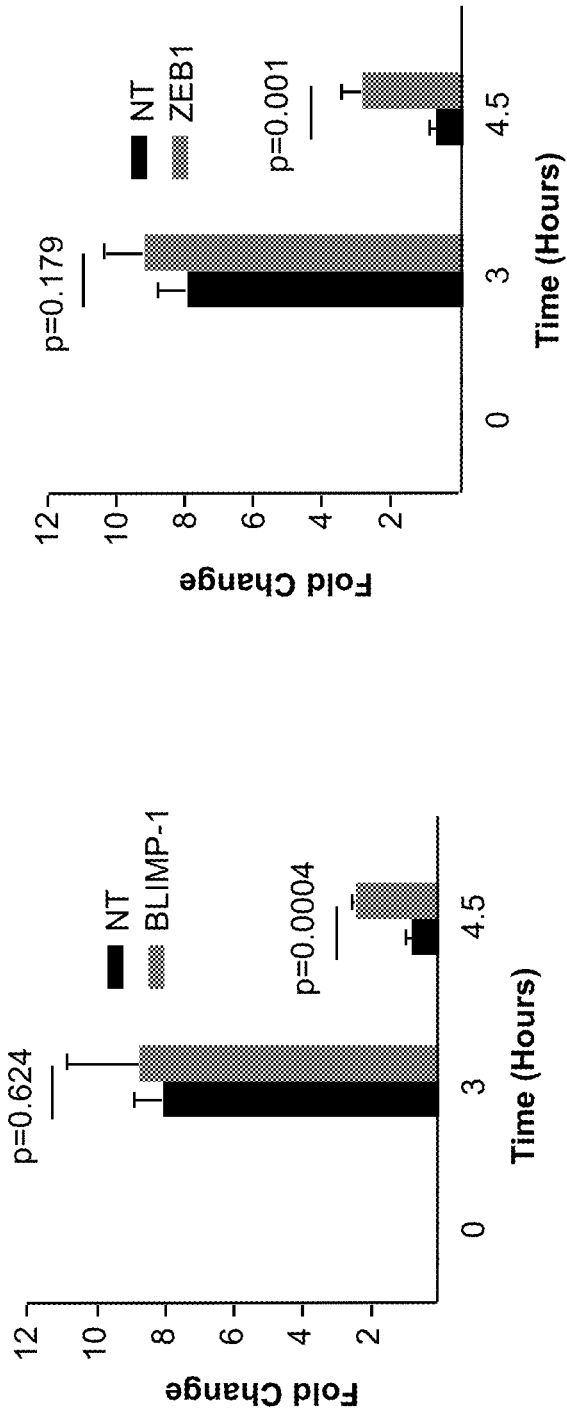
FIG. 14A depicts the effects of BLIMP-1 siRNA on IFN-λ1 mRNA expression. BEAS-2B cells were first transfected with BLIMP-1 siRNA (SEQ ID NOs: 8, 9, 10, 11). Transfectant cells were challenged with poly I:C for three hours. qPCR was then performed to monitor the mRNA expression of the IFN-λ1 gene. At 4.5 hours, BLIMP-1 siRNA treatment increases IFN-λ1 mRNA expression.
FIG. 14B depicts the effects of ZEB1 siRNA (SEQ ID NOs: 12, 13, 14, and 15) on IFN-λ1 mRNA expression. At 4.5 hours, ZEB1 siRNA treatment increases IFN-λ1 mRNA expression. Altogether, these data indicate that both BLIMP-1 and ZEB1 act as repressors for the IFN-λ1 gene. Statistical analysis was performed using a Student's T-test; the p-values are indicated.

Example 17 siRNA-Targeted Reduction of BLIMP-1 or ZEB1 Leads to an Increase in IFN-λ1 mRNA Expression In order to determine if targeted degradation of BLIMP-1 or ZEB1 by siRNA could lead to an increase in IFN-λ1, we examined the effect of BLIMP-1 or ZEB1 siRNA on IFN-λ1 mRNA expression by qPCR. In BEAS-2B cells transfected with BLIMP-1 siRNA, the IFN-λ1 mRNA was 3-fold higher than that of cells transfected with NT control (p=0.0004) (FIG. 14A). Similarly, treatment with ZEB1 siRNA led to a 3.7-fold (p=0.001) elevation in IFN-λ1 mRNA (FIG. 14B). These data indicate that siRNA-targeted reduction of BLIMP-1 or ZEB1 increase IFN-λ1 mRNA expression.

Figure 15:
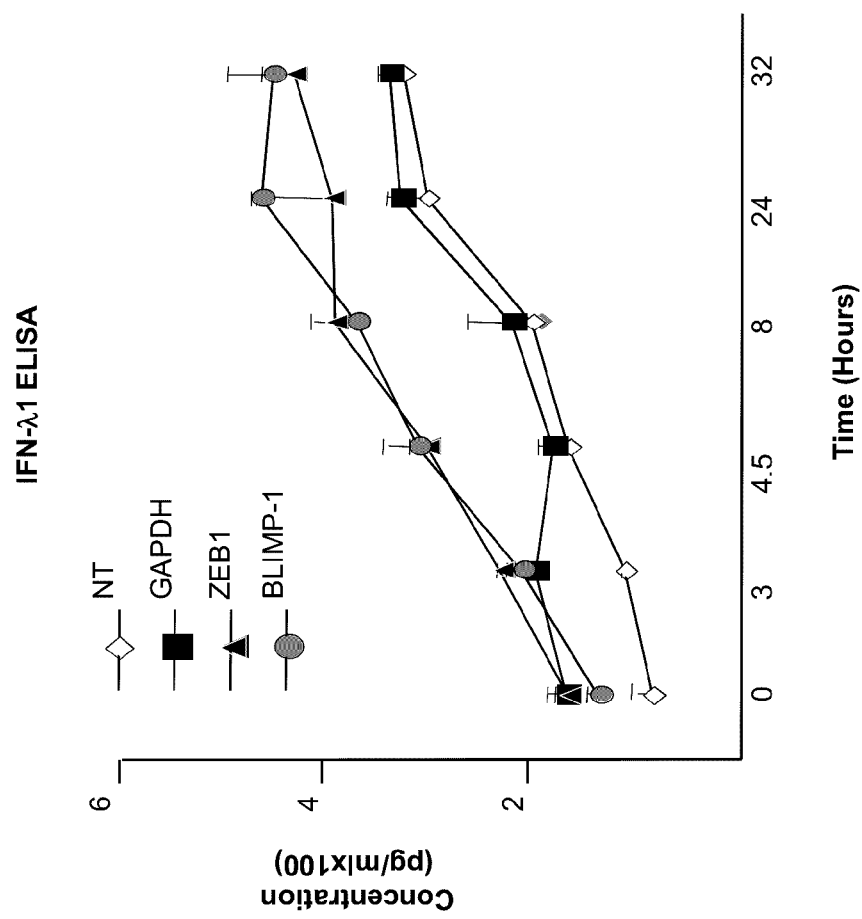
FIG. 15 depicts an ELISA experiment showing the IFN-λ1 concentration from siRNA-transfected BEAS-2B cells. BEAS-2B cell supernatants were obtained from the siRNA-transfected cells that were challenged with poly I:C for varying time periods. Note that the IFN-λ1 concentration increased in the siRNA (ZEB1 and BLIMP-1) groups as compared to that of control (NT and GAPDH) groups from 4.5 hours to 32 hours.

Example 18 siRNA-Targeted Reduction of BLIMP-1 or ZEB1 Leads to an Increase in IFN-λ1 Protein Because one of our goals is to therapeutically elevate IFN-λ through the use of siRNA, we determined if BLIMP-1 or ZEB1 siRNA resulted in increased IFN-λ1 protein levels. In this study, BEAS-2B cells were transfected with siRNA targeted against ZEB1 or BLIMP-1 and challenged with poly I:C (to mimic viral infection) for up to 32 hours. We performed ELISA for IFN-λ1 in supernatants from the siRNA-transfected cells. These experiments showed that IFN-λ1 protein was secreted more rapidly and to a greater extent in cells treated with siRNA for BLIMP-1 or ZEB1 as compared to both the NT and GAPDH siRNA controls (FIG. 15). Collectively, these data suggest that BLIMP-1 or ZEB1 siRNA could provide a means to therapeutically elevate IFN-λ1 in response to viral infection.

Example 19 siRNA-Targeted Reduction of BLIMP-1 or ZEB1 Leads to an Increase in Expression of Other Anti-Viral Response Genes A major function of IFN-λ1 is to promote the anti-viral response. We examined whether the BLIMP-1 or ZEB1 siRNA-induced increase of IFN-λ1 could lead to an increase in expression of anti-viral response genes. To this end, we transfected BEAS-2B cells with siRNA targeted against BLIMP-1 or ZEB1 and then challenged the cells with poly I:C. We examined the mRNA levels of the anti-viral genes "Myxovirus resistance 1" (Mx1) and "2'-5'-oligoadenylate synthetase 1" (Oas1) by qPCR.

Our data show that the Mx1 and OAS1 mRNA expression was increased in ZEB1 siRNA transfected cells at 24 and 32 hours of poly I:C stimulation (FIGS. 16A and B). The effect of ZEB1 siRNA was more pronounced and longer lasting than that of BLIMP-1 siRNA. This study indicates that the elevated IFN-λ1 secretion permitted by siRNA treatment increases the anti-viral responsiveness of airway epithelial cells.

Example 20

ZEB1 siRNA Specifically Regulate IFN-λ1 and IFN-λ3 Genes

In this series of experiments, we evaluated the specificity of BLIMP-1 or ZEB1 siRNA within the type-III IFN family (IFN-λ1, IFN-λ2 and IFN-λ3). We performed qPCR to evaluate the potential effect of the siRNA on IFN-λ1, IFN-λ2 and IFN-λ3.

Figures 17A, 17B:
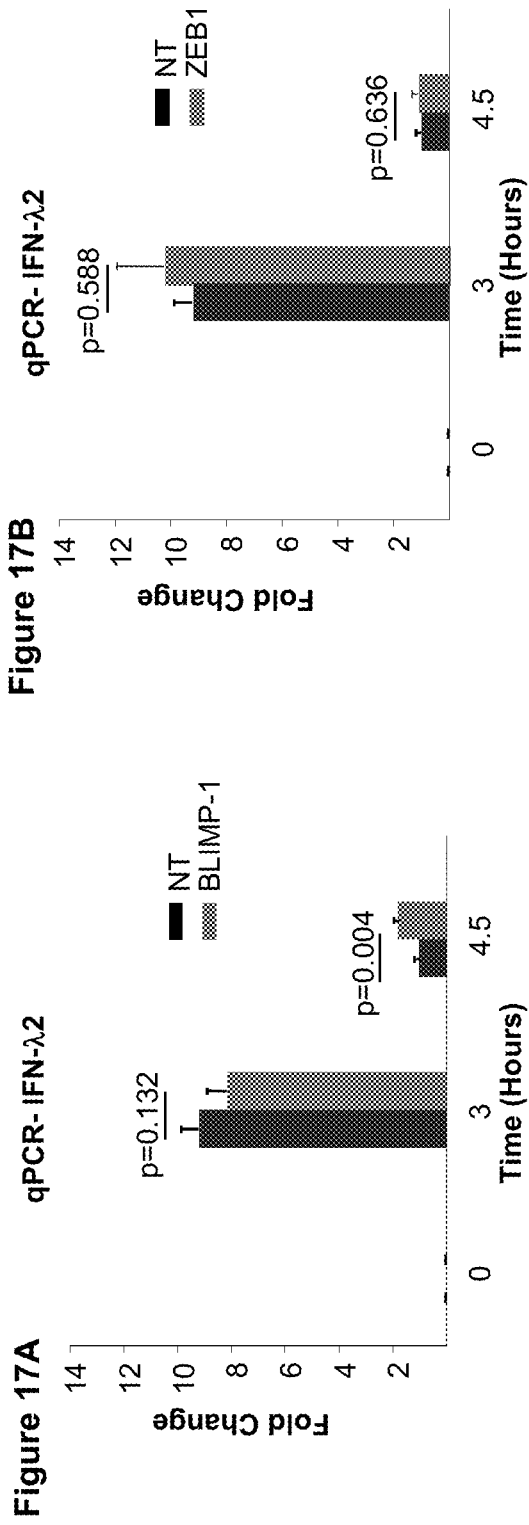
FIG. 17A depicts the specificity of BLIMP-1 siRNA on IFN-λ2. BEAS-2B cells were transfected with BLIMP-1 siRNA followed by poly I:C challenge. IFN-λ2 mRNA expression was monitored by qPCR. siRNA against BLIMP-1 modestly increased (statistically significant at p=0.004, Student's t-test) the mRNA expression of IFN-λ2.
FIG. 17B depicts the lack of ZEB1 siRNA's effect on IFN-λ2 levels.
Figures 18A, 18B:
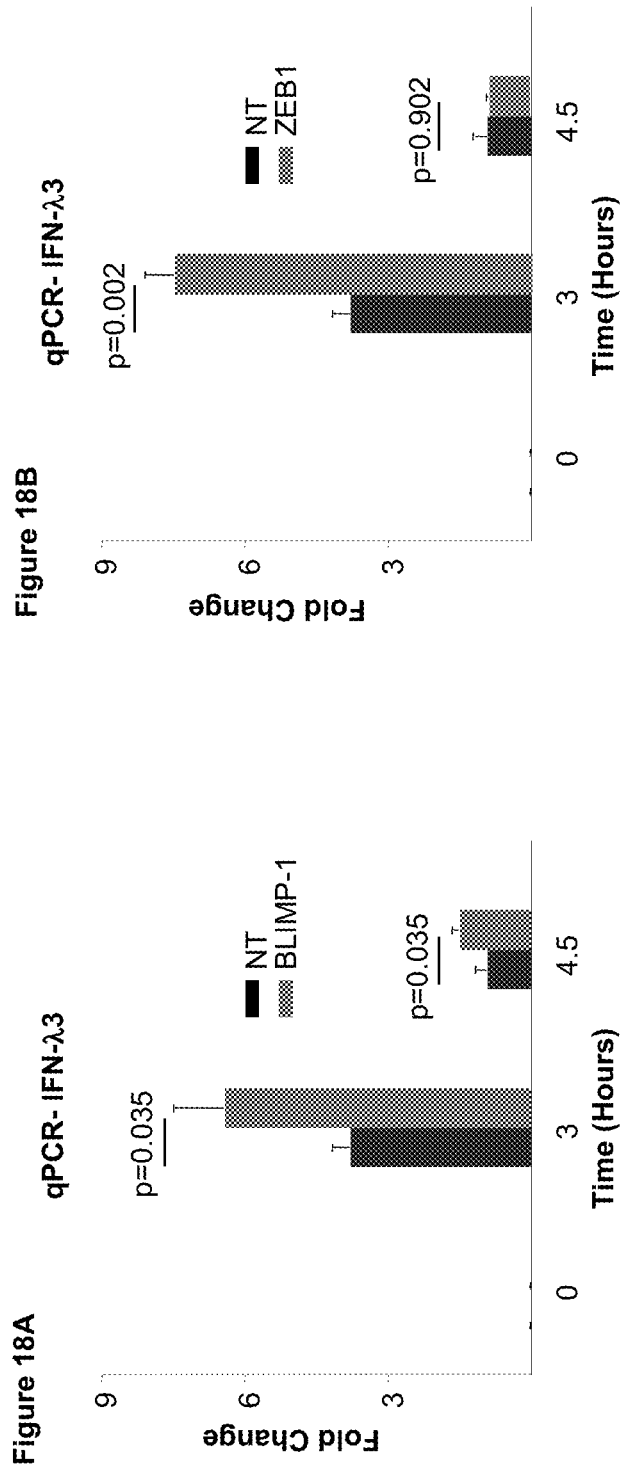
FIG. 18A depicts the specificity of BLIMP-1 siRNA on IFN-λ3. BEAS-2B cells were transfected with BLIMP-1 siRNA followed by poly I:C challenge. IFN-λ3 mRNA expression was monitored by qPCR. siRNA against BLIMP-1 increased the IFN-λ3 mRNA expression.
FIG. 18B depicts the ZEB1 siRNA's effect on IFN-λ3. siRNA against ZEB1 increased the IFN-λ3 mRNA expression.
Figure 19:
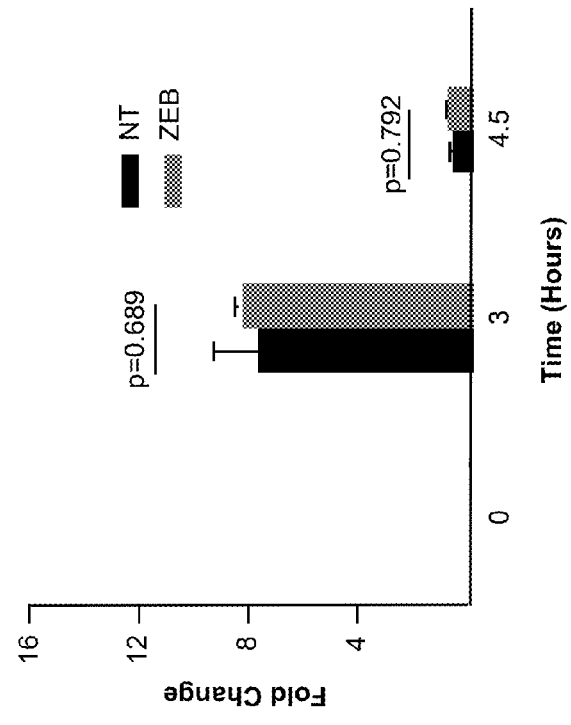
FIG. 19A depicts the specificity of BLIMP-1 siRNA on IFN-β1. siRNA against BLIMP-1 increased the IFN-β1 mRNA expression.
FIG. 19B depicts the lack of ZEB1 siRNA's effect on IFN-β1.
Figure 19:
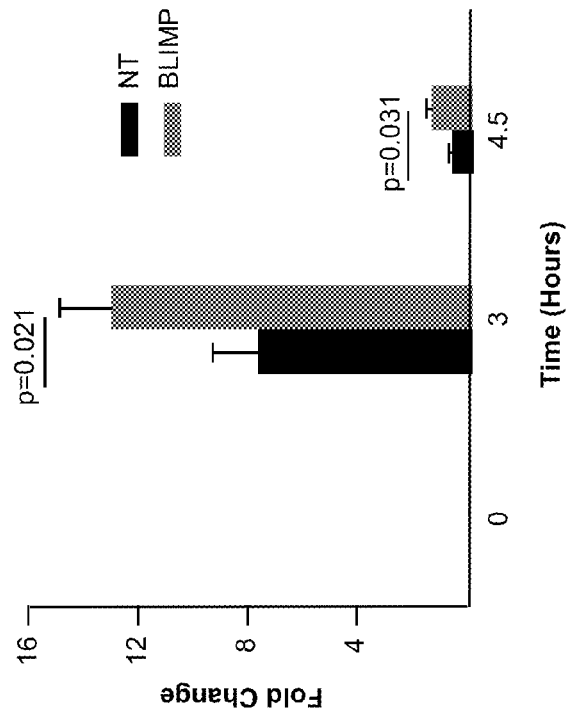

IFN-λ2 was affected marginally by BLIMP-1 siRNA (FIG. 17A) and was not affected by ZEB1 siRNA (FIG. 17B). For IFN-λ3, the effect of BLIMP-1 was more pronounced (FIG. 18A) and the regulation by ZEB1 was apparent (FIG. 18B). Surprisingly, these experiments suggest that ZEB1 is a specific regulator of IFN-λ1 and IFN-λ3, but does not regulate IFN-λ2. These experiments indicate that ZEB1 siRNA is a method to specifically elevate IFN-λ1 and IFN-λ3 levels.

Example 21

ZEB1 siRNA is Specific to the Type-III IFN Gene Family

Figure 20:
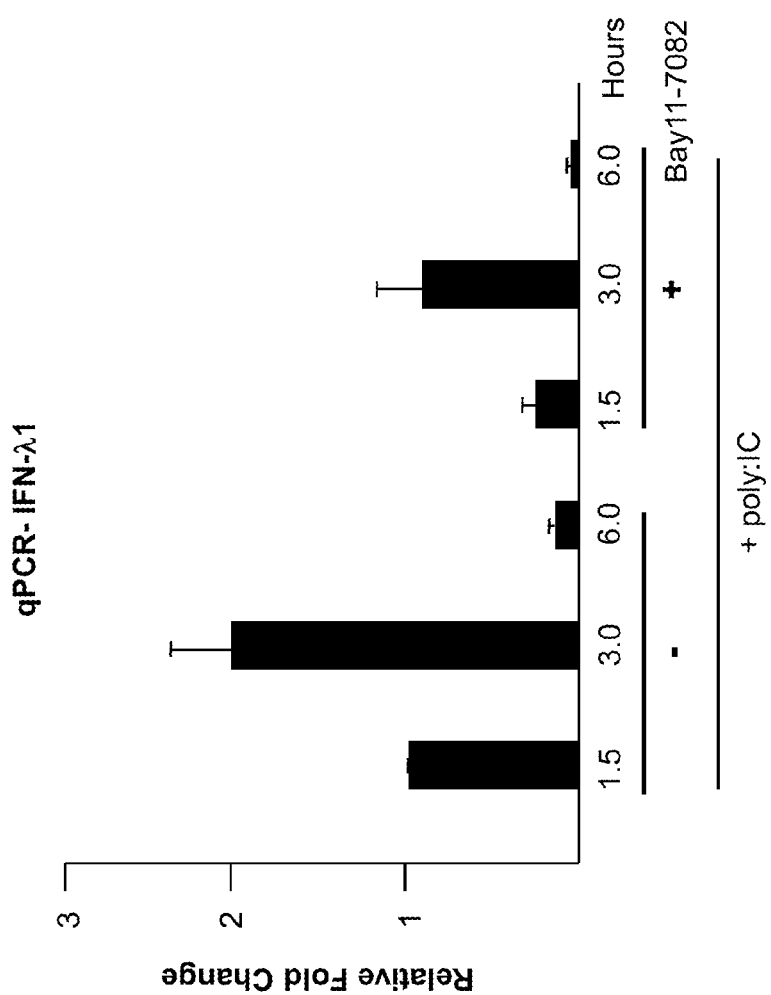
FIG. 20 depicts the role of NF-κB in virally-induced IFN-λ1 gene expression. BEAS-2B cells were challenged with poly I:C (to mimic viral infection) for various times. A NF-κB inhibitor (Bay11-7082) was added prior to measurement of IFN-λ1 mRNA levels by qPCR. Note that Bay11-7082 inhibited the virally-induced IFN-λ1 gene expression.

We evaluated the specificity of BLIMP-1 or ZEB1 to affect other interferon pathways. For these experiments, we utilized qPCR to detect levels of IFN-β, a type-I IFN family member. BLIMP-1 siRNA permitted a 2-fold increase in IFN-β1 mRNA levels at 3 and 4.5 hours of poly I:C treatment (FIG. 20). Importantly, IFN-β1 mRNA levels were not altered by the introduction of ZEB1 siRNA, indicating that this transcription factor acts specifically on type-III IFNs.

Example 22

Effect of NF-κB Inhibition on IFN-λ1 mRNA Expression

We have identified important regulatory regions of the IFN-λ1 gene using reporter constructs. We next wanted to determine if the IFN-λ1 reporter constructs would also be useful in identifying compounds that affect the activity of these regulatory regions. NF-κB was selected as a candidate to demonstrate this approach. The regulation of IFN-λ1 by NF-κB in airway epithelial cells has not been documented. In order to characterize IFN-λ1 regulation by NF-κB, the NF-κB inhibitor, Bay11-7082, which blocks IκB degradation, was utilized (FIG. 20). The ability of IFN-λ1 to be induced by poly I:C was reduced in the presence of the inhibitor documenting that NF-κB is required for IFN-λ1 expression (FIG. 20).

Example 23

Figure 21A:
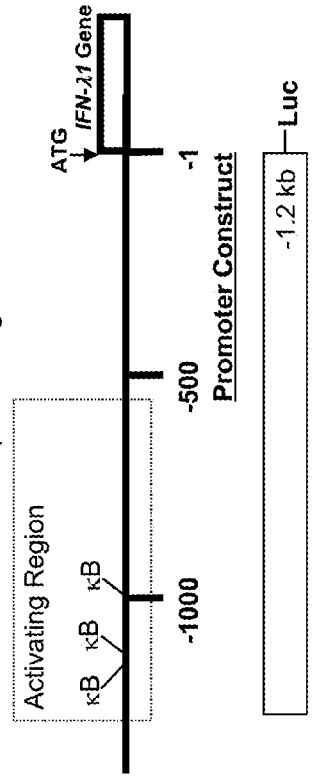
FIG. 21A depicts a schematic representation of the 1.2 kb IFN-λ1 reporter construct (i.e., pGL4.10-IFN-λ1-1.2 kb luciferase reporter) (See, FIG. 4). Note that there are three (3) putative NF-κB transcriptional sites (κB) near the −1,000 kb region of the ~1.2 kb IFN-λ1 reporter construct.
Figure 21B:
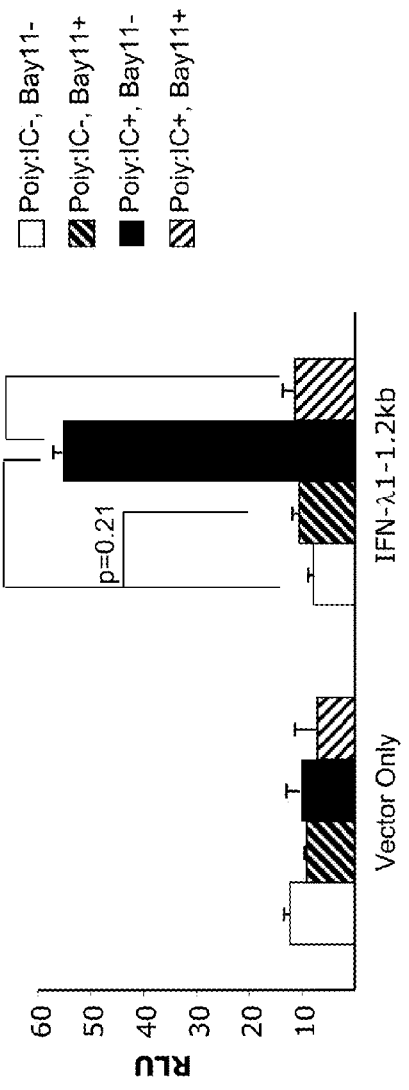
FIG. 21B depicts the role of NF-κB in the virally-induced IFN-λ1 gene activation. BEAS-2B cells were transfected with the ~1.2 kb IFN-λ1 reporter construct and viral stimulation was mimicked by poly I:C challenge. A NF-κB inhibitor (Bay11-

NF-κB Inhibition Reduces the Response of the 1.2 kb IFN-λ1 Reporter Construct to Viral Stimulation In order to document that the IFN-λ1 promoter constructs can be utilized as a screening tool to identify compounds effecting endogenous IFN-λ1 levels, Bay11-7082 was applied to the reporter system. BEAS-2B cells were transfected with the 1.2 kb IFN-λ1 reporter construct and challenged with poly I:C in the presence of the NF-κB inhibitor, Bay11-7082. The activation of the reporter by poly I:C challenge was reduced by Bay11-7082. This experiment showed that the reporter constructs in transfected cells (FIG. 21) are inhibited similarly to the IFN-λ1 gene in naïve cells (FIG. 20), indicating that the IFN-λ1 promoter constructs can be utilized as a screening tool.

Example 24

NF-κB Regulates IFN-λ1 mRNA Expression Through Binding of the IFN-λ1 Promoter Upon Viral Stimulation We next performed chromatin immunoprecipitation (ChIP) assays to examine if NF-κB family members can bind within the IFN-λ1 promoter activation region. For these assays we examined the binding of two NF-κB family members, p65 and c-REL to the IFN-λ1 promoter at the κB (using the F5/R5 primer set) and κB' (using the F6/R6 primer set) (FIG. 22B). To perform the ChIP assay, chromatin was isolated from BEAS-2B cells that had been treated with poly I:C for 90, 135, 225, and 270 minutes. These experiments indicated a significant p65 binding at 90 and 135 minutes of poly I:C challenge to the κB region (F5/R5 primer set) (FIG. 22C). C-REL bound the κB and κB' region at 90 minutes of poly I:C challenge (FIG. 22D). The occupancy of IFN-λ 1 promoter by NF-κB family members corresponds to the time points at which the IFN-λ1 mRNA expression is substantially increased (FIG. 22A). The findings from the luciferase and ChIP assays are indicative of NF-κB family members functioning to activate IFN-λ1 gene transcription.

Example 25

IFN-11 is Inducible by Poly I:C in Human Colon Epithelial Cells

Previous studies have shown that the type III IFNs are inducible by viral signaling through TLR3 [5, 11, 12, 17]. Since the intact IFN-λ1 gene is found in humans and not mice [22], our focus is on this member of the type III IFN family in the colon, although IFN-λ2 and 3 were found to also be induced similarly to IFN-λ1 (data not shown). To ensure that we could properly induce IFN-λ1 in a model forexpression in colon epithelia we utilized the SW480 and HT-29 cell lines stimulated with poly I:C. SW480 and HT-29 cells showed strong IFN-λ1 induction responses to poly I:C (FIGS. 23A and 23 B). The extent to which IFN-λ1 was induced in both cell lines was similar but induction kinetics varied between the cell lines (SW480, peak 6 hrs; HT-29, peak 4.5 hrs). This initial description of IFN-λ1 expression in colon epithelial cells confirms that despite some minor cell-line-specific differences in expression, IFN-λ1 is inducible by poly I:C in human colon epithelia cell lines.

Example 26

Activating and Repressive Roles of NF-κB Family Members

In these studies, we specifically examine the potential role of NF-κB in colon epithelial cells. It is known that NF-κB family members may activate or repress immune and inflammatory genes. Several different NF-κB dimers binding to putative binding sites within the IFN-λ1 promoter has been suggested, including our study using airway cells (see above). To that end, we utilized an siRNA knock-down approach here and discovered that NF-κB subunits (i.e., p50 and p65) can regulate the IFN-λ1 in response to poly I:C.

Specifically, we found that NF-κB p50 has a repressive function and NF-κB p65 has an activator function on IFN-λ1 gene expression in the NF-κB colon epithelial cells. NF-κB p50 knock-down (using siRNA against NF-κB p50) in colon epithelial cells resulted in a sustained induction of IFN-λ1 mRNA (See, FIG. 33B). The induction is illustrated by significant increases of IFN-λ1 mRNA at 3 and 8 hours of 2.3-fold (p=0.03) and 3.8 fold (p=$4\times10^{-4}$), respectively. The increase at 24 hours was not statistically significant (p=0.056).

NF-κB p65 knock-down (using siRNA against NF-κB p65) resulted in a sustained loss of IFN-λ1 gene expression at times of induction as compared to the control, NT group (See, FIGS. 34A and 34B). In colon epithelial cells, mRNA levels were significantly decreased at 3 hours (7.2-fold, p=0.03), 6 hours (17.9-fold, p=$2.0\times10^{-3}$) and 8 hours (8.6-fold, p=0.02) (See, FIG. 34B).

RelB, known to bind IFN-λ1 promoter elements in virally infected HEK293 cells, did not regulate IFN-λ1 in the colon epithelial cells, as its knock-down did not significantly alter expression levels relative to control (FIG. 35).

With respect to the IFN-λ1 protein, NF-κB p50 knock-down resulted in significant increases in secreted IFN-λ1 protein, both in airway and colon epithelial cells (See, FIGS. 36A and 36B) at the 24 and 32 hour time points. NF-κB p65 knock-down resulted in significant decreases in IFN-λ1 protein, both at the 24 and 32 hour time points (See, FIGS. 36A and 36B).

TABLE 4

Sequences of NF-κB1 p50, p65 and RELB siRNA Oligonucleotides

| SEQ ID NO. | siRNA Oligonucleotide Sequence |  |
|---|---|---|
|  | Complementary Region on NF-κB p50 mRNA Accession No. NM_003998 | |
| 40 | GGAGACAUCCUUCCGCAAA | 3254-3272 |
| 41 | GAUGGGAUCUGCACUGUAA | 828-846 |
| 42 | GAAAUUAGGUCUGGGGAUA | 2981-2999 |
| 43 | GCAGGAAGGACCUCUAGAA | 3347-3365 |
|  | Complementary Region on NF-κB p65 (RelA) mRNA Accession No. NM_021975 | |
| 44 | GGAUUGAGGAGAAACGUAA | 1030-1048 |
| 45 | CCCACGAGCUUGUAGGAAAA | 400-418 |
| 46 | GGCUAUAACUCGCCUAGUG | 1634-1652 |
| 47 | CCACACAACUGAGCCCAUG | 1598-1616 |
|  | Complementary Region on RELB mRNA Accession No. NM_006509 | |
| 48 | GCCCGUCUAUGACAAGAAA | 1001-1019 |
| 49 | CCAUUGAGCGGAAGAUUCA | 844-862 |
| 50 | GCACAGAUGAAUUGGAGAU | 280-298 |
| 51 | CUGCGGAUUUGCCGAAUUA | 1038-1056 |

Example 27

NF-κB p50 and p65 Knock-down Results in Altered ISG Expression

IFN-λ1 is known to induce the gene expression of the ISGs, Mx-1 and OAS1 through binding to IFN-λ1 receptor (i.e., IFN-λR, IL-28Rα/IL-10Rβ). It is generally known that the IFN-λ receptor is expressed in colon epithelial cells.

We hypothesize that the observed increase in IFN-λ1 protein expression (as a result of siRNA against NF-κB p50) may also increases the expression of anti-viral proteins. To that end, we monitored one of the viral genes (i.e., OAS1 mRNA) (to reflect an anti-viral response gene) following siRNA against NF-κB.

Knock-down of NF-κB p50 increases the OAS1 mRNA expression level, and knock-down of NF-κB p65 decreases the OAS1 mRNA expression level (FIG. 37). We observed that NF-κB p50 knock-down increased 2-fold of the OAS1 mRNA level at 8 hours (p=0.04) and a 4.5-fold increase of the OAS1 mRNA level at 32 hours (p=3.8×10$^{-3}$). In contrast, NF-κB p65 knock-down decreased 2.7-fold of the OAS1 mRNA level at 24 hours (p=0.005) and a 3.3-fold decrease of the OAS1 mRNA level at 32 hours (p=2.0× 10$^{-3}$). (See, FIG. 37).

Example 28

Repressors ZEB1 and BLIMP-1 Differentially Regulate IFN-λ1

We have shown (Examples above), in airway epithelial cells, that IFN-λ1 upregulation can be achieved through ZEB1 and BLIMP-1 transcription factors in response to viral infection. In this study, we examined if ZEB1 and BLIMP-1 may similarly upregulate the IFN-λ1 gene in colon epithelial cells.

We used a colon epithelial cell line (i.e., SW480 cells) and treated these cells with siRNA targeting ZEB. We examined if siRNA treatment leads to an increase in IFN-λ1 mRNA expression in response to poly I:C challenge (to mimic viral infection). Under the condition of poly I:C challenge, siRNA against ZEB1 increased in IFN-λ1 mRNA by 3.1-fold after 6 hours (p=0.03) and 2.1-fold at 8 hours (p=0.03) (See, FIG. 25). Similarly, siRNA against BLIMP-1 increased 2.7-fold (p=0.01) and 3.3-fold (p=0.002) IFN-λ1 mRNA expression at 6 and 8 hours, respectively (FIG. 29).

We also examined if the protein expression of IFN-λ1 is affected by siRNA treatment in the colon epithelial cells. The IFN-λ1 protein levels (i.e., secreted IFN-λ1 in the cell supernatants) were monitored by ELISA. Under the condition of poly I:C challenge, siRNA against ZEB1 increased IFN-λ1 protein by ~3-fold after 32 hours (p=0.03) (See, FIG. 26). siRNA against BLIMP-1 did not alter the IFN-λ1 protein expression at either 24 or 32 hours. (FIG. 30).

This finding is surprising at two levels. First, while we observed siRNA against ZEB1 increased IFN-λ1 protein expression in colon cells, siRNA against BLIMP-1 had no effect. Second, while both siRNA against ZEB1 and BLIMP-1 increased IFN-λ1 mRNA expression, only siRNA against ZEB1 had the ability to upregulate IFN-λ1 protein expression.

Unexpectedly, we discovered that airway epithelial cells respond differently than colon epithelial cells when treated with siRNA against ZEB1 or BLIMP-1. While ZEB1 knock-down increased IFN-λ1 protein expression in both airway and colon epithelial cells, BLIMP-1 knock-down only increased IFN-λ1 protein expression in the airway epithelial cells.

This finding suggests the regulation of IFN-λ1 protein is complex and has cell-type specificity. The underlying mechanism remains unknown. The present observation represents the first report of a differential regulation of IFN-λ1 protein by ZEB1 and BLIMP-1 in these two cell types. As with NF-κB p50 knock-down, ZEB1 knock-down led to significantly increased OAS1 expression at 24 and 32 hours (p=0.04 and p=0.002); (FIG. 27). These data are consistent with our observation in airway epithelium (Example above). The data support a role of ZEB1 and BLIMP-1 as regulators of IFN-λ1 expression in colon epithelial cells.

Example 29

ZEB1 Knock-down Enhances IFN-λ1 Specific Viral Responses in Colon Epithelial Cells In this study, we examined the specific effects of ZEB1 knock-down on type III IFN (i.e., IFN-λ1) and type I IFN (i.e., IFN-β). We observed, in airway epithelial cells, that ZEB1 knock-down increased type III IFN (i.e., IFN-λ1), but not type I IFN (i.e., IFN-β) (See, above Examples). Here, we determined if ZEB1's specific effect on type III IFN (i.e., IFN-λ1) can similarly be found in colon epithelial cells.

Based on the evidence that ZEB1 did not regulate IFN-β in bronchial epithelial cells, we sought to determine if the same distinction was apparent in colon epithelia. BLIMP-1 is well characterized as a negative regulator of IFN-β and its knock-down resulted in a significant increase in IFN-β (FIG. 31). BLIMP-1 knock-down resulted in a 4.4-fold increase seen at 3 hours (p=0.01) and supports the role of BLIMP-1 as a negative regulator of IFN-β. ZEB1 knock-down resulted in no significant changes in IFN-β above the NT group (FIG. 31). Therefore, this evidence suggests that ZEB1 does not regulate IFN-β but does regulate IFN-λ1 in response to treatment with poly I:C in colon epithelial cells.

Conversely, NF-κB is not a type III IFN specific regulator. NF-κB is well known to be a component of the immune system, acting to activate IFN-β gene expression in response to virus. Our results show a similar result of NF-κB p50 knock-down on IFN-β to that seen on the type III IFNs (FIG. 38). The 2.5-fold increase seen at 3 hours 9 is significant (p=0.049. NF-κB p65 knock-down resulted in significant decreases at 3 and 8 hours (p=0.02 and 0.03) (FIG. 38); NF-κB p65 therefore appears to be an activator used by both IFN families.

Example 30

GATA1 Knock-Down Decreases IFN-λ1 Protein Expression, while EVI1 or CRX Knock-Down Increases IFN-λ1 Protein Expression In this study, we examined the effect of siRNA against GATA1, EVI1, CRX and GATA3 transcription factors (predicted based on bioinformatics (www.genomatix.de) that have binding sites within the 4 kb of the IFN-λ1 gene promoter—SEQ ID NO: 1) (See, FIG. 9). We monitored the IFN-λ1 protein expression by ELISA as described. Table 5 summarizes the specific siRNA nucleotide sequences used in this experiment.

TABLE 5

Sequences of GATA1, EVI1, CRX and GATA3 siRNA Oligonucleotides

| SEQ ID NO. | siRNA Oligonucleotide Sequence | |
|---|---|---|
| | Complementary Region on GATA1 mRNA Accession No. NM_002049 | |
| 52 | GGACAGGCCACUACCUAUG | 747-765 |
| 53 | ACGCAGAGGCCUACAGACA | 285-303 |
| 54 | GCUGGUGGCUUUAUGGUGG | 1082-1100 |
| 55 | CCAAGAAGCGCCUGAUUGU | 822-840 |
| | Complementary Region on EVI1 mRNA Accession No. NM_001105077 | |
| 56 | GAUAAAACGUCCAUGGUUA | 1124-1142 |
| 57 | GAACCAGUGACAAGUAAUU | 3077-3095 |

TABLE 5-continued

Sequences of GATA1, EVI1, CRX and GATA3 siRNA Oligonucleotides

| SEQ ID NO. | siRNA Oligonucleotide Sequence | |
|---|---|---|
| 58 | AAGAUGAGGUGUUGUUAGA | 280-298 |
| 59 | GAUAGAGACUUGAGAUCGU | 3015-3033 |
| | Complementary Region on CRX mRNA Accession No. NM_000554 | |
| 60 | GGAAGUUUCAGAUCUUGUA | 1085-1103 |
| 61 | GGUCUCCGAGCUCCUAUUU | 830-848 |
| 62 | GUGAGGAGGUGGCUCUGAA | 410-428 |
| 63 | CCAAGACCCUCCACAGAUG | 577-595 |
| | Complementary Region on GATA3 mRNA Accession No. NM_001002295 | |
| 64 | CAUCGACGGUCAAGGCAAC | 713-731 |
| 65 | GAAGGCAUCCAGACCAGAA | 1635-1653 |
| 66 | CCCAAGAACAGCUCGUUUA | 1716-1734 |
| 67 | GUACAGCUCCGGACUCUUC | 1241-1259 |

GATA1 is generally known to be a transcription factor that plays a role in erythroid cell development. Knock-down of GATA1 using a pool of four siRNA oligonucleotides consisting of SEQ ID NOs: 52, 53, 54, 55 led to a decrease in IFN-λ1 protein expression in airway epithelial cells. Table 6 summarizes the ELISA results in airway epithelial cells following siRNA treatment and poly I:C for 6, 24 and 32 hours.

EVI1 is generally known to play a role in oncogenesis. Knock-down of EVI1 using a pool of four siRNA oligonucleotides consisting of SEQ ID NOs: 56, 57, 58, and 59 led to an increase in IFN-λ1 protein expression in airway epithelial cells. Table 6 summarizes the ELISA result.

CRX is generally known to play a role in eye development and retinal function. Knock-down of CRX using a pool of four siRNA oligonucleotides consisting of SEQ ID NOs: 60, 61, 62, and 63 led to an increase in IFN-λ1 protein expression in airway epithelial cells. This increase in IFN-λ1 protein was transient at 6 hours (Table 6).

GATA3 is generally known to play a role in hematopoetic cell development and function. Knock-down of GATA3 using a pool of four siRNA oligonucleotides consisting of SEQ ID NOs: 64, 65, 66, and 67) had no effect on IFN-λ1 protein expression (Table 6).

TABLE 6

Summary of the Effects of siRNA Targeting GATA1, EVI1, CRX and GATA3 on IFN-λ1 Protein Levels

| Targeted Transcription Factor | Time (hr) | IFN-λ (pg/ml) Poly I:C NT | | % Relative to NT | p-Value |
|---|---|---|---|---|---|
| | | NT | Specific | | |
| GATA1 | 6 | 8.98 | 6.24 | 69 | 0.023 |
| | 24 | 10.96 | 5.25 | 48 | 0.011 |
| | 32 | 19.36 | 9.60 | 50 | 0.023 |

TABLE 6-continued

Summary of the Effects of siRNA Targeting GATA1,
EVI1, CRX and GATA3 on IFN-λ1 Protein Levels

| Targeted Transcription Factor | Time (hr) | IFN-λ (pg/ml) Poly I:C NT | | IFN-λ (pg/ml) Specific | % Relative to NT | p-Value |
|---|---|---|---|---|---|---|
| EVI1 | 6 | 8.98 | | 15.73 | 175 | 0.004 |
|  | 24 | 10.96 | | 15.80 | 144 | 0.008 |
|  | 32 | 19.36 | | 28.98 | 150 | 0.024 |
| CRX | 6 | 8.98 | | 17.06 | 190 | 0.0004 |
|  | 24 | 10.96 | | 24.37 | 222 | 0.073 |
|  | 32 | 19.36 | | 21.48 | 111 | 0.371 |
| GATA3 | 6 | 8.98 | | 10.22 | 114 | 0.203 |
|  | 24 | 10.96 | | 11.16 | 102 | 0.833 |
|  | 32 | 19.36 | | 14.74 | 76 | 0.207 |

Materials, Methods and Protocols
Cloning

The 5' upstream region ("promoter") fragments of the IFN-λ1 gene were obtained by PCR from genomic DNA of a normal donor individual using primers directed to amplify positions 12051212-12055279 on NT_011109.15|Hs19_11266 *Homo sapiens* chromosome 19 genomic contig, reference assembly. The primers to amplify the desired region of the IFN-λ1 gene were as follows:

```
Forward,
GCTACAGTATTGCCAGCATATAG;        (SEQ ID NO: 16)

Reverse,
GGCTAAATCGCAACTGCTTC.           (SEQ ID NO: 17)
```

The PCR product was then ligated into the pSC-A vector (Invitrogen, Carlsbad, Calif.) backbone using the "TA cloning" (Invitrogen, Carlsbad, Calif.), resulting in the "pSC-A-IFN-λ1-4 kb" plasmid. The IFN-λ1-4 kb insert was subcloned into the pGL4.10 vector backbone from the pSC-A-IFN-λ1-4 kb plasmid through digestion with KpnI (New England Biolabs, Ipswich, Mass.) and SacI (New England Biolabs, Ipswich, Mass.) restriction endonucleases to release the IFN-λ1-4 kb insert. This insert was then ligated to pGL4.10 (Promega, San Luis Obispo, Calif.) that had been digested with the KpnI and SacI restriction endonucleases. The resulting "pGL4-IFN-λ1-4 kb" plasmid was subsequently digested with various restriction endonucleases (New England Biolabs, Ipswich, Mass.) to remove portions of the IFN-λ1-4 kb promoter. The remaining vector backbone was then re-circularized using the Rapid DNA Ligation Kit (Roche, Nutley, N.J.). Restriction endonucleases were selected based on lack of overlap with predicted transcription factor binding sites as determined by Transfac (http://www.gene-regulation.com) and Genomatix (www.genomatix.de).

Colon Cell Culture and Viral Stimulation by Poly I:C in Colon Cells

The SW480 (CCL-228) and HT-29 (HTB-28) cell lines (both are human colon epithelial cells) were purchased from the American Tissue Culture Collection (ATCC; Rockville, Md.). Both cell lines were maintained following instructions under ATCC's recommendation. siRNA transfection and poly I:C stimulation in SW480 cells were carried out in a maintenance medium which was DMEM (Gibco, 11965-092) containing 4.5 gm/L D-glucose and 4 mM L-glutamine. siRNA transfection and poly I:C stimulation in HT-29 cells were carried out in a maintenance medium which was McCoy's 5A (Gibco, 16600-082) containing 4 mM L-glutamine. Both colon cell lines were grown to 80% confluence then passaged by trypsinization using TrypLE™ (Gibco, 12605). Cells were then seeded for experimentation from cultures that reached 70-80% confluence. In 24-well plates, cells were plated at a density of $2 \times 10^5$ cells/well and stimulated with 50 µg/mL poly I:C (Sigma-Aldrich, P0913). Cells were harvested over a time-course of 24 to 32 hours at the time points indicated.

Small Interfering RNA (siRNA) Knock-Down

Small interfering RNA (siRNA) targeting NF-κB1 (p50), RelA (p65), RelB, ZEB1, BLIMP-1, or non-targeting (NT; control) were purchased from Thermo Scientific (Lafayette Colo.). siRNA was transfected into SW480 cells using Lipofectamine RNAiMax (Invitrogen, 13778) according to manufacturer's instructions. Cell culture medium was replaced at 24 hours post-transfection and poly I:C stimulations were carried out as described above. Supernatants, protein from whole cell extracts and RNA were harvested at the indicated time points.

Western Blot Analysis

Cells were harvested 36 hours post-transfection by trypsinization with TrypLE™ (Gibco). Whole cell lysates and total protein from transfected cells were obtained by lysis utilizing ProteoJET™ (Fermentas, K0301), with 10 mM PMSF and protease inhibitor cocktail (Sigma-Aldrich) and were subjected to semi-dry immunoblotting. Antibodies specific for BLIMP-1 (Cell Signaling C14A4), ZEB1 (Santa Cruz, H-102), NF-κB p50 (Santa Cruz, NLS), NF-κB p65 (Santa Cruz, C-20), RelB (Santa Cruz, C-19), and β-actin (Sigma-Aldrich, AC-15) were utilized for primary detection. Protein-Ab signals were detected using horseradish-peroxidase (HRP) conjugated secondary antibodies, all purchased from Thermo Scientific (31462, 31439). Image analysis was performed utilizing Image J software (http://rsbweb.nih.gov/ij/) with β-actin serving as a loading control and normalizer.

qRT-PCR

Quantitative RT-PCR (qRT-PCR) was used to analyze the mRNA levels of genes of interest. RNA was reverse transcribed using the "AffinityScript QPCR cDNA Synthesis Kit" (Agilent Technologies, 600559) and subsequent PCRs were performed using "Brilliant®SYBR® Green QPCR Master Mix" (Agilent Technologies, 600828). Reactions were performed on and measured by Strategene 3000P or 3005P instruments and analyzed by the accompanying MxPro software (Agilent Technologies), using hypoxanthine phosphoribosyltransferase (HPRT) as the normalizer for all samples. The primer sequences were as follows:

```
                                        (SEQ ID NO: 18)
IFN-λ1-F-    5' CTTCCAAGCCCACCACAACT 3'

(SEQ ID NO: 19)
IFN-λ1-R-    5' GGCCTCCAGGACCTTCAGC 3'

(SEQ ID NO: 68)
IFN-β-F-     5' CAGCAATTTTCAGTGTCAGAAGC 3'

(SEQ ID NO: 69)
IFN-β-R-     5' TCATCCTGTCCTTGAGGCAGT 3'

(SEQ ID NO: 26)
ZEB1-F-      5' GCACCTGAAGAGGACCAGAG 3'

(SEQ ID NO: 27)
ZEB1-R-      5' GCCTCTATCACAATATGGACAGG 3'

(SEQ ID NO: 70)
OAS1-F-      5' AACTGCTTCCGACAATCAAC 3'
```

```
OAS1-R-     5' CCTCCTTCTCCCTCCAAAA 3'
                               (SEQ ID NO: 71)

(SEQ ID NO: 20)
HPRT-F-     5' CAGCCCTGGCGTCGTGATTAG 3'

(SEQ ID NO: 21)
HPRT-R-     5' GCAAGACGTTCAGTCCTGTCCATA 3'
```

For all qRT-PCR experiments, the data represent normalized fold-changes calculated using the efficiency-calibration method.

ELISA

The IFN-λ1 ELISA was performed using the Ready-Set-Go ELISA (E-Bioscience) kit, according to the manufacturer's protocol.

Statistical Analysis

Where indicated, a Student's two-tailed t-test was used for statistical analysis. A p-value of ≤0.05 was considered significant.

Cell Culture, Transfection and Stimulation

BEAS-2B cells were cultured in LHC-9 medium (Invitrogen, Carlsbad, Calif.). Cells were plated at $0.2 \times 10^6$ cells/ml on the day before transfection. Prior to transfection, the medium was changed to serum-free RPMi (Invitrogen). For transfection of plasmid DNA, 40 ng of DNA was mixed with Opti-MEM (Invitrogen) to a final volume of 5 µl and then mixed with 5 µl of Lipofectamine (Invitrogen), incubated for 30 minutes at room temperature and applied to the cells. The medium was changed to LHC-9 at 5 hours post-transfection. Plasmid DNA transfections were performed in 96-well plates. All stimulations on DNA transfected cells were initiated 24 hours post-transfection. For transfection of siRNA, "SmartPool" siRNAs targeting BLIMP-1, ZEB1, GAPDH or non-targeting (NT) were purchased from Sigma. 50 µM of siRNA was mixed with Optim-MEM to a final volume of 50 µl. 5 µl of Lipofectamine 2000 (Invitrogen) was mixed with 250 µl of Opti-MEM and incubated at room temperature for 10 minutes. The DNA and Lipofectamine 2000 were combined and then incubated for an additional 30 minutes at room temperature, 100 µl was then applied to the cells. siRNA transfections were performed in 24-well plates. "siGLO" (Dharmacon) to optimize the efficiency based on visualization of Fluorescein using flow cytometry. At 24 hours post-transfection, cells were reseeded at $0.2 \times 10^6$ cells/ml; poly I:C stimulation was initiated 36 hours post-transfection. Poly I:C (Sigma) stimulation was performed at a final concentration of 50 µg/ml. Supernatants, protein from whole cell extracts and total RNA were harvested following 0, 3, 4.5, 8, 24, and 32 hours of stimulation.

qPCR

RNA was prepared using the Trizol method (Invitrogen) and converted to cDNA using the AffinityScript Kit (Stratagene, La Jolla, Calif.). qPCR was performed in triplicate on diluted cDNA using the Brilliant II SYBR Kit (Stratagene, La Jolla, Calif.). The PCR was carried out using the MX3000 machine (Stratagene, La Jolla, Calif.). Relative fold changes were generated using the "ΔΔCT" equation. Standard deviations were calculated based on three replicates. HPRT was used for normalization. The "no RT" and "no-template" controls were included. The primer sequences used for qPCR are as follows:

```
IFN-λ1:
Forward: CTTCCAAGCCCACCCCAACT       (SEQ ID NO: 18)

Reverse: GGCCTCCAGGACCTTCAGC        (SEQ ID NO: 19)

HPRT:
Forward: GCAAGACGTTCAGTCCTGTGGATAA  (SEQ ID NO: 20)

Reverse: CAGCCCTGGCGTCGTGATTAGT     (SEQ ID NO: 21)

BLIMP-1:
Forward  CTCTGCCAATCCCTGAAACC       (SEQ ID NO: 22)

Reverse: TGGACTGGGTAGAGATGAACGA     (SEQ ID NO: 23)

GAPDH:
Forward: TGCACCACCACCTGCTTAG        (SEQ ID NO: 24)

Reverse: GGATGCAGGGATGATGTTC        (SEQ ID NO: 25)

ZEB1:
Forward: GCACCTGAAGAGGACCAGAG       (SEQ ID NO: 26)

Reverse: GCCTCTATCACAATATGGACAGG    (SEQ ID NO: 27)
```

Luciferase Assay

Transfected cells were stimulated with poly I:C for a given time period (3 hours) in 96-well plates. The Dual-Luciferase Assay Kit (Promega, San Luis Obispo, Calif.) was utilized according to manufacturer's instructions to perform the luciferase assay at the indicated timepoints. The Renilla luciferase-expressing pGL4.74 vector (Promega, San Luis Obispo, Calif.) was used for normalization and the pGL4.13 vector (Promega, San Luis Obispo, Calif.) containing an SV40 promoter-driven Firefly luciferase gene was included as a positive control.

Western Blotting

Western blotting was performed using 40 µg of whole cell extract from BEAS-2B cells that had been stimulated with poly I:C. The antibodies were directed against BLIMP-1 (Cell Signaling Technology, Danvers, Mass.), ZEB1 (Santa Cruz Biotechnology, Santa Cruz, Calif.) and Actin (Sigma Ronkonkoma, N.Y.).

ELISA

The IFN-λ1 ELISA was performed using the Duo Set ELISA kit according to the manufacturer's protocol (R&D Systems, Minneapolis, Minn.) on supernatants from siRNA transfected BEAS-2B cells that had been stimulated with poly I:C for up to 32 hours.

ChIP Assays

BEAS-2B cells grown in LHC-9 were stimulated with poly I:C for various lengths of time (0, 90, 135, 225, or 270 minutes). The ChIP assays were performed using the E-Z ChIP kit (Millipore, Billerica, Mass.) according to the manufacturer's instructions with minor modifications. $0.2 \times 10^6$ cells/IP were sonicated at 50% power for 4×30s bursts using a Branson sonifier (Emerson Industrial Automation, Danbury, Conn.). Binding site occupancy was monitored by SYBR Green-based qPCR according to conventional methods using the Brilliant II SYBR qPCR kit (Stratagene, La Jolla, Calif.). The following equation was utilized to quantify the binding based from the qPCR raw data: Fold Enrichment=$2^{[(Ct(ZEB1)-Ct(input))-(Ct(IgG)-Ct(input))]}$.

The following primers were designed to amplify specific regions of interest:

```
F1: TCTCGAACTCCTGACCTCAAGT          (SEQ ID NO: 28)

R1: CTCTCTTATGAGCTGGGACACC          (SEQ ID NO: 29)

F2: GAGGCTACAGTATTGCCAGC            (SEQ ID NO: 30)

R2: CCTGCATCTTTGGCTTCAG             (SEQ ID NO: 31)
```

-continued

| F3: | GAAACAGGATCTCACTCCATC | (SEQ ID NO: 32) |
| --- | --- | --- |
| R3: | TCAGCCAACTGGCCTCAG | (SEQ ID NO: 33) |
| F4: | CCTGAGGCCAGTTGGCTG | (SEQ ID NO: 34) |
| R4: | AATGGGCAATCCAAGATGATG | (SEQ ID NO: 35) |
| F5: | ACATTGGGTAACAACGGGTCT | (SEQ ID NO: 36) |
| R5: | GCTGGTGATGCGTTAATTCTG | (SEQ ID NO: 37) |
| F6: | CCTAATCTCAGCCTCCGTCA | (SEQ ID NO: 38) |
| R6: | CTGGGAGCTGCATCAAGAAG | (SEQ ID NO: 39) |

While the present invention has been described in connection with specific embodiments thereof, it will be understood that it is capable of further modifications and this application is intended to cover any variations of the invention thereof. One of skill in the art will recognize that various modifications may be made to the embodiments described herein without departing from the spirit and scope of the invention, which is defined by the appended claims. All the non-patent literature, patent applications, patents and referenced genes cited in this application are incorporated by reference in their entirety.

REFERENCES

1. Almeida, G. M. et al. Antiviral activity of type I interferons and interleukins 29 and 28a (type III interferons) against Apeu virus. *Antiviral Res* 80, 302-308 (2008).
2. Brand, S. et al. IL-28A and IL-29 mediate antiproliferative and antiviral signals in intestinal epithelial cells and murine CMV infection increases colonic IL-28A expression. *Am J Physiol Gastrointest Liver Physiol* 289, G960-8 (2005).
3. Bullens, D. M. et al. Type III IFN-lambda mRNA expression in sputum of adult and school-aged asthmatics. *Clin Exp Allergy* 38, 1459-1467 (2008).
4. Contoli, M. et al. Role of deficient type III interferon-lambda production in asthma exacerbations. *Nat Med* 12, 1023-1026 (2006).
5. Corne, J. M. et al. Frequency, severity, and duration of rhinovirus infections in asthmatic and non-asthmatic individuals: a longitudinal cohort study. *Lancet* 359, 831-834 (2002).
6. Dellgren, C., Gad, H. H., Hamming, O. J., Melchjorsen, J. & Hartmann, R. Human interferon-lambda3 is a potent member of the type III interferon family. *Genes Immun* (2008).
7. Donnelly, R. P., Sheikh, F., Kotenko, S. V. & Dickensheets, H.
The expanded family of class II cytokines that share the IL-10 receptor-2 (IL-10R2) chain. *J Leukoc Biol* 76, 314-321 (2004).
8. Dumoutier, L., Leemans, C., Lejeune, D., Kotenko, S. V. & Renauld, J. C. Cutting edge: STAT activation by IL-19, IL-20 and mda-7 through IL-20 receptor complexes of two types. *J Immunol* 167, 3545-3549 (2001).
9. Ank, N. et al. An important role for type III interferon (IFN-lambda/IL-28) in TLR-induced antiviral activity. *J Immunol* 180, 2474-2485 (2008).
10. Hansbro, N. G., Horvat, J. C., Wark, P. A. & Hansbro, P. M. Understanding the mechanisms of viral induced asthma: new therapeutic directions. *Pharmacol Ther* 117, 313-353 (2008).
11. Jordan, W. J. et al. Human interferon lambda-1 (IFN-lambda1/IL-29) modulates the Th1/Th2 response. *Genes Immun* 8, 254-261 (2007).
12. Jordan, W. J. et al. Modulation of the human cytokine response by interferon lambda-1 (IFN-lambda1/IL-29). *Genes Immun* 8, 13-20 (2007).
13. Kotenko, S. V. The family of IL-10-related cytokines and their receptors: related, but to what extent? *Cytokine Growth Factor Rev* 13, 223-240 (2002).
14. Kotenko, S. V. & Langer, J. A. Full house: 12 receptors for 27 cytokines. *Int Immunopharmacol* 4, 593-608 (2004).
15. Kotenko, S. V. & Pestka, S. Jak-Stat signal transduction pathway through the eyes of cytokine class II receptor complexes. *Oncogene* 19, 2557-2565 (2000).
16. Kotenko, S. V. et al. IFN-lambdas mediate antiviral protection through a distinct class II cytokine receptor complex. *Nat Immunol* 4, 69-77 (2003).
17. Lasfar, A. et al. Characterization of the mouse IFN-lambda ligand-receptor system: IFN-lambdas exhibit antitumor activity against B16 melanoma. *Cancer Res* 66, 4468-4477 (2006).
18. Li, W., Lewis-Antes, A., Huang, J., Balan, M. & Kotenko, S. V. Regulation of apoptosis by type III interferons. *Cell Prolif* 41, 960-979 (2008).
19. Melchjorsen, J., Siren, J., Julkunen, I., Paludan, S. R. & Matikainen, S. Induction of cytokine expression by herpes simplex virus in human monocyte-derived macrophages and dendritic cells is dependent on virus replication and is counteracted by ICP27 targeting NF-kappaB and IRF-3. *J Gen Virol* 87, 1099-1108 (2006).
20. Novick, D., Cohen, B. & Rubinstein, M. The human interferon alpha/beta receptor: characterization and molecular cloning. *Cell* 77, 391-400 (1994).
21. Onoguchi, K. et al. Viral infections activate types I and III interferon genes through a common mechanism. *J Biol Chem* 282, 7576-7581 (2007).
22. Osterlund, P. I., Pietila, T. E., Veckman, V., Kotenko, S. V. & Julkunen, I. IFN regulatory factor family members differentially regulate the expression of type III IFN (IFN-lambda) genes. *J Immunol* 179, 3434-3442 (2007).
23. Pekarek, V., Srinivas, S., Eskdale, J. & Gallagher, G. Interferon lambda-1 (IFN-lambda1/IL-29) induces ELR (–) CXC chemokine mRNA in human peripheral blood mononuclear cells, in an IFN-gamma-independent manner. *Genes Immun* 8, 177-180 (2007).
24. Sato, A., Ohtsuki, M., Hata, M., Kobayashi, E. & Murakami, T. Antitumor activity of IFN-lambda in murine tumor models. *J Immunol* 176, 7686-7694 (2006).
25. Sheppard, P. et al. IL-28, IL-29 and their class II cytokine receptor IL-28R. *Nat Immunol* 4, 63-68 (2003).
26. Sommereyns, C., et al., IFN-lambda (IFN-lambda) is expressed in a tissue-dependent fashion and primarily acts on epithelial cells in vivo. *PLoS Pathog* 4(3), e1000017 (2008).
27. Srinivas, S. et al. Interferon-lambda1 (interleukin-29) preferentially down-regulates interleukin-13 over other T helper type 2 cytokine responses in vitro. *Immunology* (2008).
28. Vandewalle, C., F. Van Roy, and G. Berx, The role of the ZEB family of transcription factors in development and disease. *Cell Mol Life Sci* 66(5), 773 (2009).
29. Wu, L. and Belasco, J. G. Let me count the ways: mechanisms of gene regulation by miRNAs and siRNAs. *Mol Cell* 29(1), 1-7 (2008).

What is claimed is:

1. A method of increasing IFN-λ1 gene activity in an airway epithelial cell, comprising the steps of:
   i) providing an airway epithelial cell in need of increasing IFN-λ1 gene activity, said airway epithelial cell is viral-stimulated; and
   ii) exposing said airway epithelial cell to a siRNA oligonucleotide targeted against a transcriptional factor mRNA selected from the group consisting of EVI1 and CRX, thereby increasing IFN-λ1 gene activity in said airway epithelial cell, as indicated by an increase in IFN-λ1 protein expression,
   wherein said EVI1 mRNA has a nucleotide sequence set forth in Accession No: NM_001105077 and said CRX mRNA has a nucleotide sequence set forth in Accession No: NM_000554.

2. The method of claim 1, wherein said siRNA oligonucleotide is at least one siRNA oligonucleotide selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62 and SEQ ID NO: 63.

3. The method of claim 1, wherein said siRNA oligonucleotide is at least one siRNA oligonucleotide selected from the group consisting of SEQ ID NO: 56, SEQ ID NO: 57, SEQ ID NO: 58 and SEQ ID NO: 59.

4. The method of claim 1, wherein said siRNA oligonucleotide is at least one siRNA oligonucleotide selected from the group consisting of SEQ ID NO: 60, SEQ ID NO: 61, SEQ ID NO: 62 and SEQ ID NO: 63.

5. The method of claim 1, wherein said increased IFN-λ1 protein expression is measured by an increase in IFN-λ1 protein secretion.

6. The method of claim 1, wherein said increased IFN-λ1 protein expression is measured by an ELISA.

7. The method of claim 1, wherein said airway epithelial cell is a human airway epithelial cell.

8. The method of claim 1, wherein said siRNA oligonucleotide is a modified siRNA oligonucleotide.

9. A method of treating a human subject inflicted with an asthmatic disease, comprising the step of administering a therapeutically effective amount of a siRNA oligonucleotide to said human subject, said siRNA oligonucleotide is targeted against a transcriptional factor mRNA selected from the group consisting of EVI1 and CRX, and induces the production of IFN-λ1 protein having an amino acid sequence set forth in GenBank Accession No. NP_742152, and wherein said EVI1 mRNA has a nucleotide sequence set forth in Accession No: NM_001105077 and said CRX mRNA has a nucleotide sequence set forth in Accession No: NM_000554.

10. The method of claim 9, wherein said siRNA oligonucleotide is at least one oligonucleotide selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62 and SEQ ID NO: 63.

11. The method of claim 9, wherein said siRNA oligonucleotide is at least one oligonucleotide selected from the group consisting of SEQ ID NO: 56, SEQ ID NO: 57, SEQ ID NO: 58 and SEQ ID NO: 59.

12. The method of claim 9, wherein said siRNA oligonucleotide is at least one oligonucleotide selected from the group consisting SEQ ID NO: 60, SEQ ID NO: 61, SEQ ID NO: 62 and SEQ ID NO: 63.

* * * * *